United States Patent [19]

Tseng

[11] Patent Number: 4,921,527

[45] Date of Patent: May 1, 1990

[54] HERBICIDAL SULFONAMIDES

[75] Inventor: Chi-Ping Tseng, Wilmington, Del.

[73] Assignee: E. I. du Pont de Nemours and Company, Wilmington, Del.

[21] Appl. No.: 190,242

[22] Filed: May 4, 1988

Related U.S. Application Data

[63] Continuation-in-part of Ser. No. 80,471, Jul. 31, 1987, abandoned.

[51] Int. Cl.$^5$ ............ A01N 43/54; A01N 43/58; A01N 43/60; A01N 43/90; A01N 43/713; A01N 43/707; C07D 471/04; C07D 487/04

[52] U.S. Cl. ............................ 71/90; 71/92; 71/93; 544/321; 544/117; 544/278; 544/324; 544/118; 544/279; 544/331; 544/235; 544/280; 544/122; 544/236; 544/281; 544/123; 544/216; 544/282; 544/113; 544/219; 544/253; 544/112; 544/255; 544/295; 544/184; 544/256; 544/320; 544/183; 544/262; 544/180; 544/263; 544/116

[58] Field of Search ............ 71/90, 92, 93; 544/321, 544/324, 331, 122, 123, 113, 112, 184, 183, 180, 116, 117, 118, 235, 236, 216, 219, 255, 256, 262, 263, 278, 279, 280, 281, 282, 253, 295, 320

[56] References Cited

U.S. PATENT DOCUMENTS

| | | | |
|---|---|---|---|
| 4,369,320 | 1/1983 | Levitt et al. | 544/320 |
| 4,391,627 | 7/1983 | Levitt | 71/90 |
| 4,453,970 | 6/1984 | Levitt et al. | 71/93 |
| 4,605,433 | 8/1986 | Pearson et al. | 71/93 |
| 4,622,062 | 11/1986 | Wexler | 71/90 |
| 4,643,759 | 2/1987 | Thompson | 71/90 |
| 4,671,817 | 6/1987 | Wexler | 71/91 |
| 4,678,499 | 7/1987 | Pasteris et al. | 71/90 |
| 4,685,958 | 8/1987 | Pearson et al. | 71/93 |
| 4,723,987 | 2/1988 | Hanagan | 71/90 |
| 4,746,356 | 5/1988 | Douglass et al. | 71/93 |

FOREIGN PATENT DOCUMENTS

| | | |
|---|---|---|
| 70698 | 1/1983 | European Pat. Off. |
| 146263 | 6/1985 | European Pat. Off. |
| 238070 | 9/1987 | European Pat. Off. |
| 244097 | 11/1987 | European Pat. Off. |
| 244098 | 11/1987 | European Pat. Off. |
| 244166 | 11/1987 | European Pat. Off. |

*Primary Examiner*—John M. Ford

[57] ABSTRACT

The invention relates to sulfonylurea compounds with a substituted or unsubstituted bicyclic nine-membered ring having one to five heteroatoms which are preemergent and/or postemergent herbicides or plant growth regulants.

38 Claims, No Drawings

HERBICIDAL SULFONAMIDES

RELATED APPLICATION

This application is a continuation-in-part of application U.S. Ser. No. 080,471 filed July 31, 1987, now abandoned.

BACKGROUND OF THE INVENTION

This invention relates to novel sulfonylurea compounds, agriculturally suitable compositions thereof and a method of using them to control the growth of undesired vegetation.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks, and industrial storage areas. There are many products commercially available for these purposes, but the search continues for products which are more effective, less costly and environmentally safe.

The "sulfonylurea" herbicides are an extremely potent class of herbicides discovered within the last few years. A multitude of structural variations exist within this class of herbicides, but they generally consist of a sulfonylurea bridge, —SO$_2$NHCONH—, U.S. No. 4,369,320 and U.S. No. 4,453,970 disclose herbicidal quinolinylsulfonylureas.

U.S. No. 4,391,627 discloses herbicidal benzothiophenesulfonylureas.

EP-A-70,698 published 1/26/83 discloses herbicidal indolesulfonylureas.

EP-A-146,263, published 6/26/85 discloses herbicidal sulfonylureas of the formula $$\text{JSO}_2\text{NHCN A}\underset{R}{\overset{\overset{W}{\parallel}}{|}}$$

wherein
J is

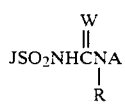

E is a bridge of 3 or 4 atoms, which may be substituted or unsubstituted, containing 0 to 2 heteroatoms selected from the group consisting of oxygen, sulfur and nitrogen and also containing 1-4 atoms of carbon, said bridge together with two carbon attachment sites forming a partially saturated 5- to 6-membered carbocyclic or heterocyclic ring; or E is a bridge of 3 or 4 atoms which may be substituted or unsubstituted containing at least 1 heteroatom selected from 0–1 oxygen or sulfur or 0–2 nitrogen and 1–3 atoms of carbon, said bridge together with two carbon attachment sites forming an unsaturated 5- to 6-membered heterocyclic ring, with the proviso that when E contains two atoms of oxygen or sulfur, then they must be separated by at least one atom of carbon and that oxygen and sulfur are only linked to each other if the sulfur is in the form of SO or SO$_2$; in the bridging group E, nitrogen may take the form of N or N—O, sulfur may take the form of S, SO or SO$_2$, and one of the atoms of carbon may be a carbonyl, thiocarbonyl or the cyclic 5- and 6-membered ketals thereof; and G is O, S, NH or NCH$_3$.

U.S. No. 4,622,062 disclosed herbicidal sulfonylureas of the formula

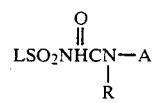

wherein
L, in part, is

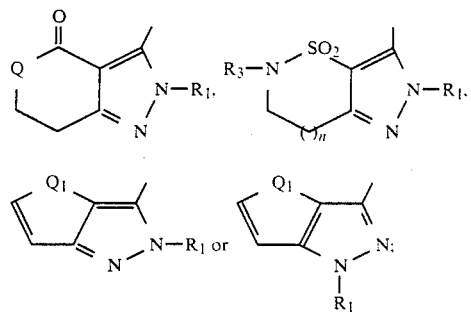

Q$_1$ is O, S or SO$_2$.

U.S. No. 4,643,759 discloses herbicidal compounds of the formula

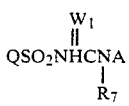

wherein
Q is

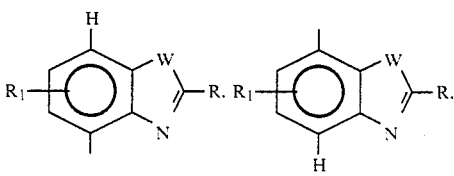

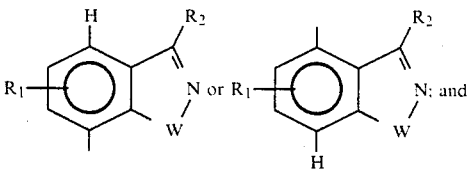

W is O, S or NR$_3$

U.S. No. 4,678,499 discloses herbicidal compounds of the formula

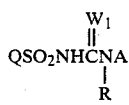

wherein
Q is

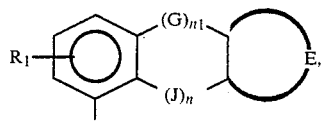

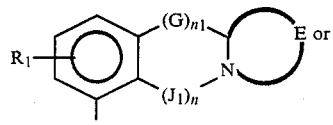

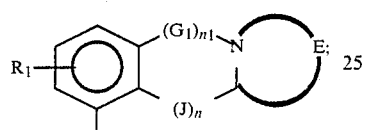

G is $CH_2$, $CH_2CH_2$, O, S, NH, $NCH_3$ or $CH=CH$;
$G_1$ is $CH_2$, $CH_2CH_2$ or $CH=CH$;
J, in part, is $CH_2$, C(O), $S(O)_m$, O, NH or $NCH_3$;
n and $n_1$ are independently 0 or 1; and
E is a bridge of 3 or 4 atoms containing 0-2 heteroatoms selected from the group consisting of oxygen, sulfur and nitrogen, wherein 1 atom of sulfur may take the form of SO or $SO_2$, said bridge also containing 1 to 4 atoms of carbon wherein 1 atom of carbon may take the form of C=O, said bridge together with two attachment sites forming a non-aromatic heterocyclic or carbocyclic ring optionally substituted by 1 to 3 substituent groups selected from the group L, or E is a bridge of 3 or 4 atoms containing 0-1 heteroatoms of oxygen or sulfur and 0-3 heteroatoms of nitrogen, said bridge also containing 0-4 atoms of carbon, said bridge together with two attachment sites forming an aromatic heterocyclic or carbocyclic ring optionally substituted by 1 to 3 substituents selected from the group L, with the proviso that when E contains two oxygen atoms or two sulfur atoms said atoms must be separated by at least one atom of carbon and that oxygen and sulfur are only linked to each other if the sulfur is in the form of SO or $SO_2$;

U.S. No. 4,671,817 discloses herbicidal compounds of the formula

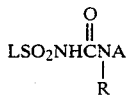

wherein L is

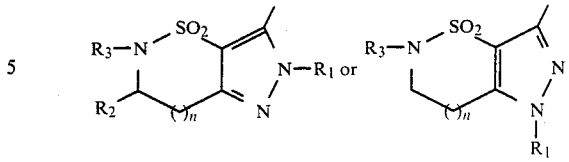

U.S. No. 4,723,987 discloses herbicidal compounds of the formula

wherein
J is

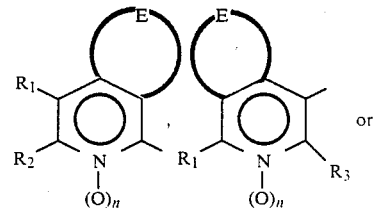

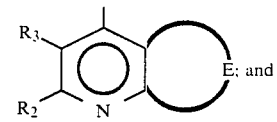

E is a bridge of 3 or 4 atoms, which may be substituted or unsubstituted, containing 0-2 heteroatoms selected from the group consisting of oxygen, sulfur and nitrogen, and also containing 1-4 atoms of carbon, said bridge together with two carbon attachment sites forming a partially saturated 5- or 6-membered carbocyclic or heterocyclic ring; or E is a bridge of 3 or 4 atoms, which may be substituted or unsubstituted, containing 0-1 heteroatoms selected from oxygen or sulfur, 0-2 heteroatoms of nitrogen and 1-4 atoms of carbon said bridge together with two carbon attachment sites forming a fully unsaturated 5- or 6-membered carbocyclic or heterocyclic ring, with the proviso that when E contains two atoms of oxygen or sulfur, they must be separated by at least one atom of carbon, and the oxygen and sulfur are only linked to each other if the sulfur is in the form of SO or $SO_2$; in the bridging group E, sulfur may take the form of S, SO or $SO_2$, and one of the atoms of carbon may be a carbonyl, thiocarbonyl or the cyclic 5- and 6-membered ketals thereof.

South African Patent Application 84/8844 and its equivalent U.S. No. 4,605,433, discloses substituted 1,2,4-triazolo-[1,5-a]pyrimidine-sulfonamides of the following formula as herbicides and plant growth regulants.

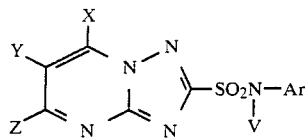

U.S. No. 4,685,958, discloses substituted 2-amino-1,2,4-triazolo[1,5-A]-1,3,5-triazines of the following formula as herbicides.

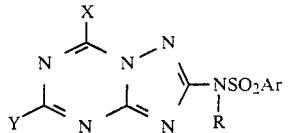

EP-A-244,097, published on Nov. 4, 1987, discloses herbicidal pyrazolopyrimidine derivatives of the formula

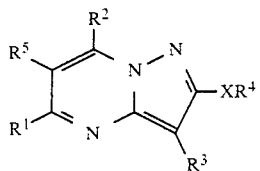

wherein
X is $-NR-SO_2-$, $-SO_2-O-$, $-SO_2-NR-$ or $-S(O)_nCR'R''-$.

EP-A-244,098, published on Nov. 4, 1987, discloses herbicidal thiazolotriazolesulfonamides of the formula

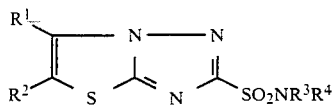

U.S. Ser. No. 07/039492 which was allowed discloses herbicidal benzotriazole sulfonylureas.

EP-A-244,166, published Nov. 4, 1987, discloses herbicidal compounds of the formula

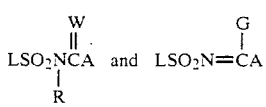

wherein
L, in part, is a benzene, naphthalene, pyrazole, thiophene, pyridine, benzothiophene or an indole moiety;
A, in part is

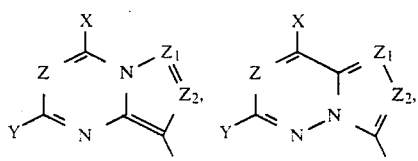

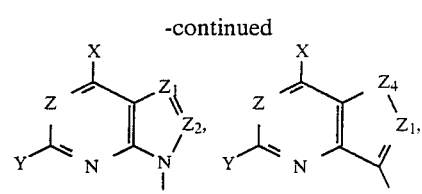

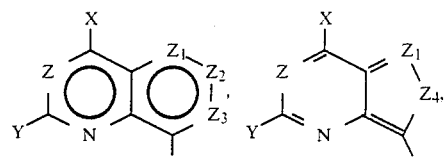

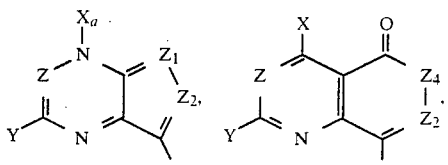

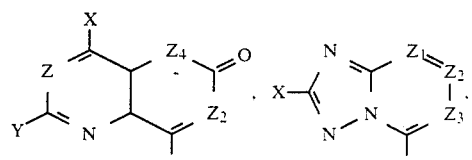

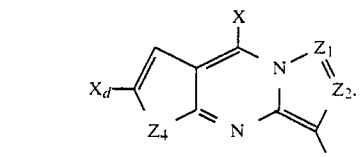

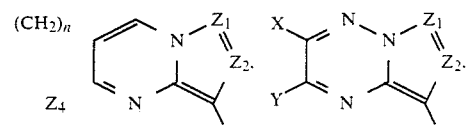

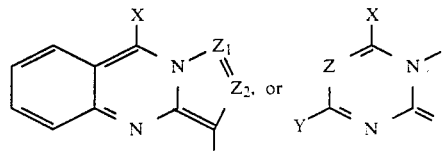

Z is CH, N, CCH$_3$, CEt, CCl or CBr;
Z$_1$ is C—U, N or N—O;
Z$_2$ and Z$_3$ are independently N or C—U;
Z$_4$ is NCH$_3$, O, S or CH$_2$; and
U is H, F, Cl, Br, C$_1$-C$_2$ alkyl optionally substituted by F, Cl, Br or OCH$_3$, CN, NO$_2$, NMe$_2$, OR$_{22}$, or SR$_{22}$, or CO$_2$CH$_3$.

EP-A-238,070, published Sept. 23, 1987, discloses compounds of the formula

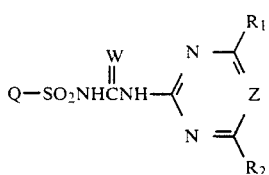

wherein

Q is a condensed heterocyclic group having N atoms in the bridgehead which may be substituted;

W is O or S;

$R_1$ and $R_2$ are independently alkyl, alkoxy or halogen; and

Z is CH or N.

SUMMARY OF THE INVENTION

This invention relates to novel compounds of Formula I, their agriculturally suitable compositions and their method-of-use as preemergent and/or postemergent herbicides or plant growth regulants $$L-SO_2\underset{H}{N}\overset{W}{\underset{\parallel}{C}}-\underset{R}{N}A \qquad I$$

wherein

L is

[Structures L-1 through L-20 shown]

$R^1$ is H, halogen, $C_1$–$C_3$ alkyl, $C_1$–$C_3$ haloalkyl, $OR^6$, $SR^6$, $S(O)R^6$, $S(O)_2R^6$, $CO_2R^7$, $C(O)NR^8R^9$, $S(O)_2NR^{10}R^{11}$, $C_2$–$C_3$ alkenyl, $C_2$–$C_3$ haloalkenyl, $C_2$–$C_3$ alkynyl, $NO_2$, CN, $C(O)R^{12}$, $C(R^{13})=NOR^{14}$ or $C_1$–$C_2$ alkyl substituted by $C_1$–$C_2$ alkoxy, $C_1$–$C_2$ alkylthio or CN;

$R^2$ is H, $C_1$–$C_3$ alkyl, $C_1$–$C_3$ alkoxy, $C_1$–$C_2$ haloalkoxy or $C_1$–$C_2$ alkyl substituted with $OCH_3$, $SCH_3$ or CN;

$R^3$ is H, $CH_3$ or $OCH_3$;

$R^4$ is H or $CH_3$;

$R^5$ is H, halogen, $C_1$–$C_3$ alkyl, $C_1$–$C_3$ haloalkyl, $OR^6$, $SR^6$, $S(O)_2R^6$, $CO_2R^7$, $C(O)NR^8R^9$, $S(O)_2NR^{10}R^{11}$, $C_2$–$C_3$ alkenyl, $C_2$–$C_3$ haloalkenyl, $C_2$–$C_3$ alkynyl, $NO_2$, CN, $C(O)R^{12}$, or $C_1$–$C_2$ alkyl substituted by $C_1$–$C_2$ alkoxy, $C_1$–$C_2$ alkylthio or CN;

$R^6$ is $C_1$–$C_3$ alkyl, $C_1$–$C_3$ haloalkyl, $C_3$ alkenyl, $C_2$–$C_3$ haloalkenyl, propargyl, cyclopropyl, cyclopropylmethyl or —$CH_2CH_2$— substituted by OH, $C_1$–$C_2$ alkoxy, SH, $C_1$–$C_2$ thioalkyl or CN;

$R^7$ is $C_1$–$C_4$ alkyl, $C_2$–$C_3$ haloalkyl, allyl, propargyl, cyclopropyl, cyclopropylmethyl, or —$CH_2CH_2$— substituted by OH, $OCH_3$, $SCH_3$ or CN;

$R^8$ is H or $C_1$–$C_2$ alkyl;

$R^9$ is $C_1$–$C_3$ alkyl, $C_1$–$C_3$ alkoxy, allyl, propargyl, cyclopropyl, CH$_2$CN, CH$_2$CH$_2$CN or CH$_2$CH$_2$OCH$_3$;

$R^{10}$ is H or $C_1$–$C_3$ alkyl;

$R^{11}$ is $C_1$–$C_3$ alkyl, $C_1$–$C_3$ alkoxy, allyl, propargyl, cyclopropyl, cyclopropylmethyl, CH$_2$CN, CH$_2$CN, CH$_2$CH$_2$CN or CH$_2$CH$_2$OCH$_3$;

$R^{10}$ and $R^{11}$ can be taken together to form a ring consisting of (—CH$_2$—)$_4$, (—CH$_2$—)$_5$ or (—CH$_2$CH$_2$—)$_2$O;

$R^{12}$ is H, $C_1$–$C_3$ alkyl or cyclopropyl;

$R^{13}$ is H, $C_1$–$C_3$ alkyl, cyclopropyl, Cl, CN, OCH$_3$, SCH$_3$ or N(CH$_3$)$_2$;

$R^{14}$ is H or $C_1$–$C_3$ alkyl;

Z is N or CH;

$Z^1$ is N, CH or CCH$_3$;

$Z^2$ is O, S or NCH$_3$;

$Z^3$ is O, S or N—$R^{15}$;

$R^{15}$ is H, $C_1$–$C_2$ alkyl, $C_1$–$C_2$ haloalkyl, CH$_2$CH$_2$OCH$_3$, CH$_2$CH$_2$SCH$_3$, CH$_2$CN or CO$_2$CH$_3$;

W is O or S;

R is H or CH$_3$;

A is

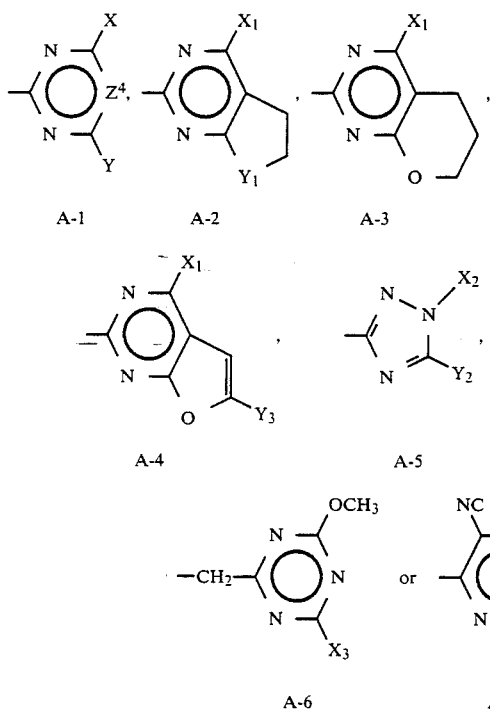

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkyl thioalkyl, $C_2$–$C_5$ alkylsulfinylalkyl, $C_2$–$C_5$ alkylsulfonylalkyl, $C_1$–$C_4$ haloalkyl, $C_2$–$C_4$ alkynyl, $C_3$–$C_5$ cycloalkyl, azido, cyano,

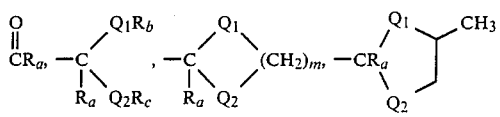

or N(OCH$_3$)CH$_3$;

m is 2 or 3;

Q$_1$ and Q$_2$ are independently O or S;

R$_a$ is H or $C_1$–$C_3$ alkyl;

R$_b$ and R$_c$ are independently $C_1$–$C_3$ alkyl;

$Z^4$ is CH, N, CCH$_3$, CC$_2$H$_5$, CCl or CBr;

$Z^5$ is CH or N;

Y$_1$ is O or CH$_2$;

X$_1$ is CH$_3$, OCH$_3$, OC$_2$H$_5$ or OCF$_2$H;

X$_2$ is CH$_3$, C$_2$H$_5$ or CH$_2$CF$_3$;

Y$_2$ is OCH$_3$, OC$_2$H$_5$, SCH$_3$, SC$_2$H$_5$, CH$_3$ or CH$_2$CH$_3$;

X$_3$ is CH$_3$ or OCH$_3$;

Y$_3$ is H or CH$_3$;

X$_4$ is CH$_3$, OCH$_3$, OC$_2$H$_5$, CH$_2$OCH$_3$ or Cl;

Y$_4$ is CH$_3$, OCH$_3$, OC$_2$H$_5$ or Cl;

and their agriculturally suitable salts; provided that (1) when X is halogen, then $Z^4$ is CH and Y is OCH$_3$, OC$_2$H$_5$, NH$_2$, NHCH$_3$, N(CH$_3$)$_2$, OCF$_2$H, OCF$_2$Br or N(OCH$_3$)CH$_3$;

(2) when X or Y is $C_1$ haloalkoxy, then $Z^4$ is CH;

(3) when W is S, then R is H, A is A-1, $Z^4$ is CH or N, and Y is CH$_3$, OCH$_3$, OC$_2$H$_5$, CH$_2$OCH$_3$, C$_2$H$_5$, CF$_3$, SCH$_3$, OCH$_2$CH=CH$_2$, OCH$_2$C≡CH, OCH$_2$CH$_2$OCH$_3$, CH(OCH$_3$)$_2$ or

(4) when the total number of carbon atoms of X and Y is greater than four, then the greatest combined number of carbons of any two substituents on an L, selected from $R^1$, $R^2$, $R^3$, $R^4$, $R^5$ and $R^{15}$ is less than or equal to six;

(5) X$_4$ and Y$_4$ are not simultaneously Cl;

(6) the total number of carbon atoms of $R^{10}$ and $R^{11}$ is less than or equal to five.

In the above definitions, the term "alkyl", used either alone or in compound words such as "alkylthio" or "haloalkyl", denotes straight chain or branched alkyl, e.g. methyl, ethyl, n-propyl, isopropyl or the different butyl isomers.

Alkoxy denotes methoxy, ethoxy, n-propyloxy, isopropyloxy and the different butyloxy isomers.

Alkenyl denotes straight chain or branched alkenes, e.g. 1-propenyl, 2-propenyl, 3-propenyl and the different butenyl isomers.

Alkynyl denotes straight chain or branched alkynes, e.g. ethynyl, 1-propynyl, 2-propynyl and the different butynyl isomers.

Alkylsulfonyl denotes methylsulfonyl, ethylsulfonyl and the different propylsulfonyl isomers.

Alkylthio, alkylsulfinyl, alkylamino, etc. are defined analogously to the above examples.

Cycloalkyl denotes cyclopropyl, cyclobutyl and cyclopentyl.

The term "halogen," either alone or in compound words such as "haloalkyl," denotes fluorine, chlorine, bromine or iodine. Further, when used in compound words such as "haloalkyl" said alkyl may be partially halogenated or fully substituted with halogen atoms and said halogen atoms may be the same or different. Examples of haloalkyl include $CH_2CH_2F$, $CF_2CF_3$ and $CH_2CHFCl$.

The total number of carbon atoms in a substituent group is indicated by the $C_i-C_j$ prefix where i and j are numbers from 1 to 5. For example, $C_1-C_3$ alkylsulfonyl would designate methylsulfonyl through propylsulfonyl, $C_2$ alkoxyalkoxy would designate $OCH_2OCH_3$, $C_2$ cyanoalkyl would designate $CH_2CN$ and $C_3$ cyanoalkyl would designate $CH_2CH_2CN$ and $CH(CN)CH_3$.

Compounds of the invention preferred for reasons of increased ease of synthesis and/or greater herbicidal efficacy are:
1. Compounds of Formula I where L is L-1,, L-3, L-4a, L-4b, L-5, L-6, L-7, L-10, L-11, L-14, L-16, L-19 or L-20.
2. Compounds of Preferred 1 where W is O and $Z^4$ is CH or N.
3. Compounds of Preferred 2 where
   X is $C_1-C_2$ alkyl, $C_1-C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$;
   Y is H, $C_1-C_2$ alkyl, $C_1-C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$, $$\underset{R_a\ Q_2R_c}{\overset{O}{\underset{\|}{CR_a,}}\ -\overset{Q_1R_b}{\underset{|}{C}}/}, \quad -\overset{Q_1}{\underset{|}{C}}(CH_2)_m, \quad CR_a\overset{Q_1}{\underset{Q_2}{\diagup}}\overset{CH_3}{\diagdown},$$

$OCF_2H$, $OCF_2Br$, $SCF_2H$, cyclopropyl, $C\equiv CH$ or $C\equiv CCH_3$;
   $R_a$ is H or $CH_3$; and
   $R_b$ and $R_c$ are independently $CH_3$ or $CH_2CH_3$.
4. Compounds of Preferred 3 where
   $R^1$ is H, halogen, $C_1-C_2$ alkyl, $C_1-C_2$ haloalkyl, $OR^6$, $SR^6$, $S(O)R^6$, $S(O)_2R^6$, $CO_2R^7$, $C(O)NR^8R^9$, $S(O)_2NR^{10}R^{11}$, $C_2-C_3$ alkenyl, $C_2-C_3$ haloalkenyl, $NO_2$, CN, $C(O)R^{12}$, $C(R^{13})=NOR^{14}$ or $C_1-C_2$ alkyl substituted by $C_1-C_2$ alkoxy, $C_1-C_2$ alkylthio or CN;
   $R^2$ is H, $CH_3$ or $OCH_3$;
   $R^5$ is H, halogen, $C_1-C_2$ alkyl, $C_1-C_2$ haloalkyl, $OR^6$, $SR^6$, $S(O)R^6$, $S(O)_2R^6$, $CO_2R^7$, $C(O)NR^8R^9$, $S(O)_2NR^{10}R^{11}$, $C_2-C_3$ alkenyl, $C_2-C_3$ haloalkenyl, $NO_2$, CN, $C(O)R^{12}$, or $C_1-C_2$ alkyl substituted by $C_1-C_2$ alkoxy, $C_1-C_2$ alkylthio or CN;
   $R^6$ is $C_1-C_3$ alkyl, $C_1-C_3$ haloalkyl, $C_3$ alkenyl, $C_2-C_3$ haloalkenyl, propargyl, cyclproyl or cyclopropylmethyl.
5. Compounds of Preferred 4 where
   A is A-1;
   X is $CH_3$, $OCH_3$, $OCH_2CH_3$, Cl or $OCF_2H$;
   Y is $CH_3$, $OCH_3$, $C_2H_5$, $CH_2OCH_3$, $NHCH_3$, $CH(OCH_3)_2$ or cyclopropyl; and
   R is H.
6. Compounds of Preferred 5 where L is L-1.
7. Compounds of Preferred 5 where L is L-3.
8. Compounds of Preferred 5 where L is L-4a.
9. Compounds of Preferred 5 where L is L-4b.
10. Compounds of Preferred 5 where L is L-5.
11. Compounds of Preferred 5 where L is L-6.
12. Compounds of Preferred 5 where L is L-7.
13. Compounds of Preferred 5 where L is L-10.
14. Compounds of Preferred 5 where L is L-11.
15. Compounds of Preferred 5 where L is L-14.
16. Compounds of Preferred 5 where L is L-19.
17. Compounds of Preferred 5 where L is L-20.

The compounds of this invention are active are active preemergent and postemergent herbicides and plant growth regulators.

DETAILED DESCRIPTION OF THE INVENTION

Synthesis

Compounds of Formula I can be prepared by one or more of the procedures shown in Equations 1, 4, and 5 wherein L, R, and A are as previously defined. The requisite intermediates for these reactions can be prepared by one or more of the methods described in this section. In some cases, substituents on the starting materials may be incompatible with the reaction conditions described. It will be readily apparent to one skilled in the art to use either standard protecting groups (e.g., ketal as a protecting group for ketone) or one of the alternative methods described.

Equation 1

$$L-SO_2N=C=W + HNA \longrightarrow I$$
$$\quad\quad\quad\quad\quad\quad\quad\quad\quad\quad |$$
$$\quad\quad\quad\quad\quad\quad\quad\quad\quad\quad R$$
$$\text{II} \quad\quad\quad\quad\quad \text{III}$$

The reaction of Equation 1 is best carried out in an inert aprotic organic solvent such as dichloromethane, 1,2-dichloroethane, tetrahydrofuran, or acetonitrile, at a temperature between 20° and 85° C. The order of addition is not critical; however, it is often convenient to add the sulfonyl isocyanate or a solution of it in the reaction solvent, to a stirred suspension of the amine.

In some cases, the desired product is insoluble in the reaction solvent at ambient temperature and crystallizes from it in pure form. Products soluble in the reaction solvent are isolated by evaporation of the solvent. Compounds of Formula I then may be purified by trituration of the evaporation residue with solvents such as 1-chlorobutane or ethyl ether and filtration, by recrystallization from mixtures of solvents such as 1,2-dichloroethane, 1-chlorobutane and heptane or by chromatography on silica gel.

Sulfonyl isocyanates (II, W is O) can be prepared from the corresponding sulfonamides (IV) by one of the following two general methods.

Equation 2

$$LSO_2NH_2 \xrightarrow[COCl_2, \text{cat.}]{CH_3(CH_2)_3NCO} \text{II. W is O}$$

IV

The sulfonamide IV is reacted with an alkyl isocyanate (e.g., n-butyl isocyanate) in a solvent whose boiling point is above 135° C., such as xylene. The reaction can optionally be carried out in the presence of a catalytic amount of 1,4-diaza[2.2.2]bicyclooctane (DABCO). The reaction mixture is heated to 135°–140° C. and held at that temperature for 5–60 minutes, after which phosgene is slowly added at such a rate that the temperature remains between 133° and 135° C. When the consumption of phosgene has ceased, the mixture is cooled and filtered to remove insoluble material. Finally, the solvent, alkyl isocyanate, and excess phosgene are evaporated, leaving the sulfonyl isocyanate (II).

If desired, the alkyl isocyanate-sulfonamide adduct can be made and isolated before reaction with the phosgene. In this case the sulfonamide (IV), alkyl isocyanate, and anhydrous base (e.g. $K_2CO_3$ or acetonitrile) are mixed and heated under reflux for 1 to 6 hours. The reaction mixture is then diluted with water, and the pH is adjusted to about 3 with acid (e.g. HCl, $H_2SO_4$). The adduct is filtered out and dried, and then reacted with phosgene as described above. This procedure modification is especially useful with sulfonamide (IV) is high melting and has low solubility in the phosgenation solvent.

Sulfonyl isocyanates (II, W is O) can also be prepared by the following method.

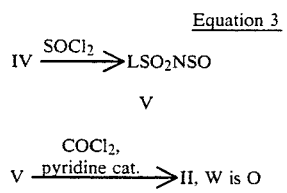

The sulfonamide (IV) is heated at reflux in an excess of thionyl chloride. The reaction is continued until the sulfonamide protons are no longer detectable in the proton magnetic resonance spectrum. From 16 hours to 5 days is typically sufficient for complete conversion to the thionylamide (V) (Equation 3a).

The thionyl chloride is evaporated and the residue is treated with an inert solvent (e.g. toluene) containing at least one equivalent (typically 2-3 equivalents) of phosgene. A catalytic amount of pyridine (typically 0.1 equivalent) is added, and the mixture is heated to about 60°-140° C., with 80°-100° C. preferred. Conversion to the isocyanate (II, W is O) is usually substantially complete within 15 minutes to 3 hours (Equation 3b). The mixture is then cooled and filtered, and the solvent is evaporated, leaving the sulfonyl isocyanate (II, W is O).

Sulfonyl isothiocyanates (II, W is S) can be prepared from the corresponding sulfonamides (IV) by reaction with carbon disulfide and potassium hydroxide followed by treatment of the resulting dipotassium salt VI with phosgene. Such a procedure is described in *Arch. Pharm.*, 299, 174 (1966).

Many of the compounds of Formula I can be prepared by the procedure shown in Equation 4.

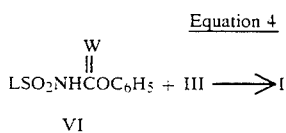

The reaction of Equation 4 can be carried out by contacting phenylcarbamates or phenylthiocarbamates of Formula VI with aminoheterocycles of Formula III in an inert organic solvent such as dioxane or tetrahydrofuran at temperatures of about 20°-100° C. for a period of about one-half to twenty-four hours. The product can be isolated by evaporation of the reaction solvent and purified by methods previously described.

Phenylcarbamates and phenylthiocarbamates of Formula VI can be prepared by the methods described, or modifications thereof known to those skilled in the art, in U.S. Pat. No. 4,443,243.

Alternatively, many of the compounds of Formula I can be prepared by the method described in Equation 5.

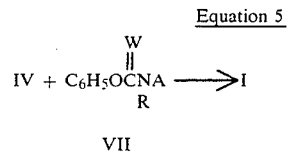

The reaction of Equation 5 can be carried out by contacting equimolar amounts of a sulfonamide of Formula IV with a heterocyclic phenylcarbamate or phenylthiocarbamate of Formula VII in the presence of a base such as 1,8-diazabicyclo[5.4.0]undec-7-ene (DBU), by methods analogous to those described in South African Patent Application 83/0441. The phenylcarbamates and phenylthiocarbamates of Formula VII can be prepared by methods, or modifications thereof known to those skilled in the art, described in South African Patent Application 82/5671 and South African Patent Application 82/5045.

The sulfonamides IV of this invention may be prepared in a variety of ways some of which are described in Equations 6 through 15.

The sulfonamides IV of this invention can be prepared from the corresponding sulfonyl chloride of Formula VIII. The preparation of sulfonamides from sulfonyl chlorides is widely reported in the literature; for reviews see: F. Hawking and J. S. Lawrence. "The Sulfonamides". H. K. Lewis and Co., London, 1950, and E. H. Northey, "The Sulfonamides and Allied Compound", Reinhold Publishing Corp., New York, 1984.

$$L—SO_2Cl \qquad\qquad VIII$$

The requisite sulfonyl chloride of Formula VIII may be synthesized from IX, X, or XI by known methods or with slight modification thereof, by one skilled in the art.

wherein L is as previously defined.
U is Cl, Br or I
L' is L-1, L-2, L-3, L-4a, L-4b, L-5, L-6, L-7, L-10, L-11, L-12, L-13, L-19 or L-20.
Several representative teaching are listed below.
Aromatic nitro group may be transformed into sulfonyl chloride by reduction, diazotization and coupling with sulfur dioxide/cupric chloride as taught in U.S. Pat. No. 4,310,346.
European Publication No. 94,821 (published 11/23/83) describes the displacement of aromatic halide with thiolate anions and subsequent oxidative chlorination to yield sulfonyl chlorides.
Halogen metal exchange of aromatic halides or proton-metal exchange of aromatic followed by quenching with sulfur dioxide give sulfinate salts.
These salts yield sulfonyl chlorides upon reaction with N-chlorosuccinimide as taught in U.S. Pat. No. 4,481,029 (issued 11/6/84).

Directed proton-metal exchange of aromatic compounds has been reviewed by Gschweard and Rodriquez, *Org. Reactions,* 26, (1979). Also aryllithiums may be converted directly to arylsulfonyl chloride with sulfonyl chloride as described by S. N. Bhattacharya, et. al, in *J. Chem. Soc. C.,* 1265 (1968).

Electrophilic chlorosulfonation of an aromatic ring to give a sulfonyl chloride is well known in the literature. Its application is described by E. H. Huntress, et al., in *J. Am. Chem. Soc.,* 62, 511-14 and 603-4 (1940), and W. E. Kirkpatrick, et al., in *J. Med. Chem.,* 20, 386 (1977).

The compounds of Formula XI, where L' is L-1, L-2, L-3, L-4a, L-4b, L-5, L-6, L-7, L-10, L-11, L-12, L-13 L-19 or L-20, may be synthesized from compounds of Formula IX by nitration as taught by B. M. Lynch, et al., in *Can. J. Chem.,* 53, 119 (1975), W. E. Kirkpatrick, et al., in *J. Med. Chem.,* 20, 386 (1977) and B. Stanovnik in *Lect. Heterocyclic. Chem.,* 2, 27.

The compounds of Formula $IX_1$, can be synthesized by the methods shown below in Equation 6 through 10.

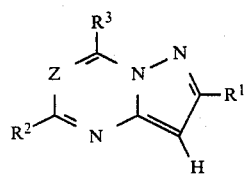

wherein $R^1$, $R^2$, $R^3$ and Z are as previously defined.

Equation 6 illustrates the reaction of β-dicarbonyl compounds of Formula XII (or their equivalent) with an aminopyrazole of Formula $XIII_1$ to give the desired heterocycles of Formula $IX_1$ Z is CH,

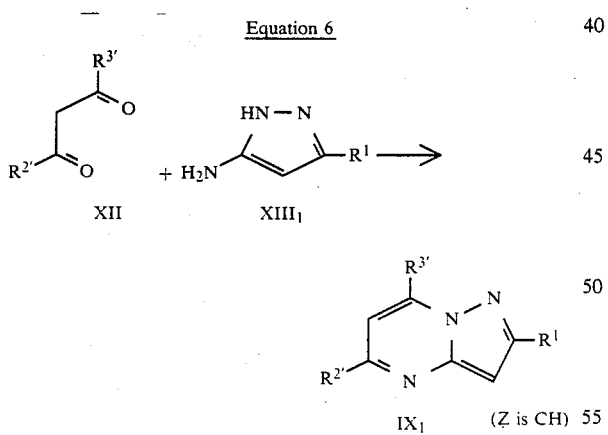

Equation 6

($IX_1$) (Z is CH)

wherein $R^1$ is as previously defined, $R^{2'}$ is H, $C_1$-$C_3$ alkyl or $C_1$-$C_2$ alkyl substituted with $OCH_3$, $SCH_3$ or CN; $R^{3'}$ is H or $CH_3$.

The reaction of Equation 6 is best carried out under the conditions taught by W. E. Kirkpatrick, et al., in *J. Med. Chem.,* 20, 386 (1977), J. S. Bajwa, et al., in *J. Chem. Soc. Perkin I.,* 3085 (1979) and B. M. Lynch, et al., in *Can. J. Chem.,* 53, 119 (1975).

Equation 7 illustrates the reaction of aminopyrazole of Formula $XIII_1$ with compounds of Formula XIV to give the desired heterocycles of Formula $IX_1$, Z is N.

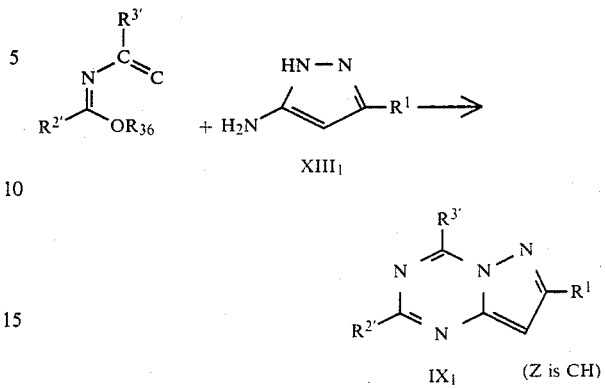

Equation 7

($IX_1$) (Z is CH)

wherein
$R^1$, $R^{2'}$, and $R^{3'}$ are as previously defined; and
$R_{36}$ is $C_1$-$C_4$ alkyl.

The reaction of Equation 7 is best carried out in an inert solvent such as toluene in the presence of an acid such as p-toluenesulfonic acid at a temperature between about 0° C. to 111° C. The products may be isolated by washing the reaction solution with an aqueous sodium carbonate solution, drying ($MgSO_4$) and concentrating the reaction solution. Crystallization and chromatography may be used for further purification of the products.

Equation 8 illustrates the reaction of aminopyrazole of Formula $XIII_1$, with an imidate of Formula XV to give the amidines of Formula XVI and the reaction of the amidines of Formula XVI with ortho esters of Formula XVII to give the desired heterocycles of Formula IX, Z is N.

Equation 8

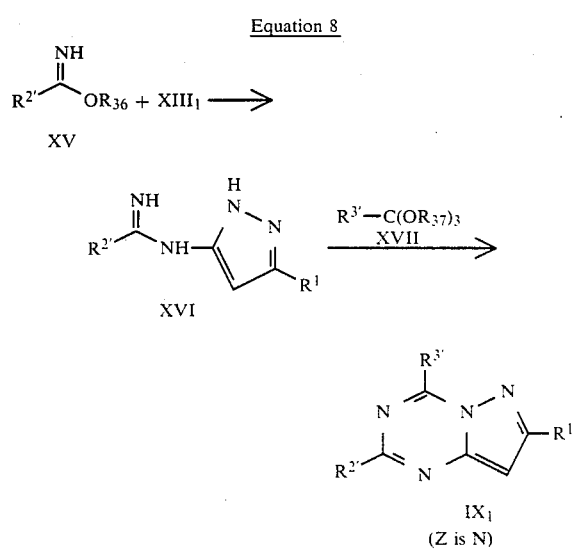

($IX_1$) (Z is N)

wherein
$R^1$, $R^{2'}$, and $R^{3'}$ and $R_{36}$ are as previously defined and $R_{37}$ is $C_1$-$C_4$ alkyl.

The reaction of Equation 8 is best carried out under the conditions taught by Keitara Senga, et al., in *J. Med. Chem.,* 25, 243 (1982).

Compounds of Formula $IX_1$ ($R^3$ is $OCH_3$) can be prepared as shown below in Equation 9 by reaction of chlorosubstituted heterocycles of Formula XVIII with methoxides of Formula XIX.

Equation 9

[Structure XVIII: pyrazole fused ring with Cl, Z, R², N, N-N, R¹ substituents] + M⁺ ⁻OCH₃ ⟶

XVIII          XIX

[Structure IX₁: pyrazole fused ring with OCH₃, Z, R², N, N-N, R¹ substituents]

(R³ is OCH₃)
IX₁ wherein R¹ and R² are as previously defined; M is Na or K.

The reaction of Equation 9 is best carried out in an inert solvent such as dimethylformamide or an alcohol. The products may be isolated by evaporating the reaction solution and washing the residue with water. Chromatography may be used for further purification of the products.

Compounds of Formula IX₁, (R² is R²″), can be prepared as shown below in Equation 10 by reacting chlorosubstituted heterocycles of Formula XX with nucleophiles of Formula ⁻R²″.

Equation 10

[Structure XX: pyrazole fused ring with R³, Z, Cl, N, N-N, R¹] + ⁻R²″ ⟶

XX

[Structure IX₁: pyrazole fused ring with R³, Z, R²″, N, N-N, R¹]

(R² is R²″)
IX₁ wherein R¹, R³, and Z are as previously defined; R²″ is C₁–C₃ alkoxy, or C₁–C₂ haloalkoxy.

The reaction of Equation 10 is best carried out in an inert solvent such as dimethylformamide or an alcohol. The products can be isolated by evaporating the reaction solvent and washing the residue with water. Chromatography may be used for further purification of the products.

Compounds XVIII and XX can be prepared from dichloroheterocycles of Formula XXI by nucleophilic displacement reactions with an appropriate nucleophile by methods in the art or by obvious modifications of these known methods.

[Structure XXI: pyrazole fused ring with Cl, Z, Cl, N, N-N, R¹]

XXI wherein
Z and R¹ are as previously defined.

Alternatively, they can be prepared by reacting the corresponding hydroxy compounds of Formula XXII or XXIII with POCl₃ or by other well-known methods or by obvious modification of these known methods.

[Structure XXII: pyrazole fused ring with OH, Z, R², N, N-N, R¹]

XXII

[Structure XXIII: pyrazole fused ring with R³, Z, HO, N, N-N, R¹]

XXIII wherein Z, R¹, R² and R³ are as previously defined.

Compounds XXI can be prepared by reacting the corresponding dihydroxy compounds of Formula XXIV with POCl₃ by methods well known in the art.

[Structure XXIV: pyrazole fused ring with OH, Z, HO, N, N-N, R¹]

XXIV wherein R¹ and Z are as previously defined.

The compounds XXII (Z is C—H). XXIII (Z is C—H) or XXIV (Z is C—H) can be prepared by condensation of a β-keto ester, a malonatediester or one of their equivalents with 3-amino-pyrazoles of Formula XIII, as taught by:
1. Yasuo Makisumi in *Chem. Pharm. Bull.*, 10, 612 (1962);
2. Keitara Senga et al. in *J. Med. Chem.*, 24 (5), 61a (1971);
3. Alfred Dornow and Klaus Dehmer in *Chem. Ber.*, 100 (8), 2577 (1967);
4. Mohamed Elnagdi in *Arch. Pharm.*, 316 (8), 713 (1983);
5. B. B. Gavrilenko in *Zh. Org. Khim.*, 18 (5), 1079 (1982);

or by modifications of these methods (e.g., reaction of 3-amino-pyrazoles of Formula XIII, with diketene).

The compounds XXII (Z is N), XXIII (Z is N) or XXIV (Z is N) can be similarly prepared by condensation of carbonylisocyanates of Formula XXV or the compounds of Formula XXVI with aminopyrazoles of Formula XIII₁.

$$\text{J}-\overset{\overset{\text{O}}{\|}}{\text{C}}-\text{N}=\text{C}=\text{O}$$

XXV

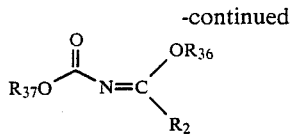 XXVI wherein
J is H, Cl, CH$_3$, C$_1$-C$_4$ alkoxy,
R$^2$, R$_{36}$ and R$_{37}$ are as previously defined.

The haloheterocycles of Formula X$_1$ can be synthesized by the same methods as those for the preparation of the heterocycles of Formula IX$_1$ using the aminohalopyrazoles of Formula XXVII$_1$ instead of the aminopyrazoles of Formula XIII$_1$ as starting material.

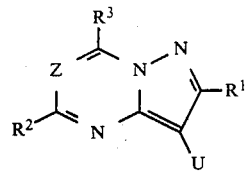 X$_1$

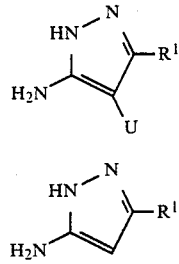 XXVII$_1$

XIII$_1$ wherein R$^1$, R$^2$, R$^3$, U and Z are as previously defined.

Alternatively, the haloheterocycles of Formula X$_1$ can be synthesized by halogenation of the heterocycles of Formula IX$_1$ with a halogenating agent such as bromine, N-bromosuccinimide, chlorine, N-chlorosuccinimide or iodine as shown in Equation 11.

Equation 11

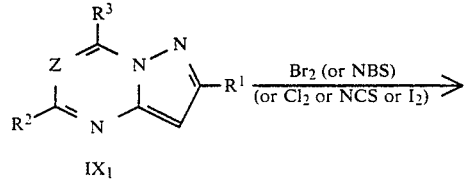

IX$_1$

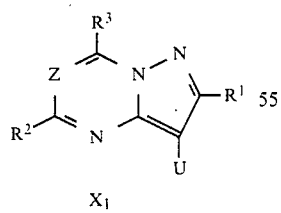

X$_1$ wherein R$^1$, R$^2$, R$^3$, Z and U are as previously defined.

The reaction of Equation 11 is best carried out in an inert solvent such as chloroform or carbon tetrachloride at a temperature between 0° C. to 77° C. The products can then be isolated by filtration, concentration of the filtrate and washing the residue with water. Crystallization or chromatography may be used for further purification if desired.

By similar methods as discussed for the preparation of the heterocycles of Formula IX$_1$ and the haloheterocycles of Formula X$_1$ from the aminopyrazoles of Formula XIII$_1$ and the aminohalopyrazoles of Formula XXVII$_1$, following compounds can be prepared:

The heterocycles of Formula IX$_2$ and the haloheterocycles of Formula X$_2$ can be prepared from the amino triazoles of Formula XIII$_2$ and the aminohalotriazoles of Formula XXVII$_2$;

The heterocycles of Formula IX$_3$ and the haloheterocycles of Formula X$_3$ can be prepared from the aminoimidazoles of Formula XIII$_3$ and the aminohaloimidazoles of Formula XXVII$_3$;

The heterocycles of Formula IX$_4$ and the haloheterocycles of Formula X$_4$ can be prepared from the N-aminoazoles of Formula XIII$_4$ and the N-aminohaloazoles of Formula XXVII$_4$;

The heterocycles of Formula IX$_5$ (where Z$^1$ is CH or CCH$_3$) and the haloheterocycles of Formula X$_5$ can be prepared from the N-aminoazoles of Formula XIII$_5$ (where Z$^1$ is CH or CCH$_3$) and the N-aminohaloazoles of Formula XXVII$_5$.

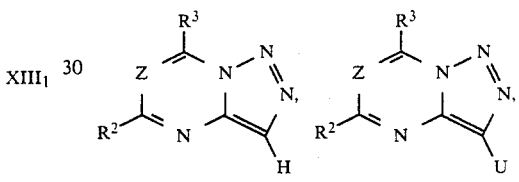

IX$_2$  X$_2$

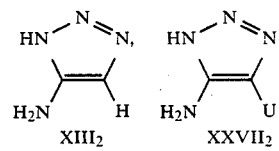

XIII$_2$  XXVII$_2$

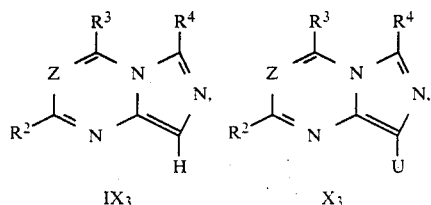

IX$_3$  X$_3$

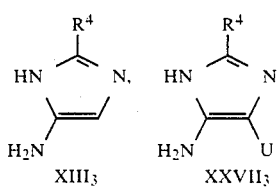

XIII$_3$  XXVII$_3$

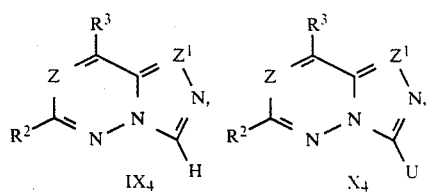

IX$_4$  X$_4$

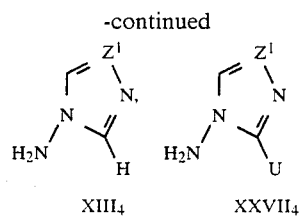

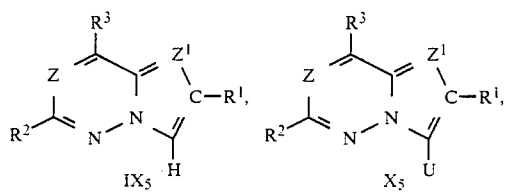

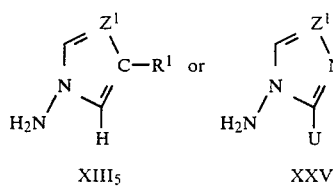

wherein $R^1$, $R^2$, $R^3$, $R^4$, Z and N are as previously defined.

The haloheterocycles of Formula $X_2$, $X_3$, $X_4$, and $X_5$, can also be prepared by halogenation of the heterocycles of Formula $IX_2$, $IX_3$, $IX_4$ and $IX_5$.

The heterocycles of Formula $IX_4$ ($Z^1$ is N,) can also be prepared by the reaction of compounds of Formula XXXXIII with orthoformate as shown below in Equation 12.

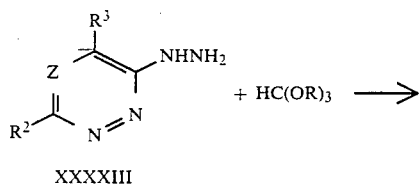

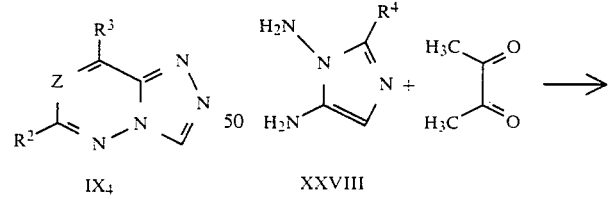

wherein
$R^2$, $R^3$ and Z are as previously defined and
R is lower alkyl.

The reaction of Equation 12 is best carried out in an inert solvent such as toluene at a temperature between about 0° C. to 120° C. The product can be isolated by evaporation of the reaction solvent and orthoformate. Crystallization of chromatography may be used for further purification of the products.

The heterocycles of Formula $IX_5$ ($Z_1$ is N,) can be prepared by the reaction of compounds of Formula XXXXIV with an α-halocarbonyl compound of Formula XXXXV as shown in Equation 13.

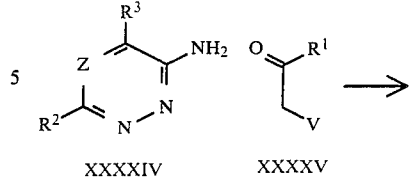

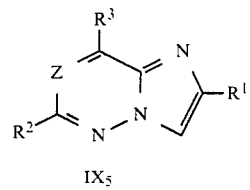

wherein $R^1$, $R^2$, $R^3$, Z and V are as previously defined.

The reaction of Equation 13 is best carried out in an inert solvent such as N,N-dimethylformamide at a temperature between about 0° C. to 160° C. The products can be isolated by evaporation of the reaction solvent and washing the residue with other solvent such as hexane or ether. Crystallization or chromatography may be used for further purification, if desired.

The heterocycles of Formula $IX_6$ can be prepared from compounds of Formula XXVIII. For example, reaction of some of the compounds of Formula XXVIII with 2,3-butadione gives the desired products of Formula $IX_6$ ($R_2$ is $CH_3$, $R_3$ is $CH_3$) as shown below in Equation 14.

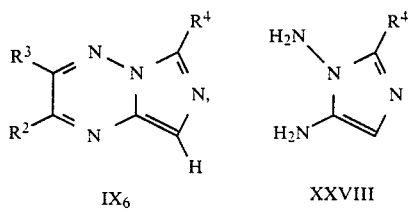

wherein $R^2$, $R^3$, and $R^4$ are as previously defined.

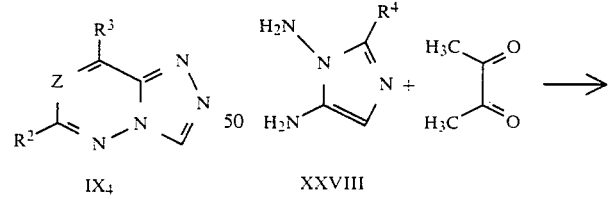

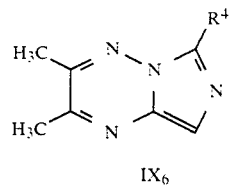

($R_2$ is $CH_3$, $R_3$ is $CH_3$)

wherein $R^4$ is as previously defined.

The reaction of Equation 14 is best carried out in an inert solvent such as toluene in the presence of an acid catalyst such as p-toluenesulfonic acid, if necessary, at a temperature between 0° C. and 120° C. The products may be isolated by evaporation of solvent, followed by chromatography or recrystallization of the residue.

The haloheterocycles of Formula $X_6$ can be synthesized by the same method as those for the preparation of the heterocycles of Formula $IX_6$ using the halocompounds of Formula XXIX instead of the compounds of Formula XXVIII as starting material.

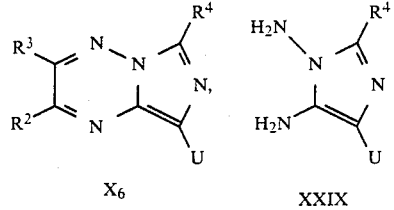

wherein $R^2$, $R^3$, $R^4$ and U are as previously defined.

Alternatively the haloheterocycles of Formula $X_6$ can be prepared by halogenation of the heterocycles of Formula $IX_6$ with a halogenating agent such as bromine, N-bromosuccinimide, chlorine, N-chlorosuccinimide or iodine.

The heterocycles of Formula $IX_7$ and the haloheterocycles of Formula $X_7$ can be synthesized from compounds of Formula XXX and Formula XXXI by the same methods as those for the preparation of compounds of Formula $IX_6$ and $X_6$ from compounds of Formula XXVIII and Formula XXIX.

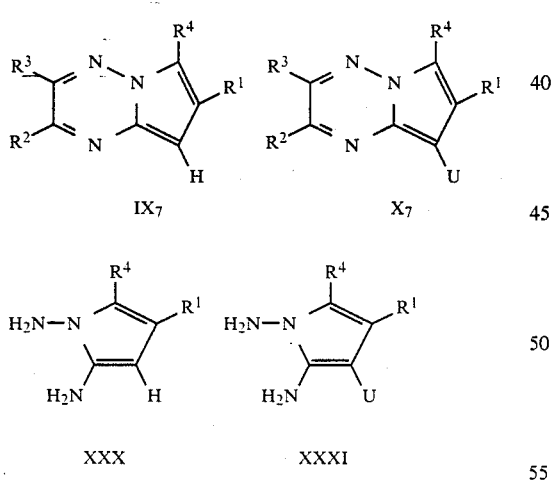

wherein $R^1$, $R^2$, $R^3$, $R^4$ and U are as previously defined.

The heterocycles of Formula $IX_{19}$ can be synthesized from the aminoheterocycles of Formula XXXII by similar methods as discussed for the preparation of the heterocycles of $IX_1$ from aminopyrazole of Formula $XIII_1$. For example, reaction of the aminoheterocycles of Formula XXXII with a β-dicarbonyl compound of Formula XXII should give the desired heterocycles of Formula $IX_{19}$ ($R^2$ is $R^{2'}$, $R^3$ is $R^{3'}$ and Z is C-H) as shown below in Equation 15.

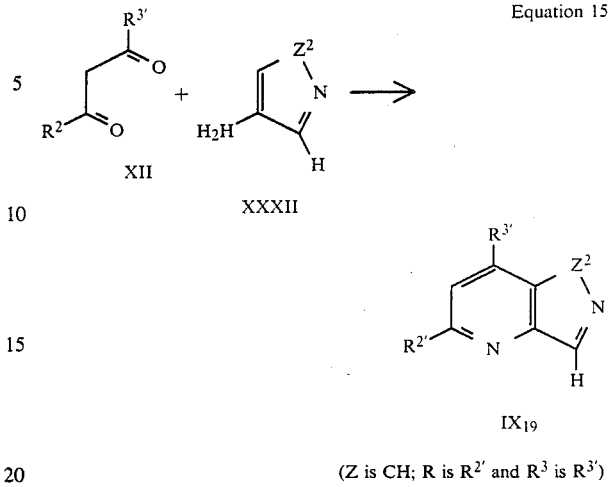

wherein $R^{2'}$, $R^{3'}$, and $Z^2$ are as previously defined.

The reaction of Equation 15 is best carried out under the conditions taught by A. Z. Britten, et al. in *Chem. Ind.*, 6, 278 (1973).

Reaction of compounds of Formula XXXIII with $HCO_2NH_4$ gives the desired heterocycles of Formula $IX_{19}$ (Z is N, $R^2$ is $CH_3$, $R^3$ is $CH_3$) as shown in Equation 16.

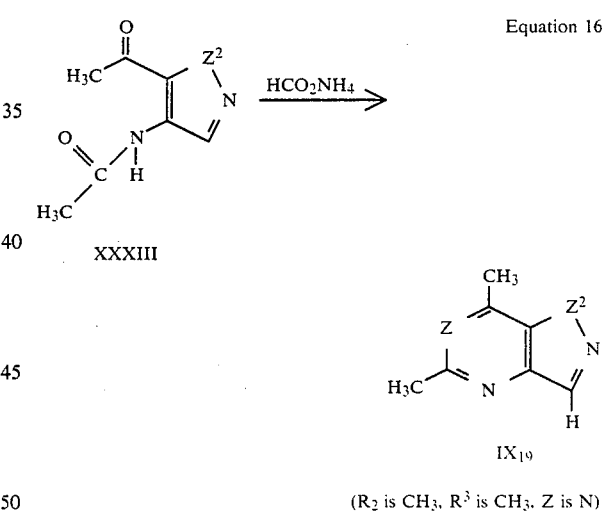

The reaction of Equation 14 is best carried out under the conditions taught by Guy Ah-Kon, et al., in *C. R. Acad. Sci., Ser. C.*, 278 (26), 1513 (1974).

The haloheterocycles of Formula $X_{19}$ can be synthesized from starting materials such as compounds of Formula XXXIV and XXXV in the same way as for the preparation of the heterocycles of Formula $IX_{19}$ from compounds of Formula XXXII and Formula XXXIII. Alternatively, compounds of Formula $IX_{19}$ can be converted to the haloheterocycles of Formula $X_{19}$ by halogenation.

The haloheterocycles of Formula $X_{20}$ can be prepared from starting materials such as compounds of Formula XXXVI and formula XXXVII by similar chemistry as taught previously for the preparation of heterocycles of Formula $IX_{19}$.

The heterocycles of Formula $IX_{20}$ can be synthesized by dehalogenating the haloheterocycles of Formula $X_{20}$.

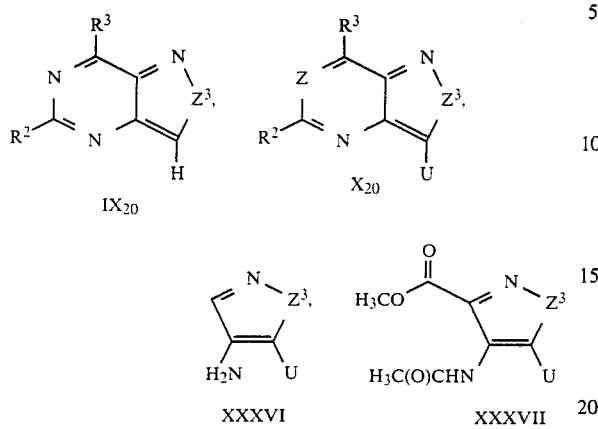

wherein $R^2$, $R^3$, Z, $Z^3$ and U are as previously defined.

The haloheterocycles of Formula $X_{14}$ can be prepared from compounds of Formula XXXVIII. For example, reaction of compounds of Formula XXXVIII with triethylorthoacetate gives the desired haloheterocycles of Formula $X_{14}$ ($R^2$ is $CH_3$) as shown in Equation 17.

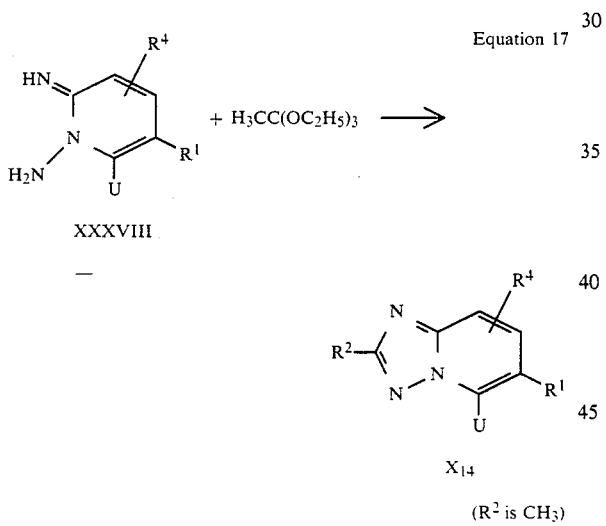

Equation 17 wherein $R^1$, $R^4$, and U are as previously defined.

The reaction of Equation 17 is best carried out in an inert solvent such as acetic acid at a temperature between 20° C. to 118° C. The products may be isolated by evaporation of the solvent, followed by chromatography or crystallization of the residue.

By similar methods as those described for the preparation of haloheterocycles of Formula $X_{14}$ from compounds of Formula XXXVIII, the following haloheterocycles can be prepared:

The haloheterocycles of Formula $X_{15}$ can be prepared from compounds of Formula XXXIX.

The haloheterocycles of Formula $X_{16}$ can be prepared from compounds of Formula XXXX.

The haloheterocycles of Formula $X_{17}$ can be prepared from compounds of Formula XXXXI.

The haloheterocycles of Formula $X_{18}$ can be prepared from the compounds of Formula XXXXII.

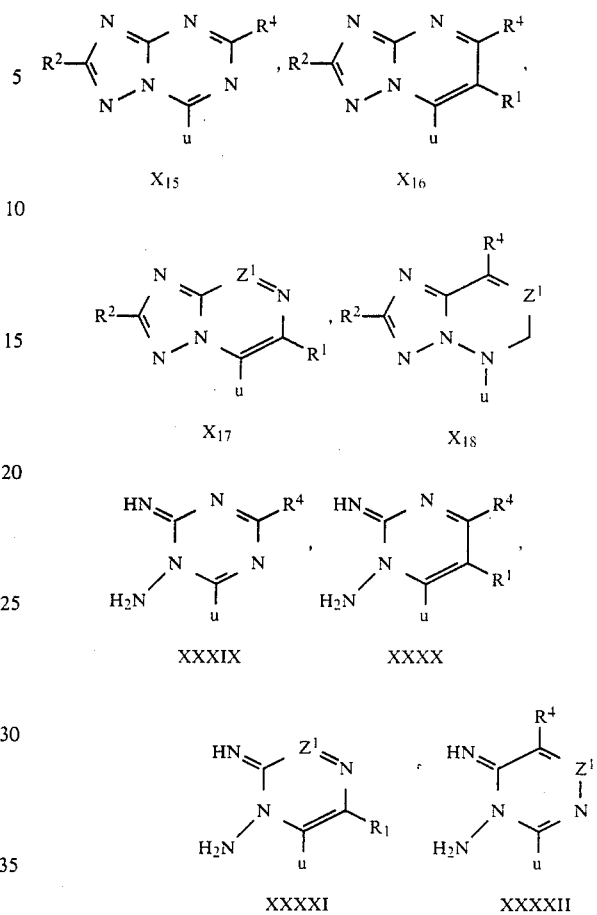

wherein $R^1$, $R^2$, $R^4$, $Z^1$ and U are as previously defined.

Heterocycles of Formula $IX_{10}$ can be synthesized by literature methods (or by modification of these methods) such as those taught by:

T. Tsuchiya, et al., in *Chem. Pharm. Bull.*, 31, 4568 (1983).

A. Kakehi, et al., in *J. Org. Chem.*, 42, 443 (1977).

T. Tsuchiya, et al., in *J. Chem. Soc., Chem. Commun.*, 1109 (1980).

A. Ohsawa, et al., in *J. Org. Chem.*, 47, 3497 (1982).

D. E. Kuhla, et al., in "Adv. Heterocycle Chem.", 21, 1-63 (1977).

U. Burger, et al., in *Helv. Chim. Acta.*, 62, 540 (1975).

A. Kakehi, et al., in *J. Org. Chem.*, 43, 4837 (1978).

G. Maury, et al., in *Chem. Heterocycl. Compd.*, 30, 179 (1977).

H. L. Blewitt in *Chem. Heterocycl. Compd.*, 30, 117 (1977).

T. Uchida, et al., in *Synthesis*, 209 (1976)

E. Kranz, et al., in Ger. Offen. 2220186 (published Nov. 8, 1973), Ger. Offen. 2058500 (published May 31, 1972) and in *Chem. Ber.*, 105 (1972)

The haloheterocycles of Formula $X_{10}$ can be synthesized by halogenating the heterocycles of Formula $IX_{10}$ with halogenating agents.

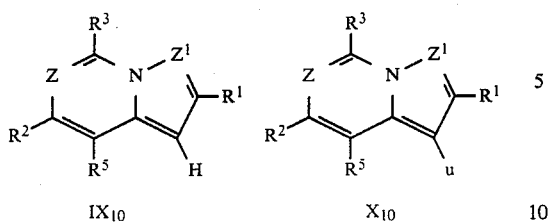 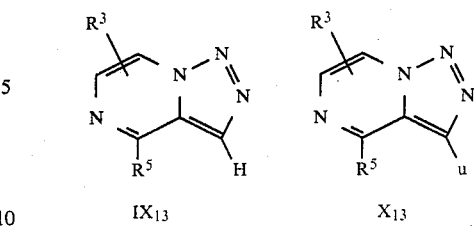

wherein $R^1$, $R^2$, $R^3$, $R^5$, Z, $Z^1$ and U are as previously defined.

The heterocycles of Formula $IX_{11}$ can be synthesized by literature methods (or by modification of these methods) such as those taught by K. Kasuga, et al., in *Yakugaka Zasshi.*, 94, 952 (1974), M. Muehlstaedt, et al., in *J. Prakt. Chem.*, 311, 363 (1969), and D. E. Kuhla, et al., in *Adv. Heterocycl. Chem.*, 21, (1977).

Jpn. Kokai 84/2053801 also describes the synthesis of some heterocycles of Formula $IX_{11}$. The haloheterocycles of Formula $X_{11}$ can be prepared by halogenating the heterocycles of Formula $IX_{11}$

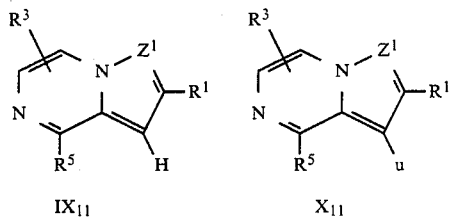

wherein $R^1$, $R^3$, Rhu 5, $Z^1$ and U are as previously defined.

The heterocycles of Formula $IX_{12}$ can be synthesized by literature methods (or by modification of these methods) such as those taught by G. Maury, et al., in *J. Heterocycl. Chem.*, 15, 1041 (1978), C. Wentrup in *Helv. Chim. Acta.*, 61, 1755 (1978), S. Mineo, et al., in *Synth. Commun.*, 6, 69 (1976) and Y. Tamura, et al., in *J. Heterocycl. Chem.*, 12, 481 (1975).

$X_{12}$ can be prepared by halogenation of the heterocycles of Formula $IX_{12}$ with halogenating agents.

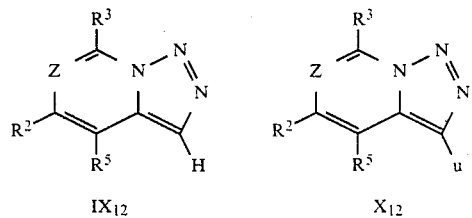

Heterocycles of Formula $IX_{13}$ can be synthesized by literature methods (or by modification of these methods) such as those taught by G. Maury, et al., in *Bull. Soc., Chim. Belg.*, 91, 153 (1982) and C. Wentrup in *Helv. Chim. Acta.*, 61, 1755 (1978). The haloheterocycles of Formula $X_{13}$ can be prepared by halogenation of the heterocycles of Formula $IX_{13}$.

The intermediates of Formula XII, $XIII_1$, XIV, XV, XXV, XXVI, $XXVII_1$, $XIII_2$, $XIII_3$, $XXVII_3$, $XIII_4$, $XXVII_4$, $XIII_5$, $XXVII_5$, XXVIII, XXIX, XXX, XXXI, XXXII, XXXIII, XXXIV, XXXV, XXXVI, XXXVII, XXXVIII, XXXIX, XXXX, XXXXI, XXXXII, XXXXIII, XXXXIV and XXXXV can be prepared by methods known in the art or by obvious modification of these known methods.

The synthesis of heterocyclic amines such as those represented by Formula III has been reviewed in "The Chemistry of Heterocyclic Compounds," a series published by Interscience Publ., New York and London. Aminopyrimidines are described by D. J. Brown in "The Pyrimidines," Vol. XVI of the series mentioned above which is herein incorporated by reference. The 2-amino-1,3,5-triazines of Formula III, where A is A-1 and $Z^4$ is N, can be prepared according to methods described by E. M. Smolin and L. Rappaport in "s-Triazines and Derivatives," Vol. XIII.

Pyrimidines of Formula III, where A is A-1 and Y is an acetal or thioacetal substituent, can be prepared by methods taught in European Patent Application No. 84,224 (published July 27, 1983).

Pyrimidines of Formula III, where A is A-1 and Y is cyclopropyl or $OCF_2H$ can be synthesized according to the methods taught in U.S. Pat. No. 4,515,626 and U.S. Pat. No. 4,540,782, respectively.

Compounds of Formula III, where A is A-2 or A-3, can be prepared by procedures disclosed in U.S. Pat. No. 4,339,267.

Compounds of Formula III, where A is A-4, can be prepared by methods taught in U.S. Pat. No. 4,487,626.

Additional references dealing with the synthesis ob bicyclic pyrimidines of Formula III, where A is A-2, A-3, or A-4 are Braker, Sheehan, Spitzmiller and Lott, *J. Am. Chem. Soc.*, 69, 3072 (1947); Mitler and Bhattacharya, *Quart. J. Indian Chem. Soc.*, 4, 152 (1927); Shrage and Hitchings, *J. Org. Chem.*, 16, 1153 (1951); Caldwell, Kornfeld annd Donnell, *J. Am. Chem. Soc.*, 63, 2188 (1941); and Fissekis, Myles and Brown, *J. Org. Chem.*, 29, 2670 (1964).

Compounds of Formula III, where A is A-5, can be prepared by methods taught in the U.S. Pat. No. 4,421,550.

Compounds of Formula III, where A is A-6, can be prepared by methods taught in the U.S. Pat. No. 4,496,392.

General Formulas For Tables

General Formula 1

-continued
General Formulas For Tables (L-2)SO₂NHC(=O)N(A-1)R    General Formula 2

(L-3)SO₂NHC(=O)N(A-1)R    General Formula 3

(L-4a)SO₂NHC(=O)N(A-1)R    General Formula 4a (L-4b)SO₂NHC(=O)N(A-1)R    General Formula 4b (L-5)SO₂NHC(=O)N(A-1)R    General Formula 5

(L-6)SO₂NHC(=O)N(A-1)R    General Formula 6

(L-7)SO₂NHC(=O)N(A-1)R    General Formula 7

(L-10)SO₂NHC(=O)N(A-1)R    General Formula 8

(L-11)SO₂NHC(=O)N(A-1)R    General Formula 9

(L-12)SO₂NHC(=O)N(A-1)R    General Formula 10

(L-13)SO₂NHC(=O)N(A-1)R    General Formula 11

(L-14)SO₂NHC(=O)N(A-1)R    General Formula 12

(L-15)SO₂NHC(=O)N(A-1)R    General Formula 13

(L-16)SO₂NHC(=O)N(A-1)R    General Formula 14

-continued
General Formulas For Tables (L-17)SO₂NHC(=O)N(A-1)R    General Formula 15

(L-18)SO₂NHC(=O)N(A-1)R    General Formula 16

(L-19)SO₂NHC(=O)N(A-1)R    General Formula 17

(L-20)SO₂NHC(=O)N(A-1)R    General Formula 18

TABLE 1

General Formula 1

| $R^1$ | $R^2$ | $R^3$ | R | X | Y | $Z^2$ |
|---|---|---|---|---|---|---|
| H | CH₃ | CH₃ | H | OCH₃ | OCH₃ | CH |
| H | CH₃ | CH₃ | H | OCH₃ | CH₃ | CH |
| H | CH₃ | CH₃ | H | Cl | OCH₃ | CH |
| H | CH₃ | CH₃ | H | CH₃ | CH₃ | CH |
| H | CH₃ | CH₃ | H | OCH₃ | OCH₃ | N |
| H | CH₃ | CH₃ | H | OCH₃ | CH₃ | N |
| H | CH₃ | CH₃ | H | OC₂H₅ | NHCH₃ | N |
| H | CH₃ | CH₃ | CH₃ | OCH₃ | CH₃ | N |
| Cl | CH₃ | CH₃ | H | OCH₃ | OCH₃ | CH |
| Cl | CH₃ | CH₃ | H | OCH₃ | CH₃ | CH |
| Cl | CH₃ | CH₃ | H | Cl | OCH₃ | CH |
| Cl | CH₃ | CH₃ | H | CH₃ | CH₃ | CH |
| Cl | CH₃ | CH₃ | H | OCH₃ | OCH₃ | N |
| Cl | CH₃ | CH₃ | H | OCH₃ | CH₃ | N |
| Cl | CH₃ | CH₃ | H | OC₂H₅ | NHCH₃ | N |
| Cl | CH₃ | CH₃ | CH₃ | OCH₃ | CH₃ | N |
| SO₂CH₃ | CH₃ | CH₃ | H | OCH₃ | OCH₃ | CH |
| SO₂CH₃ | CH₃ | CH₃ | H | OCH₃ | CH₃ | CH |
| SO₂CH₃ | CH₃ | CH₃ | H | Cl | OCH₃ | CH |
| SO₂CH₃ | CH₃ | CH₃ | H | CH₃ | CH₃ | CH |
| SO₂CH₃ | CH₃ | CH₃ | H | OCH₃ | OCH₃ | N |
| SO₂CH₃ | CH₃ | CH₃ | H | OCH₃ | CH₃ | N |
| SO₂CH₃ | CH₃ | CH₃ | H | OC₂H₅ | NHCH₃ | N |
| SO₂CH₃ | CH₃ | CH₃ | CH₃ | OCH₃ | CH₃ | N |
| SO₂N(CH₃)₂ | CH₃ | CH₃ | H | OCH₃ | OCH₃ | CH |
| SO₂N(CH₃)₂ | CH₃ | CH₃ | H | OCH₃ | CH₃ | CH |
| SO₂N(CH₃)₂ | CH₃ | CH₃ | H | Cl | OCH₃ | CH |
| SO₂N(CH₃)₂ | CH₃ | CH₃ | H | OCH₃ | OCH₃ | N |
| SO₂N(CH₃)₂ | CH₃ | CH₃ | H | OCH₃ | CH₃ | N |
| H | H | H | H | OCH₃ | OCH₃ | CH |
| H | H | H | H | OCH₃ | CH₃ | CH |
| H | H | H | H | Cl | OCH₃ | CH |
| H | H | H | H | CH₃ | CH₃ | CH |
| H | H | H | H | OCH₃ | OCH₃ | N |
| H | H | H | H | OCH₃ | CH₃ | N |
| H | H | H | H | OC₂H₅ | NHCH₃ | N |
| H | H | H | CH₃ | OCH₃ | CH₃ | N |
| Cl | H | H | H | OCH₃ | OCH₃ | CH |
| Cl | H | H | H | OCH₃ | CH₃ | CH |
| Cl | H | H | H | Cl | OCH₃ | CH |
| Cl | H | H | H | CH₃ | CH₃ | CH |
| Cl | H | H | H | OCH₃ | OCH₃ | N |
| Cl | H | H | H | OCH₃ | CH₃ | N |
| Cl | H | H | H | OC₂H₅ | NHCH₃ | N |
| Cl | H | H | CH₃ | OCH₃ | CH₃ | N |
| SO₂CH₃ | H | H | H | OCH₃ | OCH₃ | CH |
| SO₂CH₃ | H | H | H | OCH₃ | CH₃ | CH |
| SO₂CH₃ | H | H | H | Cl | OCH₃ | CH |
| SO₂CH₃ | H | H | H | CH₃ | CH₃ | CH |
| SO₂CH₃ | H | H | H | OCH₃ | OCH₃ | N |
| SO₂CH₃ | H | H | H | OCH₃ | CH₃ | N |
| SO₂CH₃ | H | H | H | OC₂H₅ | NHCH₃ | N |
| SO₂CH₃ | H | H | CH₃ | OCH₃ | CH₃ | N |
| SO₂N(CH₃)₂ | H | H | H | OCH₃ | OCH₃ | CH |

TABLE 1-continued

General Formula 1

| R¹ | R² | R³ | R | X | Y | Z⁴ |
|---|---|---|---|---|---|---|
| SO₂N(CH₃)₂ | H | H | H | OCH₃ | CH₃ | CH |
| SO₂N(CH₃)₂ | H | H | H | Cl | OCH₃ | CH |
| SO₂N(CH₃)₂ | H | H | H | OCH₃ | OCH₃ | N |
| SO₂N(CH₃)₂ | H | H | H | OCH₃ | CH₃ | N |
| H | H | CH₃ | H | OCH₃ | OCH₃ | CH |
| H | H | CH₃ | H | Cl | OCH₃ | CH |
| H | H | CH₃ | H | CH₃ | CH₃ | CH |
| H | H | CH₃ | H | OCH₃ | OCH₃ | N |
| H | H | CH₃ | H | OCH₃ | CH₃ | N |
| H | H | CH₃ | H | OC₂H₅ | NHCH₃ | N |
| H | H | CH₃ | H | OCH₃ | CH₃ | N |
| Cl | H | CH₃ | H | OCH₃ | OCH₃ | CH |
| Cl | H | CH₃ | H | OCH₃ | CH₃ | CH |
| Cl | H | CH₃ | H | Cl | OCH₃ | CH |
| Cl | H | CH₃ | H | CH₃ | CH₃ | CH |
| Cl | H | CH₃ | H | OCH₃ | OCH₃ | N |
| Cl | H | CH₃ | H | OCH₃ | CH₃ | N |
| Cl | H | CH₃ | H | OC₂H₅ | NHCH₃ | N |
| Cl | H | CH₃ | CH₃ | OCH₃ | CH₃ | N |
| CO₂CH₃ | H | CH₃ | H | OCH₃ | OCH₃ | CH |
| CO₂CH₃ | H | CH₃ | H | OCH₃ | CH₃ | CH |
| CO₂CH₃ | H | CH₃ | H | Cl | OCH₃ | CH |
| CO₂CH₃ | H | CH₃ | H | CH₃ | CH₃ | CH |
| CO₂CH₃ | H | CH₃ | H | OCH₃ | OCH₃ | N |
| CO₂CH₃ | H | CH₃ | H | OCH₃ | CH₃ | N |
| CO₂CH₃ | H | CH₃ | H | OC₂H₅ | NHCH₃ | N |
| CO₂CH₃ | H | CH₃ | CH₃ | OCH₃ | CH₃ | N |
| SO₂N(CH₃)₂ | H | CH₃ | H | OCH₃ | OCH₃ | CH |
| SO₂N(CH₃)₂ | H | CH₃ | H | OCH₃ | CH₃ | CH |
| SO₂N(CH₃)₂ | H | CH₃ | H | Cl | OCH₃ | CH |
| SO₂N(CH₃)₂ | H | CH₃ | H | OCH₃ | OCH₃ | N |
| SO₂N(CH₃)₂ | H | CH₃ | H | OCH₃ | CH₃ | N |
| H | CH₃ | H | H | OCH₃ | OCH₃ | CH |
| H | CH₃ | H | H | OCH₃ | CH₃ | CH |
| H | CH₃ | H | H | Cl | OCH₃ | CH |
| H | CH₃ | H | H | CH₃ | CH₃ | CH |
| H | CH₃ | H | H | OCH₃ | OCH₃ | N |
| H | CH₃ | H | H | OCH₃ | CH₃ | N |
| H | CH₃ | H | H | OC₂H₅ | NHCH₃ | N |
| H | CH₃ | H | CH₃ | OCH₃ | CH₃ | N |
| Cl | CH₃ | H | H | OCH₃ | OCH₃ | CH |
| Cl | CH₃ | H | H | OCH₃ | CH₃ | CH |
| Cl | CH₃ | H | H | Cl | OCH₃ | CH |
| Cl | CH₃ | H | H | CH₃ | CH₃ | CH |
| Cl | CH₃ | H | H | OCH₃ | OCH₃ | N |
| Cl | CH₃ | H | H | OCH₃ | CH₃ | N |
| Cl | CH₃ | H | H | OC₂H₅ | NHCH₃ | N |
| Cl | CH₃ | H | CH₃ | OCH₃ | CH₃ | N |
| SO₂CH₃ | CH₃ | H | H | OCH₃ | OCH₃ | CH |
| SO₂CH₃ | CH₃ | H | H | OCH₃ | CH₃ | CH |
| SO₂CH₃ | CH₃ | H | H | Cl | OCH₃ | CH |
| SO₂CH₃ | CH₃ | H | H | CH₃ | CH₃ | CH |
| SO₂CH₃ | CH₃ | H | H | OCH₃ | OCH₃ | N |
| SO₂CH₃ | CH₃ | H | H | OCH₃ | CH₃ | N |
| SO₂CH₃ | CH₃ | H | H | OC₂H₅ | NHCH₃ | N |
| SO₂CH₃ | CH₃ | H | CH₃ | OCH₃ | CH₃ | N |
| SO₂N(CH₃)₂ | CH₃ | H | H | OCH₃ | OCH₃ | CH |
| SO₂N(CH₃)₂ | CH₃ | H | H | OCH₃ | CH₃ | CH |
| SO₂N(CH₃)₂ | CH₃ | H | H | Cl | OCH₃ | CH |
| SO₂N(CH₃)₂ | CH₃ | H | H | OCH₃ | OCH₃ | N |
| SO₂N(CH₃)₂ | CH₃ | H | H | OCH₃ | CH₃ | N |
| CO₂CH₃ | CH₃ | CH₃ | H | OCH₃ | OCH₃ | CH |
| CO₂CH₃ | CH₃ | CH₃ | H | OCH₃ | CH₃ | CH |
| CO₂CH₃ | CH₃ | CH₃ | H | Cl | OCH₃ | CH |
| CO₂CH₃ | CH₃ | CH₃ | H | CH₃ | CH₃ | CH |
| CO₂CH₃ | CH₃ | CH₃ | H | OCH₃ | OCH₃ | N |
| CO₂CH₃ | CH₃ | CH₃ | H | OCH₃ | CH₃ | N |
| CO₂CH₃ | CH₃ | CH₃ | H | OC₂H₅ | NHCH₃ | N |
| CO₂CH₃ | CH₃ | CH₃ | CH₃ | OCH₃ | CH₃ | N |
| CO₂CH₃ | CH₃ | H | H | OCH₃ | OCH₃ | CH |
| CO₂CH₃ | CH₃ | H | H | OCH₃ | CH₃ | CH |
| CO₂CH₃ | CH₃ | H | H | Cl | OCH₃ | CH |
| CO₂CH₃ | CH₃ | H | H | CH₃ | CH₃ | CH |
| CO₂CH₃ | CH₃ | H | H | OCH₃ | OCH₃ | N |
| CO₂CH₃ | CH₃ | H | H | OCH₃ | CH₃ | N |
| CO₂CH₃ | CH₃ | H | H | OC₂H₅ | NHCH₃ | N |
| CO₂CH₃ | CH₃ | H | CH₃ | OCH₃ | CH₃ | N |
| CO₂CH₃ | H | CH₃ | H | OCH₃ | OCH₃ | CH |
| CO₂CH₃ | H | CH₃ | H | OCH₃ | CH₃ | CH |
| CO₂CH₃ | H | CH₃ | H | Cl | OCH₃ | CH |
| CO₂CH₃ | H | CH₃ | H | CH₃ | CH₃ | CH |
| CO₂CH₃ | H | CH₃ | H | OCH₃ | OCH₃ | N |
| CO₂CH₃ | H | CH₃ | H | OCH₃ | CH₃ | N |
| CO₂CH₃ | H | CH₃ | H | OC₂H₅ | NHCH₃ | N |
| CO₂CH₃ | H | CH₃ | CH₃ | OCH₃ | CH₃ | N |

TABLE 2

General Formula 2

| Z | R² | R³ | R | X | Y | Z⁴ |
|---|---|---|---|---|---|---|
| CH | CH₃ | CH₃ | H | OCH₃ | OCH₃ | CH |
| CH | CH₃ | CH₃ | H | OCH₃ | CH₃ | CH |
| CH | CH₃ | CH₃ | H | Cl | OCH₃ | CH |
| CH | CH₃ | CH₃ | H | CH₃ | CH₃ | CH |
| CH | CH₃ | CH₃ | H | OCH₃ | OCH₃ | N |
| CH | CH₃ | CH₃ | H | OCH₃ | CH₃ | N |
| CH | CH₃ | CH₃ | H | OC₂H₅ | NHCH₃ | N |
| CH | CH₃ | CH₃ | CH₃ | OCH₃ | CH₃ | N |
| N | CH₃ | CH₃ | H | OCH₃ | OCH₃ | CH |
| N | CH₃ | CH₃ | H | OCH₃ | CH₃ | CH |
| N | CH₃ | CH₃ | H | Cl | OCH₃ | CH |
| N | CH₃ | CH₃ | H | CH₃ | CH₃ | CH |
| N | CH₃ | CH₃ | H | OCH₃ | OCH₃ | N |
| N | CH₃ | CH₃ | H | OCH₃ | CH₃ | N |
| N | CH₃ | CH₃ | H | OC₂H₅ | NHCH₃ | N |
| N | CH₃ | CH₃ | CH₃ | OCH₃ | CH₃ | N |
| CH | CH₃ | H | H | OCH₃ | OCH₃ | CH |
| CH | CH₃ | H | H | OCH₃ | CH₃ | CH |
| CH | CH₃ | H | H | Cl | OCH₃ | CH |
| CH | CH₃ | H | H | CH₃ | CH₃ | CH |
| CH | CH₃ | H | H | OCH₃ | OCH₃ | N |
| CH | CH₃ | H | H | OCH₃ | CH₃ | N |
| CH | CH₃ | H | H | OC₂H₅ | NHCH₃ | N |
| CH | CH₃ | H | CH₃ | OCH₃ | CH₃ | N |
| N | CH₃ | H | H | OCH₃ | OCH₃ | CH |
| N | CH₃ | H | H | OCH₃ | CH₃ | CH |
| N | CH₃ | H | H | Cl | OCH₃ | CH |
| N | CH₃ | H | H | CH₃ | CH₃ | CH |
| N | CH₃ | H | H | OCH₃ | OCH₃ | N |
| N | CH₃ | H | H | OCH₃ | CH₃ | N |
| N | CH₃ | H | H | OC₂H₅ | NHCH₃ | N |
| N | CH₃ | H | CH₃ | OCH₃ | CH₃ | N |
| CH | H | CH₃ | H | OCH₃ | OCH₃ | CH |
| CH | H | CH₃ | H | OCH₃ | CH₃ | CH |
| CH | H | CH₃ | H | Cl | OCH₃ | CH |
| CH | H | CH₃ | H | CH₃ | CH₃ | CH |
| CH | H | CH₃ | H | OCH₃ | OCH₃ | N |
| CH | H | CH₃ | H | OCH₃ | CH₃ | N |
| CH | H | CH₃ | H | OC₂H₅ | NHCH₃ | N |
| CH | H | CH₃ | CH₃ | OCH₃ | CH₃ | N |
| N | H | CH₃ | H | OCH₃ | OCH₃ | CH |
| N | H | CH₃ | H | OCH₃ | CH₃ | CH |
| N | H | CH₃ | H | Cl | OCH₃ | CH |
| N | H | CH₃ | H | CH₃ | CH₃ | CH |
| N | H | CH₃ | H | OCH₃ | OCH₃ | N |
| N | H | CH₃ | H | OCH₃ | CH₃ | N |
| N | H | CH₃ | H | OC₂H₅ | NHCH₃ | N |
| N | H | CH₃ | CH₃ | OCH₃ | CH₃ | N |
| CH | H | H | H | OCH₃ | OCH₃ | CH |
| CH | H | H | H | OCH₃ | CH₃ | CH |
| CH | H | H | H | Cl | OCH₃ | CH |
| CH | H | H | H | CH₃ | CH₃ | CH |
| CH | H | H | H | OCH₃ | OCH₃ | N |
| CH | H | H | H | OCH₃ | CH₃ | N |
| CH | H | H | H | OC₂H₅ | NHCH₃ | N |
| CH | H | H | CH₃ | OCH₃ | CH₃ | N |
| N | H | H | H | OCH₃ | OCH₃ | CH |
| N | H | H | H | OCH₃ | CH₃ | CH |
| N | H | H | H | Cl | OCH₃ | CH |
| N | H | H | H | CH₃ | CH₃ | CH |
| N | H | H | H | OCH₃ | OCH₃ | N |
| N | H | H | H | OCH₃ | CH₃ | N |
| N | H | H | H | OC₂H₅ | NHCH₃ | N |
| N | H | H | CH₃ | OCH₃ | CH₃ | N |

TABLE 3

General Formula 3

| R² | R³ | R⁴ | R | X | Y | Z⁴ |
|---|---|---|---|---|---|---|
| CH₃ | CH₃ | H | H | OCH₃ | OCH₃ | CH |
| CH₃ | CH₃ | H | H | OCH₃ | CH₃ | CH |
| CH₃ | CH₃ | H | H | Cl | OCH₃ | CH |
| CH₃ | CH₃ | H | H | CH₃ | CH₃ | CH |
| CH₃ | CH₃ | H | H | OCH₃ | OCH₃ | N |
| CH₃ | CH₃ | H | H | OC₂H₅ | NHCH₃ | N |
| CH₃ | CH₃ | H | CH₃ | OCH₃ | CH₃ | N |
| CH₃ | H | H | H | OCH₃ | OCH₃ | CH |
| CH₃ | H | H | H | OCH₃ | CH₃ | CH |
| CH₃ | H | H | H | Cl | OCH₃ | CH |
| CH₃ | H | H | H | CH₃ | CH₃ | CH |
| CH₃ | H | H | H | OCH₃ | OCH₃ | N |
| CH₃ | H | H | H | OCH₃ | CH₃ | N |
| CH₃ | H | H | H | OC₂H₅ | NHCH₃ | N |
| CH₃ | H | H | CH₃ | OCH₃ | CH₃ | N |
| H | CH₃ | H | H | OCH₃ | OCH₃ | CH |
| H | CH₃ | H | H | OCH₃ | CH₃ | CH |
| H | CH₃ | H | H | Cl | OCH₃ | CH |
| H | CH₃ | H | H | CH₃ | CH₃ | CH |
| H | CH₃ | H | H | OCH₃ | OCH₃ | N |
| H | CH₃ | H | H | OCH₃ | CH₃ | N |
| H | CH₃ | H | H | OC₂H₅ | NHCH₃ | N |
| H | CH₃ | H | CH₃ | OCH₃ | CH₃ | N |
| H | H | H | H | OCH₃ | OCH₃ | CH |
| H | H | H | H | OCH₃ | CH₃ | CH |
| H | H | H | H | Cl | OCH₃ | CH |
| H | H | H | H | CH₃ | CH₃ | CH |
| H | H | H | H | OCH₃ | OCH₃ | N |
| H | H | H | H | OCH₃ | CH₃ | N |
| H | H | H | H | OC₂H₅ | NHCH₃ | N |
| H | H | H | CH₃ | OCH₃ | CH₃ | N |

TABLE 4a

General Formula 4a

| Z¹ | R² | R³ | R | X | Y | Z⁴ |
|---|---|---|---|---|---|---|
| CH | CH₃ | CH₃ | H | OCH₃ | OCH₃ | CH |
| CH | CH₃ | CH₃ | H | OCH₃ | CH₃ | CH |
| CH | CH₃ | CH₃ | H | Cl | OCH₃ | CH |
| CH | CH₃ | CH₃ | H | CH₃ | CH₃ | CH |
| CH | CH₃ | CH₃ | H | OCH₃ | OCH₃ | N |
| CH | CH₃ | CH₃ | H | OCH₃ | CH₃ | N |
| CH | CH₃ | CH₃ | H | OC₂H₅ | NHCH₃ | N |
| CH | CH₃ | CH₃ | CH₃ | OCH₃ | CH₃ | N |
| N | CH₃ | CH₃ | H | OCH₃ | OCH₃ | CH |
| N | CH₃ | CH₃ | H | OCH₃ | CH₃ | CH |
| N | CH₃ | CH₃ | H | Cl | OCH₃ | CH |
| N | CH₃ | CH₃ | H | CH₃ | CH₃ | CH |
| N | CH₃ | CH₃ | H | OCH₃ | OCH₃ | N |
| N | CH₃ | CH₃ | H | OCH₃ | CH₃ | N |
| N | CH₃ | CH₃ | H | OC₂H₅ | NHCH₃ | N |
| N | CH₃ | CH₃ | CH₃ | OCH₃ | CH₃ | N |
| CH | H | H | H | OCH₃ | OCH₃ | CH |

TABLE 4a-continued

General Formula 4a

| Z¹ | R² | R³ | R | X | Y | Z⁴ |
|---|---|---|---|---|---|---|
| CH | H | H | H | OCH₃ | CH₃ | CH |
| CH | H | H | H | Cl | OCH₃ | CH |
| CH | H | H | H | CH₃ | CH₃ | CH |
| CH | H | H | H | OCH₃ | OCH₃ | N |
| CH | H | H | H | OCH₃ | CH₃ | N |
| CH | H | H | H | OC₂H₅ | NHCH₃ | N |
| CH | H | H | CH₃ | OCH₃ | CH₃ | N |
| N | H | H | H | OCH₃ | OCH₃ | CH |
| N | H | H | H | OCH₃ | CH₃ | CH |
| N | H | H | H | Cl | OCH₃ | CH |
| N | H | H | H | CH₃ | CH₃ | CH |
| N | H | H | H | OCH₃ | OCH₃ | N |
| N | H | H | H | OCH₃ | CH₃ | N |
| N | H | H | H | OC₂H₅ | NHCH₃ | N |
| N | H | H | CH₃ | OCH₃ | CH₃ | N |

TABLE 4b

General Formula 4b

| R² | R³ | R | X | Y | Z⁴ |
|---|---|---|---|---|---|
| CH₃ | CH₃ | H | OCH₃ | OCH₃ | CH |
| CH₃ | CH₃ | H | OCH₃ | CH₃ | CH |
| CH₃ | CH₃ | H | Cl | OCH₃ | CH |
| CH₃ | CH₃ | H | CH₃ | CH₃ | CH |
| CH₃ | CH₃ | H | OCH₃ | OCH₃ | N |
| CH₃ | CH₃ | H | OCH₃ | CH₃ | N |
| CH₃ | CH₃ | H | OC₂H₅ | NHCH₃ | N |
| CH₃ | CH₃ | CH₃ | OCH₃ | CH₃ | N |
| CH₃ | H | H | OCH₃ | OCH₃ | CH |
| CH₃ | H | H | OCH₃ | CH₃ | CH |
| CH₃ | H | H | Cl | OCH₃ | CH |
| CH₃ | H | H | CH₃ | CH₃ | CH |
| CH₃ | H | H | OCH₃ | OCH₃ | N |
| CH₃ | H | H | OCH₃ | CH₃ | N |
| CH₃ | H | H | OC₂H₅ | NHCH₃ | N |
| CH₃ | H | CH₃ | OCH₃ | CH₃ | N |
| H | CH₃ | H | OCH₃ | OCH₃ | CH |
| H | CH₃ | H | OCH₃ | CH₃ | CH |
| H | CH₃ | H | Cl | OCH₃ | CH |
| H | CH₃ | H | CH₃ | CH₃ | CH |
| H | CH₃ | H | OCH₃ | OCH₃ | N |
| H | CH₃ | H | OCH₃ | CH₃ | N |
| H | CH₃ | H | OC₂H₅ | NHCH₃ | N |
| H | CH₃ | CH₃ | OCH₃ | CH₃ | N |
| H | H | H | OCH₃ | OCH₃ | CH |
| H | H | H | OCH₃ | CH₃ | CH |
| H | H | H | Cl | OCH₃ | CH |
| H | H | H | CH₃ | CH₃ | CH |
| H | H | H | OCH₃ | OCH₃ | N |
| H | H | H | OCH₃ | CH₃ | N |
| H | H | H | OC₂H₅ | NHCH₃ | N |
| H | H | CH₃ | OCH₃ | CH₃ | N |

TABLE 5

General Formula 5

| Z¹ | R¹ | R² | R³ | R | X | Y | Z⁴ |
|---|---|---|---|---|---|---|---|
| CH | H | CH₃ | CH₃ | H | OCH₃ | OCH₃ | CH |
| CH | H | CH₃ | CH₃ | H | OCH₃ | CH₃ | CH |
| CH | H | CH₃ | CH₃ | H | Cl | OCH₃ | CH |
| CH | H | CH₃ | CH₃ | H | CH₃ | CH₃ | CH |
| CH | H | CH₃ | CH₃ | H | OCH₃ | OCH₃ | N |
| CH | H | CH₃ | CH₃ | H | OCH₃ | CH₃ | N |
| CH | H | CH₃ | CH₃ | H | OC₂H₅ | NHCH₃ | N |
| CH | H | CH₃ | CH₃ | CH₃ | OCH₃ | CH₃ | N |
| CH | Cl | CH₃ | CH₃ | H | OCH₃ | OCH₃ | CH |
| CH | Cl | CH₃ | CH₃ | H | OCH₃ | CH₃ | CH |
| CH | Cl | CH₃ | CH₃ | H | Cl | OCH₃ | CH |
| CH | Cl | CH₃ | CH₃ | H | CH₃ | CH₃ | CH |
| CH | Cl | CH₃ | CH₃ | H | OCH₃ | OCH₃ | N |
| CH | Cl | CH₃ | CH₃ | H | OCH₃ | CH₃ | N |
| CH | Cl | CH₃ | CH₃ | H | OC₂H₅ | NHCH₃ | N |
| CH | Cl | CH₃ | CH₃ | CH₃ | OCH₃ | CH₃ | N |
| CH | SO₂CH₃ | CH₃ | CH₃ | H | OCH₃ | OCH₃ | CH |
| CH | SO₂CH₃ | CH₃ | CH₃ | H | OCH₃ | CH₃ | CH |
| CH | SO₂CH₃ | CH₃ | CH₃ | H | Cl | OCH₃ | CH |

TABLE 5-continued

General Formula 5

| $Z^1$ | $R^1$ | $R^2$ | $R^3$ | R | X | Y | $Z^4$ |
|---|---|---|---|---|---|---|---|
| CH | SO$_2$CH$_3$ | CH$_3$ | CH$_3$ | H | CH$_3$ | CH$_3$ | CH |
| CH | SO$_2$CH$_3$ | CH$_3$ | CH$_3$ | H | OCH$_3$ | OCH$_3$ | N |
| CH | SO$_2$CH$_3$ | CH$_3$ | CH$_3$ | H | OCH$_3$ | CH$_3$ | N |
| CH | SO$_2$CH$_3$ | CH$_3$ | CH$_3$ | H | OC$_2$H$_5$ | NHCH$_3$ | N |
| CH | SO$_2$CH$_3$ | CH$_3$ | CH$_3$ | CH$_3$ | OCH$_3$ | CH$_3$ | N |
| CH | SO$_2$N(CH$_3$)$_2$ | CH$_3$ | CH$_3$ | H | OCH$_3$ | OCH$_3$ | CH |
| CH | SO$_2$N(CH$_3$)$_2$ | CH$_3$ | CH$_3$ | H | OCH$_3$ | CH$_3$ | CH |
| CH | SO$_2$N(CH$_3$)$_2$ | CH$_3$ | CH$_3$ | H | Cl | OCH$_3$ | CH |
| CH | SO$_2$N(CH$_3$)$_2$ | CH$_3$ | CH$_3$ | H | OCH$_3$ | OCH$_3$ | N |
| CH | SO$_2$N(CH$_3$)$_2$ | CH$_3$ | CH$_3$ | H | OCH$_3$ | CH$_3$ | N |
| CH | H | H | H | H | OCH$_3$ | OCH$_3$ | CH |
| CH | H | H | H | H | OCH$_3$ | CH$_3$ | CH |
| CH | H | H | H | H | Cl | OCH$_3$ | CH |
| CH | H | H | H | H | CH$_3$ | CH$_3$ | CH |
| CH | H | H | H | H | OCH$_3$ | OCH$_3$ | N |
| CH | H | H | H | H | OCH$_3$ | CH$_3$ | N |
| CH | H | H | H | H | OC$_2$H$_5$ | NHCH$_3$ | N |
| CH | H | H | H | CH$_3$ | OCH$_3$ | CH$_3$ | N |
| CH | Cl | H | H | H | OCH$_3$ | OCH$_3$ | CH |
| CH | Cl | H | H | H | OCH$_3$ | CH$_3$ | CH |
| CH | Cl | H | H | H | Cl | OCH$_3$ | CH |
| CH | Cl | H | H | H | CH$_3$ | CH$_3$ | CH |
| CH | Cl | H | H | H | OCH$_3$ | OCH$_3$ | N |
| CH | Cl | H | H | H | OCH$_3$ | CH$_3$ | N |
| CH | Cl | H | H | H | OC$_2$H$_5$ | NHCH$_3$ | N |
| CH | Cl | H | H | CH$_3$ | OCH$_3$ | CH$_3$ | N |
| CH | SO$_2$CH$_3$ | H | H | H | OCH$_3$ | OCH$_3$ | CH |
| CH | SO$_2$CH$_3$ | H | H | H | OCH$_3$ | CH$_3$ | CH |
| CH | SO$_2$CH$_3$ | H | H | H | Cl | OCH$_3$ | CH |
| CH | SO$_2$CH$_3$ | H | H | H | CH$_3$ | CH$_3$ | CH |
| CH | SO$_2$CH$_3$ | H | H | H | OCH$_3$ | OCH$_3$ | N |
| CH | SO$_2$CH$_3$ | H | H | H | OCH$_3$ | CH$_3$ | N |
| CH | SO$_2$CH$_3$ | H | H | H | OC$_2$H$_5$ | NHCH$_3$ | N |
| CH | SO$_2$CH$_3$ | H | H | CH$_3$ | OCH$_3$ | CH$_3$ | N |
| CH | SO$_2$N(CH$_3$)$_2$ | H | H | H | OCH$_3$ | OCH$_3$ | CH |
| CH | SO$_2$N(CH$_3$)$_2$ | H | H | H | OCH$_3$ | CH$_3$ | CH |
| CH | SO$_2$N(CH$_3$)$_2$ | H | H | H | Cl | OCH$_3$ | CH |
| CH | SO$_2$N(CH$_3$)$_2$ | H | H | H | OCH$_3$ | OCH$_3$ | N |
| CH | SO$_2$N(CH$_3$)$_2$ | H | H | H | OCH$_3$ | CH$_3$ | N |
| CH | H | H | CH$_3$ | H | OCH$_3$ | OCH$_3$ | CH |
| CH | H | H | CH$_3$ | H | OCH$_3$ | CH$_3$ | CH |
| CH | H | H | CH$_3$ | H | Cl | OCH$_3$ | CH |
| CH | H | H | CH$_3$ | H | CH$_3$ | CH$_3$ | CH |
| CH | H | H | CH$_3$ | H | OCH$_3$ | OCH$_3$ | N |
| CH | H | H | CH$_3$ | H | OCH$_3$ | CH$_3$ | N |
| CH | H | H | CH$_3$ | H | OC$_2$H$_5$ | NHCH$_3$ | N |
| CH | H | H | CH$_3$ | CH$_3$ | OCH$_3$ | CH$_3$ | N |
| CH | Cl | H | CH$_3$ | H | OCH$_3$ | OCH$_3$ | CH |
| CH | Cl | H | CH$_3$ | H | OCH$_3$ | CH$_3$ | CH |
| CH | Cl | H | CH$_3$ | H | Cl | OCH$_3$ | CH |
| CH | Cl | H | CH$_3$ | H | CH$_3$ | CH$_3$ | CH |
| CH | Cl | H | CH$_3$ | H | OCH$_3$ | OCH$_3$ | N |
| CH | Cl | H | CH$_3$ | H | OCH$_3$ | CH$_3$ | N |
| CH | Cl | H | CH$_3$ | H | OC$_2$H$_5$ | NHCH$_3$ | N |
| CH | Cl | H | CH$_3$ | CH$_3$ | OCH$_3$ | CH$_3$ | N |
| CH | SO$_2$CH$_3$ | H | CH$_3$ | H | OCH$_3$ | OCH$_3$ | CH |
| CH | SO$_2$CH$_3$ | H | CH$_3$ | H | OCH$_3$ | CH$_3$ | CH |
| CH | SO$_2$CH$_3$ | H | CH$_3$ | H | Cl | OCH$_3$ | CH |
| CH | SO$_2$CH$_3$ | H | CH$_3$ | H | CH$_3$ | CH$_3$ | CH |
| CH | SO$_2$CH$_3$ | H | CH$_3$ | H | OCH$_3$ | OCH$_3$ | N |
| CH | SO$_2$CH$_3$ | H | CH$_3$ | H | OCH$_3$ | CH$_3$ | N |
| CH | SO$_2$CH$_3$ | H | CH$_3$ | H | OC$_2$H$_5$ | NHCH$_3$ | N |
| CH | SO$_2$CH$_3$ | H | CH$_3$ | CH$_3$ | OCH$_3$ | CH$_3$ | N |
| CH | SO$_2$N(CH$_3$)$_2$ | H | CH$_3$ | H | OCH$_3$ | OCH$_3$ | CH |
| CH | SO$_2$N(CH$_3$)$_2$ | H | CH$_3$ | H | OCH$_3$ | CH$_3$ | CH |
| CH | SO$_2$N(CH$_3$)$_2$ | H | CH$_3$ | H | Cl | OCH$_3$ | CH |
| CH | SO$_2$N(CH$_3$)$_2$ | H | CH$_3$ | H | OCH$_3$ | OCH$_3$ | N |
| CH | SO$_2$N(CH$_3$)$_2$ | H | CH$_3$ | H | OCH$_3$ | CH$_3$ | N |
| CH | H | CH$_3$ | H | H | OCH$_3$ | OCH$_3$ | CH |
| CH | H | CH$_3$ | H | H | OCH$_3$ | CH$_3$ | CH |
| CH | H | CH$_3$ | H | H | Cl | OCH$_3$ | CH |
| CH | H | CH$_3$ | H | H | CH$_3$ | CH$_3$ | CH |
| CH | H | CH$_3$ | H | H | OCH$_3$ | OCH$_3$ | N |
| CH | H | CH$_3$ | H | H | OCH$_3$ | CH$_3$ | N |
| CH | H | CH$_3$ | H | H | OC$_2$H$_5$ | NHCH$_3$ | N |
| CH | H | CH$_3$ | H | CH$_3$ | OCH$_3$ | CH$_3$ | N |
| CH | Cl | CH$_3$ | H | H | OCH$_3$ | OCH$_3$ | CH |
| CH | Cl | CH$_3$ | H | H | OCH$_3$ | CH$_3$ | CH |
| CH | Cl | CH$_3$ | H | H | Cl | OCH$_3$ | CH |
| CH | Cl | CH$_3$ | H | H | CH$_3$ | CH$_3$ | CH |

TABLE 5-continued

General Formula 5

| $Z^1$ | $R^1$ | $R^2$ | $R^3$ | R | X | Y | $Z^4$ |
|---|---|---|---|---|---|---|---|
| CH | Cl | $CH_3$ | H | H | $OCH_3$ | $OCH_3$ | N |
| CH | Cl | $CH_3$ | H | H | $OCH_3$ | $CH_3$ | N |
| CH | Cl | $CH_3$ | H | H | $OC_2H_5$ | $NHCH_3$ | N |
| CH | Cl | $CH_3$ | H | $CH_3$ | $OCH_3$ | $CH_3$ | N |
| CH | $SO_2CH_3$ | $CH_3$ | H | H | $OCH_3$ | $OCH_3$ | CH |
| CH | $SO_2CH_3$ | $CH_3$ | H | H | $OCH_3$ | $CH_3$ | CH |
| CH | $SO_2CH_3$ | $CH_3$ | H | H | Cl | $OCH_3$ | CH |
| CH | $SO_2CH_3$ | $CH_3$ | H | H | $CH_3$ | $CH_3$ | CH |
| CH | $SO_2CH_3$ | $CH_3$ | H | H | $OCH_3$ | $OCH_3$ | N |
| CH | $SO_2CH_3$ | $CH_3$ | H | H | $OCH_3$ | $CH_3$ | N |
| CH | $SO_2CH_3$ | $CH_3$ | H | H | $OC_2H_5$ | $NHCH_3$ | N |
| CH | $SO_2CH_3$ | $CH_3$ | H | $CH_3$ | $OCH_3$ | $CH_3$ | N |
| CH | $SO_2N(CH_3)_2$ | $CH_3$ | H | H | $OCH_3$ | $OCH_3$ | CH |
| CH | $SO_2N(CH_3)_2$ | $CH_3$ | H | H | $OCH_3$ | $CH_3$ | CH |
| CH | $SO_2N(CH_3)_2$ | $CH_3$ | H | H | Cl | $OCH_3$ | CH |
| CH | $SO_2N(CH_3)_2$ | $CH_3$ | H | H | $OCH_3$ | $OCH_3$ | N |
| CH | $SO_2N(CH_3)_2$ | $CH_3$ | H | H | $OCH_3$ | $CH_3$ | N |
| N | H | $CH_3$ | $CH_3$ | H | $OCH_3$ | $OCH_3$ | CH |
| N | H | $CH_3$ | $CH_3$ | H | $OCH_3$ | $CH_3$ | CH |
| N | H | $CH_3$ | $CH_3$ | H | Cl | $OCH_3$ | CH |
| N | H | $CH_3$ | $CH_3$ | H | $CH_3$ | $CH_3$ | CH |
| N | H | $CH_3$ | $CH_3$ | H | $OCH_3$ | $OCH_3$ | N |
| N | H | $CH_3$ | $CH_3$ | H | $OCH_3$ | $CH_3$ | N |
| N | H | $CH_3$ | $CH_3$ | H | $OC_2H_5$ | $NHCH_3$ | N |
| N | H | $CH_3$ | $CH_3$ | $CH_3$ | $OCH_3$ | $CH_3$ | N |
| N | Cl | $CH_3$ | $CH_3$ | H | $OCH_3$ | $OCH_3$ | CH |
| N | Cl | $CH_3$ | $CH_3$ | H | $OCH_3$ | $CH_3$ | CH |
| N | Cl | $CH_3$ | $CH_3$ | H | Cl | $OCH_3$ | CH |
| N | Cl | $CH_3$ | $CH_3$ | H | $CH_3$ | $CH_3$ | CH |
| N | Cl | $CH_3$ | $CH_3$ | H | $OCH_3$ | $OCH_3$ | N |
| N | Cl | $CH_3$ | $CH_3$ | H | $OCH_3$ | $CH_3$ | N |
| N | Cl | $CH_3$ | $CH_3$ | H | $OC_2H_5$ | $NHCH_3$ | N |
| N | Cl | $CH_3$ | $CH_3$ | $CH_3$ | $OCH_3$ | $CH_3$ | N |
| N | $SO_2CH_3$ | $CH_3$ | $CH_3$ | H | $OCH_3$ | $OCH_3$ | CH |
| N | $SO_2CH_3$ | $CH_3$ | $CH_3$ | H | $OCH_3$ | $CH_3$ | CH |
| N | $SO_2CH_3$ | $CH_3$ | $CH_3$ | H | Cl | $OCH_3$ | CH |
| N | $SO_2CH_3$ | $CH_3$ | $CH_3$ | H | $CH_3$ | $CH_3$ | CH |
| N | $SO_2CH_3$ | $CH_3$ | $CH_3$ | H | $OCH_3$ | $OCH_3$ | N |
| N | $SO_2CH_3$ | $CH_3$ | $CH_3$ | H | $OCH_3$ | $CH_3$ | N |
| N | $SO_2CH_3$ | $CH_3$ | $CH_3$ | H | $OC_2H_5$ | $NHCH_3$ | N |
| N | $SO_2CH_3$ | $CH_3$ | $CH_3$ | $CH_3$ | $OCH_3$ | $CH_3$ | N |
| N | $SO_2N(CH_3)_2$ | $CH_3$ | $CH_3$ | H | $OCH_3$ | $OCH_3$ | CH |
| N | $SO_2N(CH_3)_2$ | $CH_3$ | $CH_3$ | H | $OCH_3$ | $CH_3$ | CH |
| N | $SO_2N(CH_3)_2$ | $CH_3$ | $CH_3$ | H | Cl | $OCH_3$ | CH |
| N | $SO_2N(CH_3)_2$ | $CH_3$ | $CH_3$ | H | $OCH_3$ | $OCH_3$ | N |
| N | $SO_2N(CH_3)_2$ | $CH_3$ | $CH_3$ | H | $OCH_3$ | $CH_3$ | N |
| N | H | H | H | H | $OCH_3$ | $OCH_3$ | CH |
| N | H | H | H | H | $OCH_3$ | $CH_3$ | CH |
| N | H | H | H | H | Cl | $OCH_3$ | CH |
| N | H | H | H | H | $CH_3$ | $CH_3$ | CH |
| N | H | H | H | H | $OCH_3$ | $OCH_3$ | N |
| N | H | H | H | H | $OCH_3$ | $CH_3$ | N |
| N | H | H | H | H | $OC_2H_5$ | $NHCH_3$ | N |
| N | H | H | H | $CH_3$ | $OCH_3$ | $CH_3$ | N |
| N | Cl | H | H | H | $OCH_3$ | $OCH_3$ | CH |
| N | Cl | H | H | H | $OCH_3$ | $CH_3$ | CH |
| N | Cl | H | H | H | Cl | $OCH_3$ | CH |
| N | Cl | H | H | H | $CH_3$ | $CH_3$ | CH |
| N | Cl | H | H | H | $OCH_3$ | $OCH_3$ | N |
| N | Cl | H | H | H | $OCH_3$ | $CH_3$ | N |
| N | Cl | H | H | H | $OC_2H_5$ | $NHCH_3$ | N |
| N | Cl | H | H | $CH_3$ | $OCH_3$ | $CH_3$ | N |
| N | $SO_2CH_3$ | H | H | H | $OCH_3$ | $OCH_3$ | CH |
| N | $SO_2CH_3$ | H | H | H | $OCH_3$ | $CH_3$ | CH |
| N | $SO_2CH_3$ | H | H | H | Cl | $OCH_3$ | CH |
| N | $SO_2CH_3$ | H | H | H | $CH_3$ | $CH_3$ | CH |
| N | $SO_2CH_3$ | H | H | H | $OCH_3$ | $OCH_3$ | N |
| N | $SO_2CH_3$ | H | H | H | $OCH_3$ | $CH_3$ | N |
| N | $SO_2CH_3$ | H | H | H | $OC_2H_5$ | $NHCH_3$ | N |
| N | $SO_2CH_3$ | H | H | $CH_3$ | $OCH_3$ | $CH_3$ | N |
| N | $SO_2N(CH_3)_2$ | H | H | H | $OCH_3$ | $OCH_3$ | CH |
| N | $SO_2N(CH_3)_2$ | H | H | H | $OCH_3$ | $CH_3$ | CH |
| N | $SO_2N(CH_3)_2$ | H | H | H | Cl | $OCH_3$ | CH |
| N | $SO_2N(CH_3)_2$ | H | H | H | $OCH_3$ | $OCH_3$ | N |
| N | $SO_2N(CH_3)_2$ | H | H | H | $OCH_3$ | $CH_3$ | N |
| N | H | H | $CH_3$ | H | $OCH_3$ | $OCH_3$ | CH |
| N | H | H | $CH_3$ | H | $OCH_3$ | $CH_3$ | CH |
| N | H | H | $CH_3$ | H | Cl | $OCH_3$ | CH |
| N | H | H | $CH_3$ | H | $CH_3$ | $CH_3$ | CH |
| N | H | H | $CH_3$ | H | $OCH_3$ | $OCH_3$ | N |

TABLE 5-continued

General Formula 5

| $Z^1$ | $R^1$ | $R^2$ | $R^3$ | R | X | Y | $Z^4$ |
|---|---|---|---|---|---|---|---|
| N | H | H | CH$_3$ | H | OCH$_3$ | CH$_3$ | N |
| N | H | H | CH$_3$ | H | OC$_2$H$_5$ | NHCH$_3$ | N |
| N | H | H | CH$_3$ | CH$_3$ | OCH$_3$ | CH$_3$ | N |
| N | Cl | H | CH$_3$ | H | OCH$_3$ | OCH$_3$ | CH |
| N | Cl | H | CH$_3$ | H | OCH$_3$ | CH$_3$ | CH |
| N | Cl | H | CH$_3$ | H | Cl | OCH$_3$ | CH |
| N | Cl | H | CH$_3$ | H | CH$_3$ | CH$_3$ | CH |
| N | Cl | H | CH$_3$ | H | OCH$_3$ | OCH$_3$ | N |
| N | Cl | H | CH$_3$ | H | OCH$_3$ | CH$_3$ | N |
| N | Cl | H | CH$_3$ | H | OC$_2$H$_5$ | NHCH$_3$ | N |
| N | Cl | H | CH$_3$ | CH$_3$ | OCH$_3$ | CH$_3$ | N |
| N | SO$_2$CH$_3$ | H | CH$_3$ | H | OCH$_3$ | OCH$_3$ | CH |
| N | SO$_2$CH$_3$ | H | CH$_3$ | H | OCH$_3$ | CH$_3$ | CH |
| N | SO$_2$CH$_3$ | H | CH$_3$ | H | Cl | OCH$_3$ | CH |
| N | SO$_2$CH$_3$ | H | CH$_3$ | H | CH$_3$ | CH$_3$ | CH |
| N | SO$_2$CH$_3$ | H | CH$_3$ | H | OCH$_3$ | OCH$_3$ | N |
| N | SO$_2$CH$_3$ | H | CH$_3$ | H | OCH$_3$ | CH$_3$ | N |
| N | SO$_2$CH$_3$ | H | CH$_3$ | H | OC$_2$H$_5$ | NHCH$_3$ | N |
| N | SO$_2$CH$_3$ | H | CH$_3$ | CH$_3$ | OCH$_3$ | CH$_3$ | N |
| N | SO$_2$N(CH$_3$)$_2$ | H | CH$_3$ | H | OCH$_3$ | OCH$_3$ | CH |
| N | SO$_2$N(CH$_3$)$_2$ | H | CH$_3$ | H | OCH$_3$ | CH$_3$ | CH |
| N | SO$_2$N(CH$_3$)$_2$ | H | CH$_3$ | H | Cl | OCH$_3$ | CH |
| N | SO$_2$N(CH$_3$)$_2$ | H | CH$_3$ | H | OCH$_3$ | OCH$_3$ | N |
| N | SO$_2$N(CH$_3$)$_2$ | H | CH$_3$ | H | OCH$_3$ | CH$_3$ | N |
| N | H | CH$_3$ | H | H | OCH$_3$ | OCH$_3$ | CH |
| N | H | CH$_3$ | H | H | OCH$_3$ | CH$_3$ | CH |
| N | H | CH$_3$ | H | H | Cl | OCH$_3$ | CH |
| N | H | CH$_3$ | H | H | CH$_3$ | CH$_3$ | CH |
| N | H | CH$_3$ | H | H | OCH$_3$ | OCH$_3$ | N |
| N | H | CH$_3$ | H | H | OCH$_3$ | CH$_3$ | N |
| N | H | CH$_3$ | H | H | OC$_2$H$_5$ | NHCH$_3$ | N |
| N | H | CH$_3$ | H | CH$_3$ | OCH$_3$ | CH$_3$ | N |
| N | Cl | CH$_3$ | H | H | OCH$_3$ | OCH$_3$ | CH |
| N | Cl | CH$_3$ | H | H | OCH$_3$ | CH$_3$ | CH |
| N | Cl | CH$_3$ | H | H | Cl | OCH$_3$ | CH |
| N | Cl | CH$_3$ | H | H | CH$_3$ | CH$_3$ | CH |
| N | Cl | CH$_3$ | H | H | OCH$_3$ | OCH$_3$ | N |
| N | Cl | CH$_3$ | H | H | OCH$_3$ | CH$_3$ | N |
| N | Cl | CH$_3$ | H | H | OC$_2$H$_5$ | NHCH$_3$ | N |
| N | Cl | CH$_3$ | H | CH$_3$ | OCH$_3$ | CH$_3$ | N |
| N | SO$_2$CH$_3$ | CH$_3$ | H | H | OCH$_3$ | OCH$_3$ | CH |
| N | SO$_2$CH$_3$ | CH$_3$ | H | H | OCH$_3$ | CH$_3$ | CH |
| N | SO$_2$CH$_3$ | CH$_3$ | H | H | Cl | OCH$_3$ | CH |
| N | SO$_2$CH$_3$ | CH$_3$ | H | H | CH$_3$ | CH$_3$ | CH |
| N | SO$_2$CH$_3$ | CH$_3$ | H | H | OCH$_3$ | OCH$_3$ | N |
| N | SO$_2$CH$_3$ | CH$_3$ | H | H | OCH$_3$ | CH$_3$ | N |
| N | SO$_2$CH$_3$ | CH$_3$ | H | H | OC$_2$H$_5$ | NHCH$_3$ | N |
| N | SO$_2$CH$_3$ | CH$_3$ | H | CH$_3$ | OCH$_3$ | CH$_3$ | N |
| N | SO$_2$N(CH$_3$)$_2$ | CH$_3$ | H | H | OCH$_3$ | OCH$_3$ | CH |
| N | SO$_2$N(CH$_3$)$_2$ | CH$_3$ | H | H | OCH$_3$ | CH$_3$ | CH |
| N | SO$_2$N(CH$_3$)$_2$ | CH$_3$ | H | H | Cl | OCH$_3$ | CH |
| N | SO$_2$N(CH$_3$)$_2$ | CH$_3$ | H | H | OCH$_3$ | OCH$_3$ | N |
| N | SO$_2$N(CH$_3$)$_2$ | CH$_3$ | H | H | OCH$_3$ | CH$_3$ | N |
| CH | CO$_2$CH$_3$ | CH$_3$ | CH$_3$ | H | OCH$_3$ | OCH$_3$ | CH |
| CH | CO$_2$CH$_3$ | CH$_3$ | CH$_3$ | H | OCH$_3$ | CH$_3$ | CH |
| CH | CO$_2$CH$_3$ | CH$_3$ | CH$_3$ | H | Cl | OCH$_3$ | CH |
| CH | CO$_2$CH$_3$ | CH$_3$ | CH$_3$ | H | CH$_3$ | CH$_3$ | CH |
| CH | CO$_2$CH$_3$ | CH$_3$ | CH$_3$ | H | OCH$_3$ | OCH$_3$ | N |
| CH | CO$_2$CH$_3$ | CH$_3$ | CH$_3$ | H | OCH$_3$ | CH$_3$ | N |
| CH | CO$_2$CH$_3$ | CH$_3$ | CH$_3$ | H | OC$_2$H$_5$ | NHCH$_3$ | N |
| CH | CO$_2$CH$_3$ | CH$_3$ | CH$_3$ | CH$_3$ | OCH$_3$ | CH$_3$ | N |
| CH | CO$_2$CH$_3$ | CH$_3$ | H | H | OCH$_3$ | OCH$_3$ | CH |
| CH | CO$_2$CH$_3$ | CH$_3$ | H | H | OCH$_3$ | CH$_3$ | CH |
| CH | CO$_2$CH$_3$ | CH$_3$ | H | H | Cl | OCH$_3$ | CH |
| CH | CO$_2$CH$_3$ | CH$_3$ | H | H | CH$_3$ | CH$_3$ | CH |
| CH | CO$_2$CH$_3$ | CH$_3$ | H | H | OCH$_3$ | OCH$_3$ | N |
| CH | CO$_2$CH$_3$ | CH$_3$ | H | H | OCH$_3$ | CH$_3$ | N |
| CH | CO$_2$CH$_3$ | CH$_3$ | H | H | OC$_2$H$_5$ | NHCH$_3$ | N |
| CH | CO$_2$CH$_3$ | CH$_3$ | H | CH$_3$ | OCH$_3$ | CH$_3$ | N |
| CH | CO$_2$CH$_3$ | H | CH$_3$ | H | OCH$_3$ | OCH$_3$ | CH |
| CH | CO$_2$CH$_3$ | H | CH$_3$ | H | OCH$_3$ | CH$_3$ | CH |
| CH | CO$_2$CH$_3$ | H | CH$_3$ | H | Cl | OCH$_3$ | CH |
| CH | CO$_2$CH$_3$ | H | CH$_3$ | H | CH$_3$ | CH$_3$ | CH |
| CH | CO$_2$CH$_3$ | H | CH$_3$ | H | OCH$_3$ | OCH$_3$ | N |
| CH | CO$_2$CH$_3$ | H | CH$_3$ | H | OCH$_3$ | CH$_3$ | N |
| CH | CO$_2$CH$_3$ | H | CH$_3$ | H | OC$_2$H$_5$ | NHCH$_3$ | N |
| CH | CO$_2$CH$_3$ | H | CH$_3$ | CH$_3$ | OCH$_3$ | CH$_3$ | N |
| CH | CO$_2$CH$_3$ | H | H | H | OCH$_3$ | OCH$_3$ | CH |
| CH | CO$_2$CH$_3$ | H | H | H | OCH$_3$ | CH$_3$ | CH |
| CH | CO$_2$CH$_3$ | H | H | H | Cl | OCH$_3$ | CH |

TABLE 5-continued

General Formula 5

| $Z^1$ | $R^1$ | $R^2$ | $R^3$ | R | X | Y | $Z^4$ |
|---|---|---|---|---|---|---|---|
| CH | $CO_2CH_3$ | H | H | H | $CH_3$ | $CH_3$ | CH |
| CH | $CO_2CH_3$ | H | H | H | $OCH_3$ | $OCH_3$ | N |
| CH | $CO_2CH_3$ | H | H | H | $OCH_3$ | $CH_3$ | N |
| CH | $CO_2CH_3$ | H | H | H | $OC_2H_5$ | $NHCH_3$ | N |
| CH | $CO_2CH_3$ | H | H | $CH_3$ | $OCH_3$ | $CH_3$ | N |
| CH | $CO_2C_2H_5$ | H | H | H | $OCH_3$ | $OCH_3$ | CH |
| CH | $CO_2C_2H_5$ | H | H | H | $OCH_3$ | $CH_3$ | CH |
| CH | $CO_2C_2H_5$ | H | H | H | Cl | $OCH_3$ | CH |
| CH | $CO_2C_2H_5$ | H | H | H | $CH_3$ | $CH_3$ | CH |
| CH | $CO_2C_2H_5$ | H | H | H | $OCH_3$ | $OCH_3$ | N |
| CH | $CO_2C_2H_5$ | H | H | H | $OCH_3$ | $CH_3$ | N |
| CH | $CO_2C_2H_5$ | H | H | H | $OC_2H_5$ | $NHCH_3$ | N |
| CH | $CO_2C_2H_5$ | H | H | $CH_3$ | $OCH_3$ | $CH_3$ | N |
| CH | $CO_2C_2H_5$ | $CH_3$ | $CH_3$ | H | $OCH_3$ | $OCH_3$ | CH |
| CH | $CO_2C_2H_5$ | $CH_3$ | $CH_3$ | H | $OCH_3$ | $CH_3$ | CH |
| CH | $CO_2C_2H_5$ | $CH_3$ | $CH_3$ | H | Cl | $OCH_3$ | CH |
| CH | $CO_2C_2H_5$ | $CH_3$ | $CH_3$ | H | $CH_3$ | $CH_3$ | CH |
| CH | $CO_2C_2H_5$ | $CH_3$ | $CH_3$ | H | $OCH_3$ | $OCH_3$ | N |
| CH | $CO_2C_2H_5$ | $CH_3$ | $CH_3$ | H | $OCH_3$ | $CH_3$ | N |
| CH | $CO_2C_2H_5$ | $CH_3$ | $CH_3$ | H | $OC_2H_5$ | $NHCH_3$ | N |
| CH | $CO_2C_2H_5$ | $CH_3$ | $CH_3$ | $CH_3$ | $OCH_3$ | $CH_3$ | N |
| N | $CO_2CH_3$ | $CH_3$ | $CH_3$ | H | $OCH_3$ | $OCH_3$ | CH |
| N | $CO_2CH_3$ | $CH_3$ | $CH_3$ | H | $OCH_3$ | $CH_3$ | CH |
| N | $CO_2CH_3$ | $CH_3$ | $CH_3$ | H | Cl | $OCH_3$ | CH |
| N | $CO_2CH_3$ | $CH_3$ | $CH_3$ | H | $CH_3$ | $CH_3$ | CH |
| N | $CO_2CH_3$ | $CH_3$ | $CH_3$ | H | $OCH_3$ | $OCH_3$ | N |
| N | $CO_2CH_3$ | $CH_3$ | $CH_3$ | H | $OCH_3$ | $CH_3$ | N |
| N | $CO_2CH_3$ | $CH_3$ | $CH_3$ | H | $OC_2H_5$ | $NHCH_3$ | N |
| N | $CO_2CH_3$ | $CH_3$ | $CH_3$ | $CH_3$ | $OCH_3$ | $CH_3$ | N |
| N | $CO_2CH_3$ | $CH_3$ | H | H | $OCH_3$ | $OCH_3$ | CH |
| N | $CO_2CH_3$ | $CH_3$ | H | H | $OCH_3$ | $CH_3$ | CH |
| N | $CO_2CH_3$ | $CH_3$ | H | H | Cl | $OCH_3$ | CH |
| N | $CO_2CH_3$ | $CH_3$ | H | H | $CH_3$ | $CH_3$ | CH |
| N | $CO_2CH_3$ | $CH_3$ | H | H | $OCH_3$ | $OCH_3$ | N |
| N | $CO_2CH_3$ | $CH_3$ | H | H | $OCH_3$ | $CH_3$ | N |
| N | $CO_2CH_3$ | $CH_3$ | H | H | $OC_2H_5$ | $NHCH_3$ | N |
| N | $CO_2CH_3$ | $CH_3$ | H | $CH_3$ | $OCH_3$ | $CH_3$ | N |
| N | $CO_2CH_3$ | H | $CH_3$ | H | $OCH_3$ | $OCH_3$ | CH |
| N | $CO_2CH_3$ | H | $CH_3$ | H | $OCH_3$ | $CH_3$ | CH |
| N | $CO_2CH_3$ | H | $CH_3$ | H | Cl | $OCH_3$ | CH |
| N | $CO_2CH_3$ | H | $CH_3$ | H | $CH_3$ | $CH_3$ | CH |
| N | $CO_2CH_3$ | H | $CH_3$ | H | $OCH_3$ | $OCH_3$ | N |
| N | $CO_2CH_3$ | H | $CH_3$ | H | $OCH_3$ | $CH_3$ | N |
| N | $CO_2CH_3$ | H | $CH_3$ | H | $OC_2H_5$ | $NHCH_3$ | N |
| N | $CO_2CH_3$ | H | $CH_3$ | $CH_3$ | $OCH_3$ | $CH_3$ | N |
| N | $CO_2CH_3$ | H | H | H | $OCH_3$ | $OCH_3$ | CH |
| N | $CO_2CH_3$ | H | H | H | $OCH_3$ | $CH_3$ | CH |
| N | $CO_2CH_3$ | H | H | H | Cl | $OCH_3$ | CH |
| N | $CO_2CH_3$ | H | H | H | $CH_3$ | $CH_3$ | CH |
| N | $CO_2CH_3$ | H | H | H | $OCH_3$ | $OCH_3$ | N |
| N | $CO_2CH_3$ | H | H | H | $OCH_3$ | $CH_3$ | N |
| N | $CO_2CH_3$ | H | H | H | $OC_2H_5$ | $NHCH_3$ | N |
| N | $CO_2CH_3$ | H | H | $CH_3$ | $OCH_3$ | $CH_3$ | N |
| N | $CO_2C_2H_5$ | H | H | H | $OCH_3$ | $OCH_3$ | CH |
| N | $CO_2C_2H_5$ | H | H | H | $OCH_3$ | $CH_3$ | CH |
| N | $CO_2C_2H_5$ | H | H | H | Cl | $OCH_3$ | CH |
| N | $CO_2C_2H_5$ | H | H | H | $CH_3$ | $CH_3$ | CH |
| N | $CO_2C_2H_5$ | H | H | H | $OCH_3$ | $OCH_3$ | N |
| N | $CO_2C_2H_5$ | H | H | H | $OCH_3$ | $CH_3$ | N |
| N | $CO_2C_2H_5$ | H | H | H | $OC_2H_5$ | $NHCH_3$ | N |
| N | $CO_2C_2H_5$ | H | H | $CH_3$ | $OCH_3$ | $CH_3$ | N |
| N | $CO_2C_2H_5$ | $CH_3$ | $CH_3$ | H | $OCH_3$ | $OCH_3$ | CH |
| N | $CO_2C_2H_5$ | $CH_3$ | $CH_3$ | H | $OCH_3$ | $CH_3$ | CH |
| N | $CO_2C_2H_5$ | $CH_3$ | $CH_3$ | H | Cl | $OCH_3$ | CH |
| N | $CO_2C_2H_5$ | $CH_3$ | $CH_3$ | H | $CH_3$ | $CH_3$ | CH |
| N | $CO_2C_2H_5$ | $CH_3$ | $CH_3$ | H | $OCH_3$ | $OCH_3$ | N |
| N | $CO_2C_2H_5$ | $CH_3$ | $CH_3$ | H | $OCH_3$ | $CH_3$ | N |
| N | $CO_2C_2H_5$ | $CH_3$ | $CH_3$ | H | $OC_2H_5$ | $NHCH_3$ | N |
| N | $CO_2C_2H_5$ | $CH_3$ | $CH_3$ | $CH_3$ | $OCH_3$ | $CH_3$ | N |

TABLE 6

General Formula 6

| $R^2$ | $R^3$ | $R^4$ | R | X | Y | $Z^4$ |
|---|---|---|---|---|---|---|
| $CH_3$ | $CH_3$ | H | H | $OCH_3$ | $OCH_3$ | CH |
| $CH_3$ | $CH_3$ | H | H | $OCH_3$ | $CH_3$ | CH |
| $CH_3$ | $CH_3$ | H | H | Cl | $OCH_3$ | CH |
| $CH_3$ | $CH_3$ | H | H | $CH_3$ | $CH_3$ | CH |
| $CH_3$ | $CH_3$ | H | H | $OCH_3$ | $OCH_3$ | N |
| $CH_3$ | $CH_3$ | H | H | $OCH_3$ | $CH_3$ | N |
| $CH_3$ | $CH_3$ | H | H | $OC_2H_5$ | $NHCH_3$ | N |
| $CH_3$ | $CH_3$ | H | $CH_3$ | $OCH_3$ | $CH_3$ | N |

TABLE 6-continued

General Formula 6

| R² | R³ | R⁴ | R | X | Y | Z⁴ |
|---|---|---|---|---|---|---|
| H | CH₃ | H | H | OCH₃ | OCH₃ | CH |
| H | CH₃ | H | H | OCH₃ | CH₃ | CH |
| H | CH₃ | H | H | Cl | OCH₃ | CH |
| H | CH₃ | H | H | CH₃ | CH₃ | CH |
| H | CH₃ | H | H | OCH₃ | OCH₃ | N |
| H | CH₃ | H | H | OCH₃ | CH₃ | N |
| H | CH₃ | H | H | OC₂H₅ | NHCH₃ | N |
| H | CH₃ | H | CH₃ | OCH₃ | CH₃ | N |
| CH₃ | H | H | H | OCH₃ | OCH₃ | CH |
| CH₃ | H | H | H | OCH₃ | CH₃ | CH |
| CH₃ | H | H | H | Cl | OCH₃ | CH |
| CH₃ | H | H | H | CH₃ | CH₃ | CH |
| CH₃ | H | H | H | OCH₃ | OCH₃ | N |
| CH₃ | H | H | H | OCH₃ | CH₃ | N |
| CH₃ | H | H | H | OC₂H₅ | NHCH₃ | N |
| CH₃ | H | H | CH₃ | OCH₃ | CH₃ | N |
| H | H | H | H | OCH₃ | OCH₃ | CH |
| H | H | H | H | OCH₃ | CH₃ | CH |
| H | H | H | H | Cl | OCH₃ | CH |
| H | H | H | H | CH₃ | CH₃ | CH |
| H | H | H | H | OCH₃ | OCH₃ | N |
| H | H | H | H | OCH₃ | CH₃ | N |
| H | H | H | H | OC₂H₅ | NHCH₃ | N |
| H | H | H | CH₃ | OCH₃ | CH₃ | N |

TABLE 7

General Formula 7

| R⁴ | R¹ | R² | R³ | R | X | Y | Z⁴ |
|---|---|---|---|---|---|---|---|
| H | H | CH₃ | CH₃ | H | OCH₃ | OCH₃ | CH |
| H | H | CH₃ | CH₃ | H | OCH₃ | CH₃ | CH |
| H | H | CH₃ | CH₃ | H | Cl | OCH₃ | CH |
| H | H | CH₃ | CH₃ | H | CH₃ | CH₃ | CH |
| H | H | CH₃ | CH₃ | H | OCH₃ | OCH₃ | N |
| H | H | CH₃ | CH₃ | H | OCH₃ | CH₃ | N |
| H | H | CH₃ | CH₃ | H | OC₂H₅ | NHCH₃ | N |
| H | H | CH₃ | CH₃ | CH₃ | OCH₃ | CH₃ | N |
| H | Cl | CH₃ | CH₃ | H | OCH₃ | OCH₃ | CH |
| H | Cl | CH₃ | CH₃ | H | OCH₃ | CH₃ | CH |
| H | Cl | CH₃ | CH₃ | H | Cl | OCH₃ | CH |
| H | Cl | CH₃ | CH₃ | H | CH₃ | CH₃ | CH |
| H | Cl | CH₃ | CH₃ | H | OCH₃ | OCH₃ | N |
| H | Cl | CH₃ | CH₃ | H | OCH₃ | CH₃ | N |
| H | Cl | CH₃ | CH₃ | H | OC₂H₅ | NHCH₃ | N |
| H | Cl | CH₃ | CH₃ | CH₃ | OCH₃ | CH₃ | N |
| H | SO₂CH₃ | CH₃ | CH₃ | H | OCH₃ | OCH₃ | CH |
| H | SO₂CH₃ | CH₃ | CH₃ | H | OCH₃ | CH₃ | CH |
| H | SO₂CH₃ | CH₃ | CH₃ | H | Cl | OCH₃ | CH |
| H | SO₂CH₃ | CH₃ | CH₃ | H | CH₃ | CH₃ | CH |
| H | SO₂CH₃ | CH₃ | CH₃ | H | OCH₃ | OCH₃ | N |
| H | SO₂CH₃ | CH₃ | CH₃ | H | OCH₃ | CH₃ | N |
| H | SO₂CH₃ | CH₃ | CH₃ | H | OC₂H₅ | NHCH₃ | N |
| H | SO₂CH₃ | CH₃ | CH₃ | CH₃ | OCH₃ | CH₃ | N |
| H | SO₂N(CH₃)₂ | CH₃ | CH₃ | H | OCH₃ | OCH₃ | CH |
| H | SO₂N(CH₃)₂ | CH₃ | CH₃ | H | OCH₃ | CH₃ | CH |
| H | SO₂N(CH₃)₂ | CH₃ | CH₃ | H | Cl | OCH₃ | CH |
| H | SO₂N(CH₃)₂ | CH₃ | CH₃ | H | OCH₃ | OCH₃ | N |
| H | SO₂N(CH₃)₂ | CH₃ | CH₃ | H | OCH₃ | CH₃ | N |
| H | H | H | H | H | OCH₃ | OCH₃ | CH |
| H | H | H | H | H | OCH₃ | CH₃ | CH |
| H | H | H | H | H | Cl | OCH₃ | CH |
| H | H | H | H | H | CH₃ | CH₃ | CH |
| H | H | H | H | H | OCH₃ | OCH₃ | N |
| H | H | H | H | H | OCH₃ | CH₃ | N |
| H | H | H | H | H | OC₂H₅ | NHCH₃ | N |
| H | H | H | H | CH₃ | OCH₃ | CH₃ | N |
| H | Cl | H | H | H | OCH₃ | OCH₃ | CH |
| H | Cl | H | H | H | OCH₃ | CH₃ | CH |
| H | Cl | H | H | H | Cl | OCH₃ | CH |
| H | Cl | H | H | H | CH₃ | CH₃ | CH |
| H | Cl | H | H | H | OCH₃ | OCH₃ | N |
| H | Cl | H | H | H | OCH₃ | CH₃ | N |
| H | Cl | H | H | H | OC₂H₅ | NHCH₃ | N |
| H | Cl | H | H | CH₃ | OCH₃ | CH₃ | N |
| H | SO₂CH₃ | H | H | H | OCH₃ | OCH₃ | CH |
| H | SO₂CH₃ | H | H | H | OCH₃ | CH₃ | CH |
| H | SO₂CH₃ | H | H | H | Cl | OCH₃ | CH |
| H | SO₂CH₃ | H | H | H | CH₃ | CH₃ | CH |

TABLE 7-continued

General Formula 7

| R⁴ | R¹ | R² | R³ | R | X | Y | Z⁴ |
|---|---|---|---|---|---|---|---|
| H | SO₂CH₃ | H | H | H | OCH₃ | OCH₃ | N |
| H | SO₂CH₃ | H | H | H | OCH₃ | CH₃ | N |
| H | SO₂CH₃ | H | H | H | OC₂H₅ | NHCH₃ | N |
| H | SO₂CH₃ | H | H | CH₃ | OCH₃ | CH₃ | N |
| H | SO₂N(CH₃)₂ | H | H | H | OCH₃ | OCH₃ | CH |
| H | SO₂N(CH₃)₂ | H | H | H | OCH₃ | CH₃ | CH |
| H | SO₂N(CH₃)₂ | H | H | H | Cl | OCH₃ | CH |
| H | SO₂N(CH₃)₂ | H | H | H | OCH₃ | OCH₃ | N |
| H | SO₂N(CH₃)₂ | H | H | H | OCH₃ | CH₃ | N |
| H | H | H | CH₃ | H | OCH₃ | OCH₃ | CH |
| H | H | H | CH₃ | H | OCH₃ | CH₃ | CH |
| H | H | H | CH₃ | H | Cl | OCH₃ | CH |
| H | H | H | CH₃ | H | CH₃ | CH₃ | CH |
| H | H | H | CH₃ | H | OCH₃ | OCH₃ | N |
| H | H | H | CH₃ | H | OCH₃ | CH₃ | N |
| H | H | H | CH₃ | H | OC₂H₅ | NHCH₃ | N |
| H | H | H | CH₃ | CH₃ | OCH₃ | CH₃ | N |
| H | Cl | H | CH₃ | H | OCH₃ | OCH₃ | CH |
| H | Cl | H | CH₃ | H | OCH₃ | CH₃ | CH |
| H | Cl | H | CH₃ | H | Cl | OCH₃ | CH |
| H | Cl | H | CH₃ | H | CH₃ | CH₃ | CH |
| H | Cl | H | CH₃ | H | OCH₃ | OCH₃ | N |
| H | Cl | H | CH₃ | H | OCH₃ | CH₃ | N |
| H | Cl | H | CH₃ | H | OC₂H₅ | NHCH₃ | N |
| H | Cl | H | CH₃ | CH₃ | OCH₃ | CH₃ | N |
| H | SO₂CH₃ | H | CH₃ | H | OCH₃ | OCH₃ | CH |
| H | SO₂CH₃ | H | CH₃ | H | OCH₃ | CH₃ | CH |
| H | SO₂CH₃ | H | CH₃ | H | Cl | OCH₃ | CH |
| H | SO₂CH₃ | H | CH₃ | H | CH₃ | CH₃ | CH |
| H | SO₂CH₃ | H | CH₃ | H | OCH₃ | OCH₃ | N |
| H | SO₂CH₃ | H | CH₃ | H | OCH₃ | CH₃ | N |
| H | SO₂CH₃ | H | CH₃ | H | OC₂H₅ | NHCH₃ | N |
| H | SO₂CH₃ | H | CH₃ | CH₃ | OCH₃ | CH₃ | N |
| H | SO₂N(CH₃)₂ | H | CH₃ | H | OCH₃ | OCH₃ | CH |
| H | SO₂N(CH₃)₂ | H | CH₃ | H | OCH₃ | CH₃ | CH |
| H | SO₂N(CH₃)₂ | H | CH₃ | H | Cl | OCH₃ | CH |
| H | SO₂N(CH₃)₂ | H | CH₃ | H | OCH₃ | OCH₃ | N |
| H | SO₂N(CH₃)₂ | H | CH₃ | H | OCH₃ | CH₃ | N |
| H | CO₂CH₃ | CH₃ | CH₃ | H | OCH₃ | OCH₃ | CH |
| H | CO₂CH₃ | CH₃ | CH₃ | H | OCH₃ | CH₃ | CH |
| H | CO₂CH₃ | CH₃ | CH₃ | H | Cl | OCH₃ | CH |
| H | CO₂CH₃ | CH₃ | CH₃ | H | CH₃ | CH₃ | CH |
| H | CO₂CH₃ | CH₃ | CH₃ | H | OCH₃ | OCH₃ | N |
| H | CO₂CH₃ | CH₃ | CH₃ | H | OCH₃ | CH₃ | N |
| H | CO₂CH₃ | CH₃ | CH₃ | H | OC₂H₅ | NHCH₃ | N |
| H | CO₂CH₃ | CH₃ | CH₃ | CH₃ | OCH₃ | CH₃ | N |
| H | CO₂CH₃ | CH₃ | H | H | OCH₃ | OCH₃ | CH |
| H | CO₂CH₃ | CH₃ | H | H | OCH₃ | CH₃ | CH |
| H | CO₂CH₃ | CH₃ | H | H | Cl | OCH₃ | CH |
| H | CO₂CH₃ | CH₃ | H | H | CH₃ | CH₃ | CH |
| H | CO₂CH₃ | CH₃ | H | H | OCH₃ | OCH₃ | N |
| H | CO₂CH₃ | CH₃ | H | H | OCH₃ | CH₃ | N |
| H | CO₂CH₃ | CH₃ | H | H | OC₂H₅ | NHCH₃ | N |
| H | CO₂CH₃ | CH₃ | H | CH₃ | OCH₃ | CH₃ | N |
| H | CO₂CH₃ | H | CH₃ | H | OCH₃ | OCH₃ | CH |
| H | CO₂CH₃ | H | CH₃ | H | OCH₃ | CH₃ | CH |
| H | CO₂CH₃ | H | CH₃ | H | Cl | OCH₃ | CH |
| H | CO₂CH₃ | H | CH₃ | H | CH₃ | CH₃ | CH |
| H | CO₂CH₃ | H | CH₃ | H | OCH₃ | OCH₃ | N |
| H | CO₂CH₃ | H | CH₃ | H | OCH₃ | CH₃ | N |
| H | CO₂CH₃ | H | CH₃ | H | OC₂H₅ | NHCH₃ | N |
| H | CO₂CH₃ | H | CH₃ | CH₃ | OCH₃ | CH₃ | N |
| H | CO₂CH₃ | H | H | H | OCH₃ | OCH₃ | CH |
| H | CO₂CH₃ | H | H | H | OCH₃ | CH₃ | CH |
| H | CO₂CH₃ | H | H | H | Cl | OCH₃ | CH |
| H | CO₂CH₃ | H | H | H | CH₃ | CH₃ | CH |
| H | CO₂CH₃ | H | H | H | OCH₃ | OCH₃ | N |
| H | CO₂CH₃ | H | H | H | OCH₃ | CH₃ | N |
| H | CO₂CH₃ | H | H | H | OC₂H₅ | NHCH₃ | N |
| H | CO₂CH₃ | H | H | CH₃ | OCH₃ | CH₃ | N |
| H | CO₂C₂H₅ | CH₃ | CH₃ | H | OCH₃ | OCH₃ | CH |
| H | CO₂C₂H₅ | H | H | H | OCH₃ | CH₃ | CH |
| H | CO₂C₂H₅ | H | H | H | Cl | OCH₃ | CH |
| H | CO₂C₂H₅ | H | H | H | CH₃ | CH₃ | CH |
| H | CO₂C₂H₅ | H | H | H | OCH₃ | OCH₃ | N |
| H | CO₂C₂H₅ | H | H | H | OCH₃ | CH₃ | N |
| H | CO₂C₂H₅ | H | H | H | OC₂H₅ | NHCH₃ | N |
| H | CO₂C₂H₅ | H | H | CH₃ | OCH₃ | CH₃ | N |
| H | CO₂C₂H₅ | CH₃ | CH₃ | H | OCH₃ | OCH₃ | CH |

TABLE 7-continued

General Formula 7

| R⁴ | R¹ | R² | R³ | R | X | Y | Z⁴ |
|---|---|---|---|---|---|---|---|
| H | $CO_2C_2H_5$ | $CH_3$ | $CH_3$ | H | $OCH_3$ | $CH_3$ | CH |
| H | $CO_2C_2H_5$ | $CH_3$ | $CH_3$ | H | Cl | $OCH_3$ | CH |
| H | $CO_2C_2H_5$ | $CH_3$ | $CH_3$ | H | $CH_3$ | $CH_3$ | CH |
| H | $CO_2C_2H_5$ | $CH_3$ | $CH_3$ | H | $OCH_3$ | $OCH_3$ | N |
| H | $CO_2C_2H_5$ | $CH_3$ | $CH_3$ | H | $OCH_3$ | $CH_3$ | N |
| H | $CO_2C_2H_5$ | $CH_3$ | $CH_3$ | H | $OC_2H_5$ | $NHCH_3$ | N |
| H | $CO_2C_2H_5$ | $CH_3$ | $CH_3$ | $CH_3$ | $OCH_3$ | $CH_3$ | N |
| H | H | $CH_3$ | H | H | $OCH_3$ | $OCH_3$ | CH |
| H | H | $CH_3$ | H | H | $OCH_3$ | $CH_3$ | CH |
| H | H | $CH_3$ | H | H | Cl | $OCH_3$ | CH |
| H | H | $CH_3$ | H | H | $CH_3$ | $CH_3$ | CH |
| H | H | $CH_3$ | H | H | $OCH_3$ | $OCH_3$ | N |

TABLE 8

General Formula 8

| Z¹ | R¹ | R² | R³ | R⁵ | R | X | Y | Z⁴ |
|---|---|---|---|---|---|---|---|---|
| CH | H | $CH_3$ | $CH_3$ | H | H | $OCH_3$ | $OCH_3$ | CH |
| CH | H | $CH_3$ | $CH_3$ | H | H | $OCH_3$ | $CH_3$ | CH |
| CH | H | $CH_3$ | $CH_3$ | H | H | Cl | $OCH_3$ | CH |
| CH | H | $CH_3$ | $CH_3$ | H | H | $CH_3$ | $CH_3$ | CH |
| CH | H | $CH_3$ | $CH_3$ | H | H | $OCH_3$ | $OCH_3$ | N |
| CH | H | $CH_3$ | $CH_3$ | H | H | $OCH_3$ | $CH_3$ | N |
| CH | H | $CH_3$ | $CH_3$ | H | H | $OC_2H_5$ | $NHCH_3$ | N |
| CH | H | $CH_3$ | $CH_3$ | H | $CH_3$ | $OCH_3$ | $CH_3$ | N |
| CH | Cl | $CH_3$ | $CH_3$ | H | H | $OCH_3$ | $OCH_3$ | CH |
| CH | Cl | $CH_3$ | $CH_3$ | H | H | $OCH_3$ | $CH_3$ | CH |
| CH | Cl | $CH_3$ | $CH_3$ | H | H | Cl | $OCH_3$ | CH |
| CH | Cl | $CH_3$ | $CH_3$ | H | H | $CH_3$ | $CH_3$ | CH |
| CH | Cl | $CH_3$ | $CH_3$ | H | H | $OCH_3$ | $OCH_3$ | N |
| CH | Cl | $CH_3$ | $CH_3$ | H | H | $OCH_3$ | $CH_3$ | N |
| CH | Cl | $CH_3$ | $CH_3$ | H | H | $OC_2H_5$ | $NHCH_3$ | N |
| CH | Cl | $CH_3$ | $CH_3$ | H | $CH_3$ | $OCH_3$ | $CH_3$ | N |
| CH | $SO_2CH_3$ | $CH_3$ | $CH_3$ | H | H | $OCH_3$ | $OCH_3$ | CH |
| CH | $SO_2CH_3$ | $CH_3$ | $CH_3$ | H | H | $OCH_3$ | $CH_3$ | CH |
| CH | $SO_2CH_3$ | $CH_3$ | $CH_3$ | H | H | Cl | $OCH_3$ | CH |
| CH | $SO_2CH_3$ | $CH_3$ | $CH_3$ | H | H | $CH_3$ | $CH_3$ | CH |
| CH | $SO_2CH_3$ | $CH_3$ | $CH_3$ | H | H | $OCH_3$ | $OCH_3$ | N |
| CH | $SO_2CH_3$ | $CH_3$ | $CH_3$ | H | H | $OCH_3$ | $CH_3$ | N |
| CH | $SO_2CH_3$ | $CH_3$ | $CH_3$ | H | H | $OC_2H_5$ | $NHCH_3$ | N |
| CH | $SO_2CH_3$ | $CH_3$ | $CH_3$ | H | $CH_3$ | $OCH_3$ | $CH_3$ | N |
| CH | $SO_2N(CH_3)_2$ | $CH_3$ | $CH_3$ | H | H | $OCH_3$ | $OCH_3$ | CH |
| CH | $SO_2N(CH_3)_2$ | $CH_3$ | $CH_3$ | H | H | $OCH_3$ | $CH_3$ | CH |
| CH | $SO_2N(CH_3)_2$ | $CH_3$ | $CH_3$ | H | H | Cl | $OCH_3$ | CH |
| CH | $SO_2N(CH_3)_2$ | $CH_3$ | $CH_3$ | H | H | $OCH_3$ | $OCH_3$ | N |
| CH | $SO_2N(CH_3)_2$ | $CH_3$ | $CH_3$ | H | H | $OCH_3$ | $CH_3$ | N |
| N | H | $CH_3$ | $CH_3$ | H | H | $OCH_3$ | $OCH_3$ | CH |
| N | H | $CH_3$ | $CH_3$ | H | H | $OCH_3$ | $CH_3$ | CH |
| N | H | $CH_3$ | $CH_3$ | H | H | Cl | $OCH_3$ | CH |
| N | H | $CH_3$ | $CH_3$ | H | H | $CH_3$ | $CH_3$ | CH |
| N | H | $CH_3$ | $CH_3$ | H | H | $OCH_3$ | $OCH_3$ | N |
| N | H | $CH_3$ | $CH_3$ | H | H | $OCH_3$ | $CH_3$ | N |
| N | H | $CH_3$ | $CH_3$ | H | H | $OC_2H_5$ | $NHCH_3$ | N |
| N | H | $CH_3$ | $CH_3$ | H | $CH_3$ | $OCH_3$ | $CH_3$ | N |
| N | Cl | $CH_3$ | $CH_3$ | H | H | $OCH_3$ | $OCH_3$ | CH |
| N | Cl | $CH_3$ | $CH_3$ | H | H | $OCH_3$ | $CH_3$ | CH |
| N | Cl | $CH_3$ | $CH_3$ | H | H | Cl | $OCH_3$ | CH |
| N | Cl | $CH_3$ | $CH_3$ | H | H | $CH_3$ | $CH_3$ | CH |
| N | Cl | $CH_3$ | $CH_3$ | H | H | $OCH_3$ | $OCH_3$ | N |
| N | Cl | $CH_3$ | $CH_3$ | H | H | $OCH_3$ | $CH_3$ | N |
| N | Cl | $CH_3$ | $CH_3$ | H | H | $OC_2H_5$ | $NHCH_3$ | N |
| N | Cl | $CH_3$ | $CH_3$ | H | $CH_3$ | $OCH_3$ | $CH_3$ | N |
| N | $SO_2CH_3$ | $CH_3$ | $CH_3$ | H | H | $OCH_3$ | $OCH_3$ | CH |
| N | $SO_2CH_3$ | $CH_3$ | $CH_3$ | H | H | $OCH_3$ | $CH_3$ | CH |
| N | $SO_2CH_3$ | $CH_3$ | $CH_3$ | H | H | Cl | $OCH_3$ | CH |
| N | $SO_2CH_3$ | $CH_3$ | $CH_3$ | H | H | $CH_3$ | $CH_3$ | CH |
| N | $SO_2CH_3$ | $CH_3$ | $CH_3$ | H | H | $OCH_3$ | $OCH_3$ | N |
| N | $SO_2CH_3$ | $CH_3$ | $CH_3$ | H | H | $OCH_3$ | $CH_3$ | N |
| N | $SO_2CH_3$ | $CH_3$ | $CH_3$ | H | H | $OC_2H_5$ | $NHCH_3$ | N |
| N | $SO_2CH_3$ | $CH_3$ | $CH_3$ | H | $CH_3$ | $OCH_3$ | $CH_3$ | N |
| N | $SO_2N(CH_3)_2$ | $CH_3$ | $CH_3$ | H | H | $OCH_3$ | $OCH_3$ | CH |
| N | $SO_2N(CH_3)_2$ | $CH_3$ | $CH_3$ | H | H | $OCH_3$ | $CH_3$ | CH |
| N | $SO_2N(CH_3)_2$ | $CH_3$ | $CH_3$ | H | H | Cl | $OCH_3$ | CH |
| N | $SO_2N(CH_3)_2$ | $CH_3$ | $CH_3$ | H | H | $OCH_3$ | $OCH_3$ | N |
| N | $SO_2N(CH_3)_2$ | $CH_3$ | $CH_3$ | H | H | $OCH_3$ | $CH_3$ | N |
| N | H | H | H | H | H | $OCH_3$ | $OCH_3$ | CH |

TABLE 8-continued

General Formula 8

| $Z^1$ | $R^1$ | $R^2$ | $R^3$ | $R^5$ | R | X | Y | $Z^4$ |
|---|---|---|---|---|---|---|---|---|
| N | H | H | H | H | H | OCH$_3$ | CH$_3$ | CH |
| N | H | H | H | H | H | Cl | OCH$_3$ | CH |
| N | H | H | H | H | H | CH$_3$ | CH$_3$ | CH |
| N | H | H | H | H | H | OCH$_3$ | OCH$_3$ | N |
| N | H | H | H | H | H | OCH$_3$ | CH$_3$ | N |
| N | H | H | H | H | H | OC$_2$H$_5$ | NHCH$_3$ | N |
| N | H | H | H | H | CH$_3$ | OCH$_3$ | CH$_3$ | N |
| N | Cl | H | H | H | H | OCH$_3$ | OCH$_3$ | CH |
| N | Cl | H | H | H | H | OCH$_3$ | CH$_3$ | CH |
| N | Cl | H | H | H | H | Cl | OCH$_3$ | CH |
| N | Cl | H | H | H | H | CH$_3$ | CH$_3$ | CH |
| N | Cl | H | H | H | H | OCH$_3$ | OCH$_3$ | N |
| N | Cl | H | H | H | H | OCH$_3$ | CH$_3$ | N |
| N | Cl | H | H | H | H | OC$_2$H$_5$ | NHCH$_3$ | N |
| N | Cl | H | H | H | CH$_3$ | OCH$_3$ | CH$_3$ | N |
| N | SO$_2$CH$_3$ | H | H | H | H | OCH$_3$ | OCH$_3$ | CH |
| N | SO$_2$CH$_3$ | H | H | H | H | OCH$_3$ | CH$_3$ | CH |
| N | SO$_2$CH$_3$ | H | H | H | H | Cl | OCH$_3$ | CH |
| N | SO$_2$CH$_3$ | H | H | H | H | CH$_3$ | CH$_3$ | CH |
| N | SO$_2$CH$_3$ | H | H | H | H | OCH$_3$ | OCH$_3$ | N |
| N | SO$_2$CH$_3$ | H | H | H | H | OCH$_3$ | CH$_3$ | N |
| N | SO$_2$CH$_3$ | H | H | H | H | OC$_2$H$_5$ | NHCH$_3$ | N |
| N | SO$_2$CH$_3$ | H | H | H | CH$_3$ | OCH$_3$ | CH$_3$ | N |
| N | SO$_2$N(CH$_3$)$_2$ | H | H | H | H | OCH$_3$ | OCH$_3$ | CH |
| N | SO$_2$N(CH$_3$)$_2$ | H | H | H | H | OCH$_3$ | CH$_3$ | CH |
| N | SO$_2$N(CH$_3$)$_2$ | H | H | H | H | Cl | OCH$_3$ | CH |
| N | SO$_2$N(CH$_3$)$_2$ | H | H | H | H | OCH$_3$ | OCH$_3$ | N |
| N | SO$_2$N(CH$_3$)$_2$ | H | H | H | H | OCH$_3$ | CH$_3$ | N |
| CH | H | H | H | H | H | OCH$_3$ | OCH$_3$ | CH |
| CH | H | H | H | H | H | OCH$_3$ | CH$_3$ | CH |
| CH | H | H | H | H | H | Cl | OCH$_3$ | CH |
| CH | H | H | H | H | H | CH$_3$ | CH$_3$ | CH |
| CH | H | H | H | H | H | OCH$_3$ | OCH$_3$ | N |
| CH | H | H | H | H | H | OCH$_3$ | CH$_3$ | N |
| CH | H | H | H | H | H | OC$_2$H$_5$ | NHCH$_3$ | N |
| CH | H | H | H | H | CH$_3$ | OCH$_3$ | CH$_3$ | N |
| CH | Cl | H | H | H | H | OCH$_3$ | OCH$_3$ | CH |
| CH | Cl | H | H | H | H | OCH$_3$ | CH$_3$ | CH |
| CH | Cl | H | H | H | H | Cl | OCH$_3$ | CH |
| CH | Cl | H | H | H | H | CH$_3$ | CH$_3$ | CH |
| CH | Cl | H | H | H | H | OCH$_3$ | OCH$_3$ | N |
| CH | Cl | H | H | H | H | OCH$_3$ | CH$_3$ | N |
| CH | Cl | H | H | H | H | OC$_2$H$_5$ | NHCH$_3$ | N |
| CH | Cl | H | H | H | CH$_3$ | OCH$_3$ | CH$_3$ | N |
| CH | SO$_2$CH$_3$ | H | H | H | H | OCH$_3$ | OCH$_3$ | CH |
| CH | SO$_2$CH$_3$ | H | H | H | H | OCH$_3$ | CH$_3$ | CH |
| CH | SO$_2$CH$_3$ | H | H | H | H | Cl | OCH$_3$ | CH |
| CH | SO$_2$CH$_3$ | H | H | H | H | CH$_3$ | CH$_3$ | CH |
| CH | SO$_2$CH$_3$ | H | H | H | H | OCH$_3$ | OCH$_3$ | N |
| CH | SO$_2$CH$_3$ | H | H | H | H | OCH$_3$ | CH$_3$ | N |
| CH | SO$_2$CH$_3$ | H | H | H | H | OC$_2$H$_5$ | NHCH$_3$ | N |
| CH | SO$_2$CH$_3$ | H | H | H | CH$_3$ | OCH$_3$ | CH$_3$ | N |
| CH | SO$_2$N(CH$_3$)$_2$ | H | H | H | H | OCH$_3$ | OCH$_3$ | CH |
| CH | SO$_2$N(CH$_3$)$_2$ | H | H | H | H | OCH$_3$ | CH$_3$ | CH |
| CH | SO$_2$N(CH$_3$)$_2$ | H | H | H | H | Cl | OCH$_3$ | CH |
| CH | SO$_2$N(CH$_3$)$_2$ | H | H | H | H | OCH$_3$ | OCH$_3$ | N |
| CH | SO$_2$N(CH$_3$)$_2$ | H | H | H | H | OCH$_3$ | CH$_3$ | N |
| N | CO$_2$CH$_3$ | CH$_3$ | CH$_3$ | H | H | OCH$_3$ | OCH$_3$ | CH |
| N | CO$_2$CH$_3$ | CH$_3$ | CH$_3$ | H | H | OCH$_3$ | CH$_3$ | CH |
| N | CO$_2$CH$_3$ | CH$_3$ | CH$_3$ | H | H | Cl | OCH$_3$ | CH |
| N | CO$_2$CH$_3$ | CH$_3$ | CH$_3$ | H | H | CH$_3$ | CH$_3$ | CH |
| N | CO$_2$CH$_3$ | CH$_3$ | CH$_3$ | H | H | OCH$_3$ | OCH$_3$ | N |
| N | CO$_2$CH$_3$ | CH$_3$ | CH$_3$ | H | H | OCH$_3$ | CH$_3$ | N |
| N | CO$_2$CH$_3$ | CH$_3$ | CH$_3$ | H | H | OC$_2$H$_5$ | NHCH$_3$ | N |
| N | CO$_2$CH$_3$ | CH$_3$ | CH$_3$ | H | CH$_3$ | OCH$_3$ | CH$_3$ | N |
| N | CO$_2$CH$_3$ | H | H | H | H | OCH$_3$ | OCH$_3$ | CH |
| N | CO$_2$CH$_3$ | H | H | H | H | OCH$_3$ | CH$_3$ | CH |
| N | CO$_2$CH$_3$ | H | H | H | H | Cl | OCH$_3$ | CH |
| N | CO$_2$CH$_3$ | H | H | H | H | CH$_3$ | CH$_3$ | CH |
| N | CO$_2$CH$_3$ | H | H | H | H | OCH$_3$ | OCH$_3$ | N |
| N | CO$_2$CH$_3$ | H | H | H | H | OCH$_3$ | CH$_3$ | N |
| N | CO$_2$CH$_3$ | H | H | H | H | OC$_2$H$_5$ | NHCH$_3$ | N |
| N | CO$_2$CH$_3$ | H | H | H | CH$_3$ | OCH$_3$ | CH$_3$ | N |
| CH | CO$_2$CH$_3$ | CH$_3$ | CH$_3$ | H | H | OCH$_3$ | OCH$_3$ | CH |
| CH | CO$_2$CH$_3$ | CH$_3$ | CH$_3$ | H | H | OCH$_3$ | CH$_3$ | CH |
| CH | CO$_2$CH$_3$ | CH$_3$ | CH$_3$ | H | H | Cl | OCH$_3$ | CH |
| CH | CO$_2$CH$_3$ | CH$_3$ | CH$_3$ | H | H | CH$_3$ | CH$_3$ | CH |
| CH | CO$_2$CH$_3$ | CH$_3$ | CH$_3$ | H | H | OCH$_3$ | OCH$_3$ | N |
| CH | CO$_2$CH$_3$ | CH$_3$ | CH$_3$ | H | H | OCH$_3$ | CH$_3$ | N |
| CH | CO$_2$CH$_3$ | CH$_3$ | CH$_3$ | H | H | OC$_2$H$_5$ | NHCH$_3$ | N |

TABLE 8-continued

General Formula 8

| $Z^1$ | $R^1$ | $R^2$ | $R^3$ | $R^5$ | R | X | Y | $Z^4$ |
|---|---|---|---|---|---|---|---|---|
| CH | $CO_2CH_3$ | $CH_3$ | $CH_3$ | H | $CH_3$ | $OCH_3$ | $CH_3$ | N |
| CH | $CO_2CH_3$ | H | H | H | H | $OCH_3$ | $OCH_3$ | CH |
| CH | $CO_2CH_3$ | H | H | H | H | $OCH_3$ | $CH_3$ | CH |
| CH | $CO_2CH_3$ | H | H | H | H | Cl | $OCH_3$ | CH |
| CH | $CO_2CH_3$ | H | H | H | H | $CH_3$ | $CH_3$ | CH |
| CH | $CO_2CH_3$ | H | H | H | H | $OCH_3$ | $OCH_3$ | N |
| CH | $CO_2CH_3$ | H | H | H | H | $OCH_3$ | $CH_3$ | N |
| CH | $CO_2CH_3$ | H | H | H | H | $OC_2H_5$ | $NHCH_3$ | N |
| CH | $CO_2CH_3$ | H | H | H | $CH_3$ | $OCH_3$ | $CH_3$ | N |
| N | $CO_2C_2H_5$ | H | H | H | H | $OCH_3$ | $OCH_3$ | CH |
| N | $CO_2C_2H_5$ | H | H | H | H | $OCH_3$ | $CH_3$ | CH |
| N | $CO_2C_2H_5$ | H | H | H | H | Cl | $OCH_3$ | CH |
| N | $CO_2C_2H_5$ | H | H | H | H | $CH_3$ | $CH_3$ | CH |
| N | $CO_2C_2H_5$ | H | H | H | H | $OCH_3$ | $OCH_3$ | N |
| N | $CO_2C_2H_5$ | H | H | H | H | $OCH_3$ | $CH_3$ | N |
| N | $CO_2C_2H_5$ | H | H | H | H | $OC_2H_5$ | $NHCH_3$ | N |
| N | $CO_2C_2H_5$ | H | H | H | $CH_3$ | $OCH_3$ | $CH_3$ | N |
| N | $CO_2C_2H_5$ | $CH_3$ | $CH_3$ | H | H | $OCH_3$ | $OCH_3$ | CH |
| N | $CO_2C_2H_5$ | $CH_3$ | $CH_3$ | H | H | $OCH_3$ | $CH_3$ | CH |
| N | $CO_2C_2H_5$ | $CH_3$ | $CH_3$ | H | H | Cl | $OCH_3$ | CH |
| N | $CO_2C_2H_5$ | $CH_3$ | $CH_3$ | H | H | $CH_3$ | $CH_3$ | CH |
| N | $CO_2C_2H_5$ | $CH_3$ | $CH_3$ | H | H | $OCH_3$ | $OCH_3$ | N |
| N | $CO_2C_2H_5$ | $CH_3$ | $CH_3$ | H | H | $OCH_3$ | $CH_3$ | N |
| N | $CO_2C_2H_5$ | $CH_3$ | $CH_3$ | H | H | $OC_2H_5$ | $NHCH_3$ | N |
| N | $CO_2C_2H_5$ | $CH_3$ | $CH_3$ | H | $CH_3$ | $OCH_3$ | $CH_3$ | N |

TABLE 9

General Formula 9

| $R^1$ | $R^3$ | $R^5$ | R | X | Y | $Z^4$ |
|---|---|---|---|---|---|---|
| H | H | H | H | $OCH_3$ | $OCH_3$ | CH |
| H | H | H | H | $OCH_3$ | $CH_3$ | CH |
| H | H | H | H | Cl | $OCH_3$ | CH |
| H | H | H | H | $CH_3$ | $CH_3$ | CH |
| H | H | H | H | $OCH_3$ | $OCH_3$ | N |
| H | H | H | H | $OCH_3$ | $CH_3$ | N |
| H | H | H | H | $OC_2H_5$ | $NHCH_3$ | N |
| H | H | H | $CH_3$ | $OCH_3$ | $CH_3$ | N |
| Cl | H | H | H | $OCH_3$ | $OCH_3$ | CH |
| Cl | H | H | H | $OCH_3$ | $CH_3$ | CH |
| Cl | H | H | H | Cl | $OCH_3$ | CH |
| Cl | H | H | H | $CH_3$ | $CH_3$ | CH |
| Cl | H | H | H | $OCH_3$ | $OCH_3$ | N |
| Cl | H | H | H | $OCH_3$ | $CH_3$ | N |
| Cl | H | H | H | $OC_2H_5$ | $NHCH_3$ | N |
| Cl | H | H | $CH_3$ | $OCH_3$ | $CH_3$ | N |
| $SO_2CH_3$ | H | H | H | $OCH_3$ | $OCH_3$ | CH |
| $SO_2CH_3$ | H | H | H | $OCH_3$ | $CH_3$ | CH |
| $SO_2CH_3$ | H | H | H | Cl | $OCH_3$ | CH |
| $SO_2CH_3$ | H | H | H | $CH_3$ | $CH_3$ | CH |
| $SO_2CH_3$ | H | H | H | $OCH_3$ | $OCH_3$ | N |
| $SO_2CH_3$ | H | H | H | $OCH_3$ | $CH_3$ | N |
| $SO_2CH_3$ | H | H | H | $OC_2H_5$ | $NHCH_3$ | N |
| $SO_2CH_3$ | H | H | $CH_3$ | $OCH_3$ | $CH_3$ | N |
| $CO_2CH_3$ | H | H | H | $OCH_3$ | $OCH_3$ | CH |
| $CO_2CH_3$ | H | H | H | $OCH_3$ | $CH_3$ | CH |
| $CO_2CH_3$ | H | H | H | Cl | $OCH_3$ | CH |
| $CO_2CH_3$ | H | H | H | $CH_3$ | $CH_3$ | CH |
| $CO_2CH_3$ | H | H | H | $OCH_3$ | $OCH_3$ | N |
| $CO_2CH_3$ | H | H | H | $OCH_3$ | $CH_3$ | N |
| $CO_2CH_3$ | H | H | H | $OC_2H_5$ | $NHCH_3$ | N |
| $CO_2CH_3$ | H | H | $CH_3$ | $OCH_3$ | $CH_3$ | N |
| $CO_2C_2H_5$ | H | H | H | $OCH_3$ | $OCH_3$ | CH |
| $CO_2C_2H_5$ | H | H | H | $OCH_3$ | $CH_3$ | CH |
| $CO_2C_2H_5$ | H | H | H | Cl | $OCH_3$ | CH |
| $CO_2C_2H_5$ | H | H | H | $CH_3$ | $CH_3$ | CH |
| $CO_2C_2H_5$ | H | H | H | $OCH_3$ | $OCH_3$ | N |
| $CO_2C_2H_5$ | H | H | H | $OCH_3$ | $CH_3$ | N |
| $CO_2C_2H_5$ | H | H | H | $OC_2H_5$ | $NHCH_3$ | N |
| $CO_2C_2H_5$ | H | H | $CH_3$ | $OCH_3$ | $CH_3$ | N |
| $SO_2N(CH_3)_2$ | H | H | H | $OCH_3$ | $OCH_3$ | CH |
| $SO_2N(CH_3)_2$ | H | H | H | $OCH_3$ | $CH_3$ | CH |
| $SO_2N(CH_3)_2$ | H | H | H | Cl | $OCH_3$ | CH |
| $SO_2N(CH_3)_2$ | H | H | H | $CH_3$ | $CH_3$ | CH |
| $SO_2N(CH_3)_2$ | H | H | H | $OCH_3$ | $OCH_3$ | N |
| $SO_2N(CH_3)_2$ | H | H | H | $OCH_3$ | $CH_3$ | N |
| $SO_2N(CH_3)_2$ | H | H | H | $OC_2H_5$ | $NHCH_3$ | N |
| $SO_2N(CH_3)_2$ | H | H | $CH_3$ | $OCH_3$ | $CH_3$ | N |
| H | H | H | H | $OCH_3$ | $OCH_3$ | CH |
| H | H | H | H | $OCH_3$ | $CH_3$ | CH |
| H | H | H | H | Cl | $OCH_3$ | CH |
| H | H | H | H | $CH_3$ | $CH_3$ | CH |
| H | H | H | H | $OCH_3$ | $OCH_3$ | N |
| H | H | H | H | $OCH_3$ | $CH_3$ | N |
| H | H | H | H | $OC_2H_5$ | $NHCH_3$ | N |
| H | H | H | $CH_3$ | $OCH_3$ | $CH_3$ | N |
| H | H | Cl | H | $OCH_3$ | $OCH_3$ | CH |
| H | H | Cl | H | $OCH_3$ | $CH_3$ | CH |
| H | H | Cl | H | Cl | $OCH_3$ | CH |
| H | H | Cl | H | $CH_3$ | $CH_3$ | CH |
| H | H | Cl | H | $OCH_3$ | $OCH_3$ | N |
| H | H | Cl | H | $OCH_3$ | $CH_3$ | N |
| H | H | Cl | H | $OC_2H_5$ | $NHCH_3$ | N |
| H | H | Cl | $CH_3$ | $OCH_3$ | $CH_3$ | N |
| H | H | $SO_2CH_3$ | H | $OCH_3$ | $OCH_3$ | CH |
| H | H | $SO_2CH_3$ | H | $OCH_3$ | $CH_3$ | CH |

TABLE 9-continued

General Formula 9

| R¹ | R³ | R⁵ | R | X | Y | Z⁴ |
|---|---|---|---|---|---|---|
| H | H | SO₂CH₃ | H | Cl | OCH₃ | CH |
| H | H | SO₂CH₃ | H | CH₃ | CH₃ | CH |
| H | H | SO₂CH₃ | H | OCH₃ | OCH₃ | N |
| H | H | SO₂CH₃ | H | OCH₃ | CH₃ | N |
| H | H | SO₂CH₃ | H | OC₂H₅ | NHCH₃ | N |
| H | H | SO₂CH₃ | CH₃ | OCH₃ | CH₃ | N |
| H | H | CO₂CH₃ | H | OCH₃ | OCH₃ | CH |
| H | H | CO₂CH₃ | H | Cl | OCH₃ | CH |
| H | H | CO₂CH₃ | H | CH₃ | CH₃ | CH |
| H | H | CO₂CH₃ | H | OCH₃ | OCH₃ | N |
| H | H | CO₂CH₃ | H | OCH₃ | CH₃ | N |
| H | H | CO₂CH₃ | H | OC₂H₅ | NHCH₃ | N |
| H | H | CO₂CH₃ | CH₃ | OCH₃ | CH₃ | N |
| H | H | CO₂C₂H₅ | H | OCH₃ | OCH₃ | CH |
| H | H | CO₂C₂H₅ | H | Cl | OCH₃ | CH |
| H | H | CO₂C₂H₅ | H | CH₃ | CH₃ | CH |
| H | H | CO₂C₂H₅ | H | OCH₃ | OCH₃ | N |
| H | H | CO₂C₂H₅ | H | OCH₃ | CH₃ | N |
| H | H | CO₂C₂H₅ | H | OC₂H₅ | NHCH₃ | N |
| H | H | CO₂C₂H₅ | CH₃ | OCH₃ | CH₃ | N |
| H | H | SO₂N(CH₃)₂ | H | OCH₃ | OCH₃ | CH |
| H | H | SO₂N(CH₃)₂ | H | OCH₃ | CH₃ | CH |
| H | H | SO₂N(CH₃)₂ | H | Cl | OCH₃ | CH |
| H | H | SO₂N(CH₃)₂ | H | CH₃ | CH₃ | CH |
| H | H | SO₂N(CH₃)₂ | H | OCH₃ | OCH₃ | N |
| H | H | SO₂N(CH₃)₂ | H | OCH₃ | CH₃ | N |
| H | H | SO₂N(CH₃)₂ | H | OC₂H₅ | NHCH₃ | N |
| H | H | SO₂N(CH₃)₂ | CH₃ | OCH₃ | CH₃ | N |

TABLE 10

General Formula 10

| Z | R² | R³ | R⁵ | R | X | Y | Z⁴ |
|---|---|---|---|---|---|---|---|
| CH | H | H | H | H | OCH₃ | OCH₃ | CH |
| CH | H | H | H | H | OCH₃ | CH₃ | CH |
| CH | H | H | H | H | Cl | OCH₃ | CH |
| CH | H | H | H | H | CH₃ | CH₃ | CH |
| CH | H | H | H | H | OCH₃ | OCH₃ | N |
| CH | H | H | H | H | OCH₃ | CH₃ | N |
| CH | H | H | H | H | OC₂H₅ | NHCH₃ | N |
| CH | H | H | H | CH₃ | OCH₃ | CH₃ | N |
| CH | H | H | Cl | H | OCH₃ | OCH₃ | CH |
| CH | H | H | Cl | H | OCH₃ | CH₃ | CH |
| CH | H | H | Cl | H | Cl | OCH₃ | CH |
| CH | H | H | Cl | H | CH₃ | CH₃ | CH |
| CH | H | H | Cl | H | OCH₃ | OCH₃ | N |
| CH | H | H | Cl | H | OCH₃ | CH₃ | N |
| CH | H | H | Cl | H | OC₂H₅ | NHCH₃ | N |
| CH | H | H | Cl | CH₃ | OCH₃ | CH₃ | N |
| CH | H | H | SO₂CH₃ | H | OCH₃ | OCH₃ | CH |
| CH | H | H | SO₂CH₃ | H | OCH₃ | CH₃ | CH |
| CH | H | H | SO₂CH₃ | H | Cl | OCH₃ | CH |
| CH | H | H | SO₂CH₃ | H | CH₃ | CH₃ | CH |
| CH | H | H | SO₂CH₃ | H | OCH₃ | OCH₃ | N |
| CH | H | H | SO₂CH₃ | H | OCH₃ | CH₃ | N |
| CH | H | H | SO₂CH₃ | H | OC₂H₅ | NHCH₃ | N |
| CH | H | H | SO₂CH₃ | CH₃ | OCH₃ | CH₃ | N |
| N | H | H | H | H | OCH₃ | OCH₃ | CH |
| N | H | H | H | H | OCH₃ | CH₃ | CH |
| N | H | H | H | H | Cl | OCH₃ | CH |
| N | H | H | H | H | CH₃ | CH₃ | CH |
| N | H | H | H | H | OCH₃ | OCH₃ | N |
| N | H | H | H | H | OCH₃ | CH₃ | N |
| N | H | H | H | H | OC₂H₅ | NHCH₃ | N |
| N | H | H | H | CH₃ | OCH₃ | CH₃ | N |
| N | H | H | Cl | H | OCH₃ | OCH₃ | CH |
| N | H | H | Cl | H | OCH₃ | CH₃ | CH |
| N | H | H | Cl | H | Cl | OCH₃ | CH |
| N | H | H | Cl | H | CH₃ | CH₃ | CH |
| N | H | H | Cl | H | OCH₃ | OCH₃ | N |
| N | H | H | Cl | H | OCH₃ | CH₃ | N |
| N | H | H | Cl | H | OC₂H₅ | NHCH₃ | N |
| N | H | H | Cl | CH₃ | OCH₃ | CH₃ | N |
| N | H | H | SO₂CH₃ | H | OCH₃ | OCH₃ | CH |
| N | H | H | SO₂CH₃ | H | OCH₃ | CH₃ | CH |
| N | H | H | SO₂CH₃ | H | Cl | OCH₃ | CH |
| N | H | H | SO₂CH₃ | H | CH₃ | CH₃ | CH |
| N | H | H | SO₂CH₃ | H | OCH₃ | OCH₃ | N |
| N | H | H | SO₂CH₃ | H | OCH₃ | CH₃ | N |
| N | H | H | SO₂CH₃ | H | OC₂H₅ | NHCH₃ | N |
| N | H | H | SO₂CH₃ | CH₃ | OCH₃ | CH₃ | N |
| CH | H | H | CO₂CH₃ | H | OCH₃ | OCH₃ | CH |
| CH | H | H | CO₂CH₃ | H | OCH₃ | CH₃ | CH |
| CH | H | H | CO₂CH₃ | H | Cl | OCH₃ | CH |
| CH | H | H | CO₂CH₃ | H | CH₃ | CH₃ | CH |
| CH | H | H | CO₂CH₃ | H | OCH₃ | OCH₃ | N |
| CH | H | H | CO₂CH₃ | H | OCH₃ | CH₃ | N |
| CH | H | H | CO₂CH₃ | H | OC₂H₅ | NHCH₃ | N |
| CH | H | H | CO₂CH₃ | CH₃ | OCH₃ | CH₃ | N |
| CH | H | H | CO₂C₂H₅ | H | OCH₃ | OCH₃ | CH |
| CH | H | H | CO₂C₂H₅ | H | OCH₃ | CH₃ | CH |
| CH | H | H | CO₂C₂H₅ | H | Cl | OCH₃ | CH |
| CH | H | H | CO₂C₂H₅ | H | CH₃ | CH₃ | CH |
| CH | H | H | CO₂C₂H₅ | H | OCH₃ | OCH₃ | N |
| CH | H | H | CO₂C₂H₅ | H | OCH₃ | CH₃ | N |
| CH | H | H | CO₂C₂H₅ | H | OC₂H₅ | NHCH₃ | N |
| CH | H | H | CO₂C₂H₅ | CH₃ | OCH₃ | CH₃ | N |
| CH | H | H | SO₂N(CH₃)₂ | H | OCH₃ | OCH₃ | CH |
| CH | H | H | SO₂N(CH₃)₂ | H | OCH₃ | CH₃ | CH |
| CH | H | H | SO₂N(CH₃)₂ | H | Cl | OCH₃ | CH |
| CH | H | H | SO₂N(CH₃)₂ | H | CH₃ | CH₃ | CH |
| CH | H | H | SO₂N(CH₃)₂ | H | OCH₃ | OCH₃ | N |
| CH | H | H | SO₂N(CH₃)₂ | H | OCH₃ | CH₃ | N |
| CH | H | H | SO₂N(CH₃)₂ | H | OC₂H₅ | NHCH₃ | N |
| CH | H | H | SO₂N(CH₃)₂ | CH₃ | OCH₃ | CH₃ | N |
| N | H | H | CO₂CH₃ | H | OCH₃ | OCH₃ | CH |
| N | H | H | CO₂CH₃ | H | OCH₃ | CH₃ | CH |
| N | H | H | CO₂CH₃ | H | Cl | OCH₃ | CH |
| N | H | H | CO₂CH₃ | H | CH₃ | CH₃ | CH |
| N | H | H | CO₂CH₃ | H | OCH₃ | OCH₃ | N |
| N | H | H | CO₂CH₃ | H | OCH₃ | CH₃ | N |
| N | H | H | CO₂CH₃ | H | OC₂H₅ | NHCH₃ | N |
| N | H | H | CO₂CH₃ | CH₃ | OCH₃ | CH₃ | N |
| N | H | H | CO₂C₂H₅ | H | OCH₃ | OCH₃ | CH |
| N | H | H | CO₂C₂H₅ | H | OCH₃ | CH₃ | CH |
| N | H | H | CO₂C₂H₅ | H | Cl | OCH₃ | CH |
| N | H | H | CO₂C₂H₅ | H | CH₃ | CH₃ | CH |
| N | H | H | CO₂C₂H₅ | H | OCH₃ | OCH₃ | N |
| N | H | H | CO₂C₂H₅ | H | OCH₃ | CH₃ | N |
| N | H | H | CO₂C₂H₅ | H | OC₂H₅ | NHCH₃ | N |
| N | H | H | CO₂C₂H₅ | CH₃ | OCH₃ | CH₃ | N |
| N | H | H | SO₂N(CH₃)₂ | H | OCH₃ | OCH₃ | CH |
| N | H | H | SO₂N(CH₃)₂ | H | OCH₃ | CH₃ | CH |
| N | H | H | SO₂N(CH₃)₂ | H | Cl | OCH₃ | CH |
| N | H | H | SO₂N(CH₃)₂ | H | CH₃ | CH₃ | CH |
| N | H | H | SO₂N(CH₃)₂ | H | OCH₃ | OCH₃ | N |
| N | H | H | SO₂N(CH₃)₂ | H | OCH₃ | CH₃ | N |
| N | H | H | SO₂N(CH₃)₂ | H | OC₂H₅ | NHCH₃ | N |
| N | H | H | SO₂N(CH₃)₂ | CH₃ | OCH₃ | CH₃ | N |

TABLE 11

General Formula 11

| R³ | R⁵ | R | X | Y | Z⁴ | M.P. (°C.) |
|---|---|---|---|---|---|---|
| H | H | H | OCH₃ | OCH₃ | CH | |
| H | H | H | OCH₃ | CH₃ | CH | |
| H | H | H | Cl | OCH₃ | CH | |
| H | H | H | CH₃ | CH₃ | CH | |
| H | H | H | OCH₃ | OCH₃ | N | |
| H | H | H | OCH₃ | CH₃ | N | |
| H | H | H | OC₂H₅ | NHCH₃ | N | |
| H | H | CH₃ | OCH₃ | CH₃ | N | |
| H | Cl | H | OCH₃ | OCH₃ | CH | |
| H | Cl | H | OCH₃ | CH₃ | CH | |
| H | Cl | H | Cl | OCH₃ | CH | |
| H | Cl | H | CH₃ | CH₃ | CH | |
| H | Cl | H | OCH₃ | OCH₃ | N | |
| H | Cl | H | OCH₃ | CH₃ | N | |
| H | Cl | H | OC₂H₅ | NHCH₃ | N | |
| H | Cl | CH₃ | OCH₃ | CH₃ | N | |
| H | SO₂CH₃ | H | OCH₃ | OCH₃ | CH | |
| H | SO₂CH₃ | H | OCH₃ | CH₃ | CH | |
| H | SO₂CH₃ | H | Cl | OCH₃ | CH | |

TABLE 11-continued

General Formula 11

| R³ | R⁵ | R | X | Y | Z⁴ | M.P. (°C.) |
|---|---|---|---|---|---|---|
| H | SO₂CH₃ | H | CH₃ | CH₃ | CH | |
| H | SO₂CH₃ | H | OCH₃ | OCH₃ | N | |
| H | SO₂CH₃ | H | OCH₃ | CH₃ | N | |
| H | SO₂CH₃ | H | OC₂H₅ | NHCH₃ | N | |
| H | SO₂CH₃ | CH₃ | OCH₃ | CH₃ | N | |
| H | CO₂CH₃ | H | OCH₃ | OCH₃ | CH | |
| H | CO₂CH₃ | H | OCH₃ | CH₃ | CH | |
| H | CO₂CH₃ | H | Cl | OCH₃ | CH | |
| H | CO₂CH₃ | H | CH₃ | CH₃ | CH | |
| H | CO₂CH₃ | H | OCH₃ | OCH₃ | N | |
| H | CO₂CH₃ | H | OCH₃ | CH₃ | N | |
| H | CO₂CH₃ | H | OC₂H₅ | NHCH₃ | N | |
| H | CO₂CH₃ | CH₃ | OCH₃ | CH₃ | N | |
| H | CO₂C₂H₅ | H | OCH₃ | OCH₃ | CH | |
| H | CO₂C₂H₅ | H | OCH₃ | CH₃ | CH | |
| H | CO₂C₂H₅ | H | Cl | OCH₃ | CH | |
| H | CO₂C₂H₅ | H | CH₃ | CH₃ | CH | |
| H | CO₂C₂H₅ | H | OCH₃ | OCH₃ | N | |
| H | CO₂C₂H₅ | H | OCH₃ | CH₃ | N | |
| H | CO₂C₂H₅ | H | OC₂H₅ | NHCH₃ | N | |
| H | CO₂C₂H₅ | CH₃ | OCH₃ | CH₃ | N | |
| H | SO₂N(CH₃)₂ | H | OCH₃ | OCH₃ | CH | |
| H | SO₂N(CH₃)₂ | H | OCH₃ | CH₃ | CH | |
| H | SO₂N(CH₃)₂ | H | Cl | OCH₃ | CH | |
| H | SO₂N(CH₃)₂ | H | CH₃ | CH₃ | CH | |
| H | SO₂N(CH₃)₂ | H | OCH₃ | OCH₃ | N | |
| H | SO₂N(CH₃)₂ | H | OCH₃ | CH₃ | N | |
| H | SO₂N(CH₃)₂ | H | OC₂H₅ | NHCH₃ | N | |
| H | SO₂N(CH₃)₂ | CH₃ | OCH₃ | CH₃ | N | |

TABLE 12

| R¹ | R² | R⁴ | R | X | Y | Z⁴ |
|---|---|---|---|---|---|---|
| H | H | H | H | OCH₃ | OCH₃ | CH |
| H | H | H | H | OCH₃ | CH₃ | CH |
| H | H | H | H | Cl | OCH₃ | CH |
| H | H | H | H | CH₃ | CH₃ | CH |
| H | H | H | H | OCH₃ | OCH₃ | N |
| H | H | H | H | OCH₃ | CH₃ | N |
| H | H | H | H | OC₂H₅ | NHCH₃ | N |
| H | — | H | CH₃ | OCH₃ | CH₃ | N |
| Cl | H | H | H | OCH₃ | OCH₃ | CH |
| Cl | H | H | H | OCH₃ | CH₃ | CH |
| Cl | H | H | H | Cl | OCH₃ | CH |
| Cl | H | H | H | CH₃ | CH₃ | CH |
| Cl | H | H | H | OCH₃ | OCH₃ | N |
| Cl | H | H | H | OCH₃ | CH₃ | N |
| Cl | H | H | H | OC₂H₅ | NHCH₃ | N |
| Cl | H | H | CH₃ | OCH₃ | CH₃ | N |
| SO₂CH₃ | H | H | H | OCH₃ | OCH₃ | CH |
| SO₂CH₃ | H | H | H | OCH₃ | CH₃ | CH |
| SO₂CH₃ | H | H | H | Cl | OCH₃ | CH |
| SO₂CH₃ | H | H | H | CH₃ | CH₃ | CH |
| SO₂CH₃ | H | H | H | OCH₃ | OCH₃ | N |
| SO₂CH₃ | H | H | H | OCH₃ | CH₃ | N |
| SO₂CH₃ | H | H | H | OC₂H₅ | NHCH₃ | N |
| SO₂CH₃ | H | H | CH₃ | OCH₃ | CH₃ | N |
| CO₂CH₃ | H | H | H | OCH₃ | OCH₃ | CH |
| CO₂CH₃ | H | H | H | OCH₃ | CH₃ | CH |
| CO₂CH₃ | H | H | H | Cl | OCH₃ | CH |
| CO₂CH₃ | H | H | H | CH₃ | CH₃ | CH |
| CO₂CH₃ | H | H | H | OCH₃ | OCH₃ | N |
| CO₂CH₃ | H | H | H | OCH₃ | CH₃ | N |
| CO₂CH₃ | H | H | H | OC₂H₅ | NHCH₃ | N |
| CO₂CH₃ | H | H | CH₃ | OCH₃ | CH₃ | N |
| CO₂C₂H₅ | H | H | H | OCH₃ | OCH₃ | CH |
| CO₂C₂H₅ | H | H | H | OCH₃ | CH₃ | CH |
| CO₂C₂H₅ | H | H | H | Cl | OCH₃ | CH |
| CO₂C₂H₅ | H | H | H | CH₃ | CH₃ | CH |
| CO₂C₂H₅ | H | H | H | OCH₃ | OCH₃ | N |
| CO₂C₂H₅ | H | H | H | OCH₃ | CH₃ | N |
| CO₂C₂H₅ | H | H | H | OC₂H₅ | NHCH₃ | N |
| CO₂C₂H₅ | H | H | CH₃ | OCH₃ | CH₃ | N |
| SO₂N(CH₃)₂ | H | H | H | OCH₃ | OCH₃ | CH |
| SO₂N(CH₃)₂ | H | H | H | OCH₃ | CH₃ | CH |
| SO₂N(CH₃)₂ | H | H | H | Cl | OCH₃ | CH |
| SO₂N(CH₃)₂ | H | H | H | CH₃ | CH₃ | CH |

TABLE 12-continued

| R¹ | R² | R⁴ | R | X | Y | Z⁴ |
|---|---|---|---|---|---|---|
| SO₂N(CH₃)₂ | H | H | H | OCH₃ | OCH₃ | N |
| SO₂N(CH₃)₂ | H | H | H | OCH₃ | CH₃ | N |
| SO₂N(CH₃)₂ | H | H | H | OC₂H₅ | NHCH₃ | N |
| SO₂N(CH₃)₂ | H | H | CH₃ | OCH₃ | CH₃ | N |

TABLE 13

General Formula 13

| R² | R⁴ | R | X | Y | Z⁴ |
|---|---|---|---|---|---|
| H | H | H | OCH₃ | OCH₃ | CH |
| H | H | H | OCH₃ | CH₃ | CH |
| H | H | H | Cl | OCH₃ | CH |
| H | H | H | CH₃ | CH₃ | CH |
| H | H | H | OCH₃ | OCH₃ | N |
| H | H | H | OCH₃ | CH₃ | N |
| H | H | H | OC₂H₅ | NHCH₃ | N |
| H | H | CH₃ | OCH₃ | CH₃ | N |
| CH₃ | H | H | OCH₃ | OCH₃ | CH |
| CH₃ | H | H | OCH₃ | CH₃ | CH |
| CH₃ | H | H | Cl | OCH₃ | CH |
| CH₃ | H | H | CH₃ | CH₃ | CH |
| CH₃ | H | H | OCH₃ | OCH₃ | N |
| CH₃ | H | H | OCH₃ | CH₃ | N |
| CH₃ | H | H | OC₂H₅ | NHCH₃ | N |
| CH₃ | H | CH₃ | OCH₃ | CH₃ | N |
| OCH₃ | H | H | OCH₃ | OCH₃ | CH |
| OCH₃ | H | H | OCH₃ | CH₃ | CH |
| OCH₃ | H | H | Cl | OCH₃ | CH |
| OCH₃ | H | H | CH₃ | CH₃ | CH |
| OCH₃ | H | H | OCH₃ | OCH₃ | N |
| OCH₃ | H | H | OCH₃ | CH₃ | N |
| OCH₃ | H | H | OC₂H₅ | NHCH₃ | N |
| OCH₃ | H | CH | OCH₃ | CH₃ | N |

TABLE 14

General Formula 14

| R¹ | R² | R⁴ | R | X | Y | Z⁴ |
|---|---|---|---|---|---|---|
| H | H | H | H | OCH₃ | OCH₃ | CH |
| H | H | H | H | OCH₃ | CH₃ | CH |
| H | H | H | H | Cl | OCH₃ | CH |
| H | H | H | H | CH₃ | CH₃ | CH |
| H | H | H | H | OCH₃ | OCH₃ | N |
| H | H | H | H | OCH₃ | CH₃ | N |
| H | H | H | H | OC₂H₅ | NHCH₃ | N |
| H | H | H | CH₃ | OCH₃ | CH₃ | N |
| Cl | H | H | H | OCH₃ | OCH₃ | CH |
| Cl | H | H | H | OCH₃ | CH₃ | CH |
| Cl | H | H | H | Cl | OCH₃ | CH |
| Cl | H | H | H | CH₃ | CH₃ | CH |
| Cl | H | H | H | OCH₃ | OCH₃ | N |
| Cl | H | H | H | OCH₃ | CH₃ | N |
| Cl | H | H | H | OC₂H₅ | NHCH₃ | N |
| Cl | H | H | CH₃ | OCH₃ | CH₃ | N |
| SO₂CH₃ | H | H | H | OCH₃ | OCH₃ | CH |
| SO₂CH₃ | H | H | H | OCH₃ | CH₃ | CH |
| SO₂CH₃ | H | H | H | Cl | OCH₃ | CH |
| SO₂CH₃ | H | H | H | CH₃ | CH₃ | CH |
| SO₂CH₃ | H | H | H | OCH₃ | OCH₃ | N |
| SO₂CH₃ | H | H | H | OCH₃ | CH₃ | N |
| SO₂CH₃ | H | H | H | OC₂H₅ | NHCH₃ | N |
| SO₂CH₃ | H | H | CH₃ | OCH₃ | CH₃ | N |
| CO₂CH₃ | H | H | H | OCH₃ | OCH₃ | CH |
| CO₂CH₃ | H | H | H | OCH₃ | CH₃ | CH |
| CO₂CH₃ | H | H | H | Cl | OCH₃ | CH |
| CO₂CH₃ | H | H | H | CH₃ | CH₃ | CH |
| CO₂CH₃ | H | H | H | OCH₃ | OCH₃ | N |
| CO₂CH₃ | H | H | H | OCH₃ | CH₃ | N |
| CO₂CH₃ | H | H | H | OC₂H₅ | NHCH₃ | N |
| CO₂CH₃ | H | H | CH₃ | OCH₃ | CH₃ | N |
| CO₂C₂H₅ | H | H | H | OCH₃ | OCH₃ | CH |
| CO₂C₂H₅ | H | H | H | OCH₃ | CH₃ | CH |
| CO₂C₂H₅ | H | H | H | Cl | OCH₃ | CH |
| CO₂C₂H₅ | H | H | H | CH₃ | CH₃ | CH |
| CO₂C₂H₅ | H | H | H | OCH₃ | OCH₃ | N |
| CO₂C₂H₅ | H | H | H | OCH₃ | CH₃ | N |
| CO₂C₂H₅ | H | H | H | OC₂H₅ | NHCH₃ | N |

TABLE 14-continued

General Formula 14

| R$^1$ | R$^2$ | R$^4$ | R | X | Y | Z$^4$ |
|---|---|---|---|---|---|---|
| CO$_2$C$_2$H$_5$ | H | H | CH$_3$ | OCH$_3$ | CH$_3$ | N |
| SO$_2$N(CH$_3$)$_2$ | H | H | H | OCH$_3$ | OCH$_3$ | CH |
| SO$_2$N(CH$_3$)$_2$ | H | H | H | OCH$_3$ | CH$_3$ | CH |
| SO$_2$N(CH$_3$)$_2$ | H | H | H | Cl | OCH$_3$ | CH |
| SO$_2$N(CH$_3$)$_2$ | H | H | H | CH$_3$ | CH$_3$ | CH |
| SO$_2$N(CH$_3$)$_2$ | H | H | H | OCH$_3$ | OCH$_3$ | N |
| SO$_2$N(CH$_3$)$_2$ | H | H | H | OCH$_3$ | CH$_3$ | N |
| SO$_2$N(CH$_3$)$_2$ | H | H | H | OC$_2$H$_5$ | NHCH$_3$ | N |
| SO$_2$N(CH$_3$)$_2$ | H | H | CH$_3$ | OCH$_3$ | CH$_3$ | N |

TABLE 15

General Formula 15

| Z$^1$ | R$^1$ | R$^2$ | R | X | Y | Z$^4$ |
|---|---|---|---|---|---|---|
| CH | H | H | H | OCH$_3$ | OCH$_3$ | CH |
| CH | H | H | H | OCH$_3$ | CH$_3$ | CH |
| CH | H | H | H | Cl | OCH$_3$ | CH |
| CH | H | H | H | CH$_3$ | CH$_3$ | CH |
| CH | H | H | H | OCH$_3$ | OCH$_3$ | N |
| CH | H | H | H | OCH$_3$ | CH$_3$ | N |
| CH | H | H | H | OC$_2$H$_5$ | NHCH$_3$ | N |
| CH | H | H | CH$_3$ | OCH$_3$ | CH$_3$ | N |
| CH | Cl | H | H | OCH$_3$ | OCH$_3$ | CH |
| CH | Cl | H | H | OCH$_3$ | CH$_3$ | CH |
| CH | Cl | H | H | Cl | OCH$_3$ | CH |
| CH | Cl | H | H | CH$_3$ | CH$_3$ | CH |
| CH | Cl | H | H | OCH$_3$ | OCH$_3$ | N |
| CH | Cl | H | H | OCH$_3$ | CH$_3$ | N |
| CH | Cl | H | H | OC$_2$H$_5$ | NHCH$_3$ | N |
| CH | Cl | H | CH$_3$ | OCH$_3$ | CH$_3$ | N |
| CH | SO$_2$CH$_3$ | H | H | OCH$_3$ | OCH$_3$ | CH |
| CH | SO$_2$CH$_3$ | H | H | OCH$_3$ | CH$_3$ | CH |
| CH | SO$_2$CH$_3$ | H | H | Cl | OCH$_3$ | CH |
| CH | SO$_2$CH$_3$ | H | H | CH$_3$ | CH$_3$ | CH |
| CH | SO$_2$CH$_3$ | H | H | OCH$_3$ | OCH$_3$ | N |
| CH | SO$_2$CH$_3$ | H | H | OCH$_3$ | CH$_3$ | N |
| CH | SO$_2$CH$_3$ | H | H | OC$_2$H$_5$ | NHCH$_3$ | N |
| CH | SO$_2$CH$_3$ | H | CH$_3$ | OCH$_3$ | CH$_3$ | N |
| CH | CO$_2$CH$_3$ | H | H | OCH$_3$ | OCH$_3$ | CH |
| CH | CO$_2$CH$_3$ | H | H | OCH$_3$ | CH$_3$ | CH |
| CH | CO$_2$CH$_3$ | H | H | Cl | OCH$_3$ | CH |
| CH | CO$_2$CH$_3$ | H | H | CH$_3$ | CH$_3$ | CH |
| CH | CO$_2$CH$_3$ | H | H | OCH$_3$ | OCH$_3$ | N |
| CH | CO$_2$CH$_3$ | H | H | OCH$_3$ | CH$_3$ | N |
| CH | CO$_2$CH$_3$ | H | H | OC$_2$H$_5$ | NHCH$_3$ | N |
| CH | CO$_2$CH$_3$ | H | CH$_3$ | OCH$_3$ | CH$_3$ | N |
| CH | CO$_2$C$_2$H$_5$ | H | H | OCH$_3$ | OCH$_3$ | CH |
| CH | CO$_2$C$_2$H$_5$ | H | H | OCH$_3$ | CH$_3$ | CH |
| CH | CO$_2$C$_2$H$_5$ | H | H | Cl | OCH$_3$ | CH |
| CH | CO$_2$C$_2$H$_5$ | H | H | CH$_3$ | CH$_3$ | CH |
| CH | CO$_2$C$_2$H$_5$ | H | H | OCH$_3$ | OCH$_3$ | N |
| CH | CO$_2$C$_2$H$_5$ | H | H | OCH$_3$ | CH$_3$ | N |
| CH | CO$_2$C$_2$H$_5$ | H | H | OC$_2$H$_5$ | NHCH$_3$ | N |
| CH | CO$_2$C$_2$H$_5$ | H | CH$_3$ | OCH$_3$ | CH$_3$ | N |
| CH | SO$_2$N(CH$_3$)$_2$ | H | H | OCH$_3$ | OCH$_3$ | CH |
| CH | SO$_2$N(CH$_3$)$_2$ | H | H | OCH$_3$ | CH$_3$ | CH |
| CH | SO$_2$N(CH$_3$)$_2$ | H | H | Cl | OCH$_3$ | CH |
| CH | SO$_2$N(CH$_3$)$_2$ | H | H | CH$_3$ | CH$_3$ | CH |
| CH | SO$_2$N(CH$_3$)$_2$ | H | H | OCH$_3$ | OCH$_3$ | N |
| CH | SO$_2$N(CH$_3$)$_2$ | H | H | OCH$_3$ | CH$_3$ | N |
| CH | SO$_2$N(CH$_3$)$_2$ | H | H | OC$_2$H$_5$ | NHCH$_3$ | N |
| CH | SO$_2$N(CH$_3$)$_2$ | H | CH$_3$ | OCH$_3$ | CH$_3$ | N |
| N | H | H | H | OCH$_3$ | OCH$_3$ | CH |
| N | H | H | H | OCH$_3$ | CH$_3$ | CH |
| N | H | H | H | Cl | OCH$_3$ | CH |
| N | H | H | H | CH$_3$ | CH$_3$ | CH |
| N | H | H | H | OCH$_3$ | OCH$_3$ | N |
| N | H | H | H | OCH$_3$ | CH$_3$ | N |
| N | H | H | H | OC$_2$H$_5$ | NHCH$_3$ | N |
| N | H | H | CH$_3$ | OCH$_3$ | CH$_3$ | N |
| N | Cl | H | H | OCH$_3$ | OCH$_3$ | CH |
| N | Cl | H | H | OCH$_3$ | CH$_3$ | CH |
| N | Cl | H | H | Cl | OCH$_3$ | CH |
| N | Cl | H | H | CH$_3$ | CH$_3$ | CH |
| N | Cl | H | H | OCH$_3$ | OCH$_3$ | N |
| N | Cl | H | H | OCH$_3$ | CH$_3$ | N |
| N | Cl | H | H | OC$_2$H$_5$ | NHCH$_3$ | N |
| N | Cl | H | CH$_3$ | OCH$_3$ | CH$_3$ | N |
| N | SO$_2$CH$_3$ | H | H | OCH$_3$ | OCH$_3$ | CH |
| N | SO$_2$CH$_3$ | H | H | OCH$_3$ | CH$_3$ | CH |
| N | SO$_2$CH$_3$ | H | H | Cl | OCH$_3$ | CH |
| N | SO$_2$CH$_3$ | H | H | CH$_3$ | CH$_3$ | CH |
| N | SO$_2$CH$_3$ | H | H | OCH$_3$ | OCH$_3$ | N |
| N | SO$_2$CH$_3$ | H | H | OCH$_3$ | CH$_3$ | N |
| N | SO$_2$CH$_3$ | H | H | OC$_2$H$_5$ | NHCH$_3$ | N |
| N | SO$_2$CH$_3$ | H | CH$_3$ | OCH$_3$ | CH$_3$ | N |
| N | CO$_2$CH$_3$ | H | H | OCH$_3$ | OCH$_3$ | CH |
| N | CO$_2$CH$_3$ | H | H | OCH$_3$ | CH$_3$ | CH |
| N | CO$_2$CH$_3$ | H | H | Cl | OCH$_3$ | CH |
| N | CO$_2$CH$_3$ | H | H | CH$_3$ | CH$_3$ | CH |
| N | CO$_2$CH$_3$ | H | H | OCH$_3$ | OCH$_3$ | N |
| N | CO$_2$CH$_3$ | H | H | OCH$_3$ | CH$_3$ | N |
| N | CO$_2$CH$_3$ | H | H | OC$_2$H$_5$ | NHCH$_3$ | N |
| N | CO$_2$CH$_3$ | H | CH$_3$ | OCH$_3$ | CH$_3$ | N |
| N | CO$_2$C$_2$H$_5$ | H | H | OCH$_3$ | OCH$_3$ | CH |
| N | CO$_2$C$_2$H$_5$ | H | H | OCH$_3$ | CH$_3$ | CH |
| N | CO$_2$C$_2$H$_5$ | H | H | Cl | OCH$_3$ | CH |
| N | CO$_2$C$_2$H$_5$ | H | H | CH$_3$ | CH$_3$ | CH |
| N | CO$_2$C$_2$H$_5$ | H | H | OCH$_3$ | OCH$_3$ | N |
| N | CO$_2$C$_2$H$_5$ | H | H | OCH$_3$ | CH$_3$ | N |
| N | CO$_2$C$_2$H$_5$ | H | H | OC$_2$H$_5$ | NHCH$_3$ | N |
| N | CO$_2$C$_2$H$_5$ | H | CH$_3$ | OCH$_3$ | CH$_3$ | N |
| N | SO$_2$N(CH$_3$)$_2$ | H | H | OCH$_3$ | OCH$_3$ | CH |
| N | SO$_2$N(CH$_3$)$_2$ | H | H | OCH$_3$ | CH$_3$ | CH |
| N | SO$_2$N(CH$_3$)$_2$ | H | H | Cl | OCH$_3$ | CH |
| N | SO$_2$N(CH$_3$)$_2$ | H | H | CH$_3$ | CH$_3$ | CH |
| N | SO$_2$N(CH$_3$)$_2$ | H | H | OCH$_3$ | OCH$_3$ | N |
| N | SO$_2$N(CH$_3$)$_2$ | H | H | OCH$_3$ | CH$_3$ | N |
| N | SO$_2$N(CH$_3$)$_2$ | H | H | OC$_2$H$_5$ | NHCH$_3$ | N |
| N | SO$_2$N(CH$_3$)$_2$ | H | CH$_3$ | OCH$_3$ | CH$_3$ | N |

TABLE 16

General Formula 16

| Z$^1$ | R$^2$ | R$^4$ | R | X | Y | Z$^4$ |
|---|---|---|---|---|---|---|
| CH | H | H | H | OCH$_3$ | OCH$_3$ | CH |
| CH | H | H | H | Cl | OCH$_3$ | CH |
| CH | H | H | H | CH$_3$ | CH$_3$ | CH |
| CH | H | H | H | OCH$_3$ | OCH$_3$ | N |
| CH | H | H | H | OCH$_3$ | CH$_3$ | N |
| CH | H | H | H | OC$_2$H$_5$ | NHCH$_3$ | N |
| CH | H | H | CH$_3$ | OCH$_3$ | CH$_3$ | N |
| CH | CH$_3$ | H | H | OCH$_3$ | OCH$_3$ | CH |
| CH | CH$_3$ | H | H | OCH$_3$ | CH$_3$ | CH |
| CH | CH$_3$ | H | H | Cl | OCH$_3$ | CH |
| CH | CH$_3$ | H | H | CH$_3$ | CH$_3$ | CH |
| CH | CH$_3$ | H | H | OCH$_3$ | OCH$_3$ | N |
| CH | CH$_3$ | H | H | OCH$_3$ | CH$_3$ | N |
| CH | CH$_3$ | H | H | OC$_2$H$_5$ | NHCH$_3$ | N |
| CH | CH$_3$ | H | CH$_3$ | OCH$_3$ | CH$_3$ | N |
| CH | OCH$_3$ | H | H | OCH$_3$ | OCH$_3$ | CH |
| CH | OCH$_3$ | H | H | OCH$_3$ | CH$_3$ | CH |
| CH | OCH$_3$ | H | H | Cl | OCH$_3$ | CH |
| CH | OCH$_3$ | H | H | CH$_3$ | CH$_3$ | CH |
| CH | OCH$_3$ | H | H | OCH$_3$ | OCH$_3$ | N |
| CH | OCH$_3$ | H | H | OCH$_3$ | CH$_3$ | N |
| CH | OCH$_3$ | H | H | OC$_2$H$_5$ | NHCH$_3$ | N |
| CH | OCH$_3$ | H | CH$_3$ | OCH$_3$ | CH$_3$ | N |
| N | H | H | H | OCH$_3$ | OCH$_3$ | CH |
| N | H | H | H | Cl | OCH$_3$ | CH |
| N | H | H | H | CH$_3$ | CH$_3$ | CH |
| N | H | H | H | OCH$_3$ | OCH$_3$ | N |
| N | H | H | H | OCH$_3$ | CH$_3$ | N |
| N | H | H | H | OC$_2$H$_5$ | NHCH$_3$ | N |
| N | H | H | CH$_3$ | OCH$_3$ | CH$_3$ | N |
| N | CH$_3$ | H | H | OCH$_3$ | OCH$_3$ | CH |
| N | CH$_3$ | H | H | OCH$_3$ | CH$_3$ | CH |
| N | CH$_3$ | H | H | Cl | OCH$_3$ | CH |
| N | CH$_3$ | H | H | CH$_3$ | CH$_3$ | CH |
| N | CH$_3$ | H | H | OCH$_3$ | OCH$_3$ | N |
| N | CH$_3$ | H | H | OCH$_3$ | CH$_3$ | N |
| N | CH$_3$ | H | H | OC$_2$H$_5$ | NHCH$_3$ | N |
| N | CH$_3$ | H | CH$_3$ | OCH$_3$ | CH$_3$ | N |
| N | OCH$_3$ | H | H | OCH$_3$ | OCH$_3$ | CH |

TABLE 16-continued

| | | | General Formula 16 | | | |
|---|---|---|---|---|---|---|
| Z¹ | R² | R⁴ | R | X | Y | Z⁴ |
| N | OCH₃ | H | H | OCH₃ | CH₃ | CH |
| N | OCH₃ | H | H | Cl | OCH₃ | CH |
| N | OCH₃ | H | H | CH₃ | CH₃ | CH |
| N | OCH₃ | H | H | OCH₃ | OCH₃ | N |
| N | OCH₃ | H | H | OCH₃ | CH₃ | N |
| N | OCH₃ | H | H | OC₂H₅ | NHCH₃ | N |
| N | OCH₃ | H | CH₃ | OCH₃ | CH₃ | N |

TABLE 17

| | | | General Formula 17 | | | | |
|---|---|---|---|---|---|---|---|
| Z | Z² | R² | R³ | R | X | Y | Z⁴ |
| CH | O | CH₃ | CH₃ | H | OCH₃ | OCH₃ | CH |
| CH | O | CH₃ | CH₃ | H | OCH₃ | CH₃ | CH |
| CH | O | CH₃ | CH₃ | H | Cl | OCH₃ | CH |
| CH | O | CH₃ | CH₃ | H | CH₃ | CH₃ | CH |
| CH | O | CH₃ | CH₃ | H | OCH₃ | OCH₃ | N |
| CH | O | CH₃ | CH₃ | H | OCH₃ | CH₃ | N |
| CH | O | CH₃ | CH₃ | H | OC₂H₅ | NHCH₃ | N |
| CH | O | CH₃ | CH₃ | CH₃ | OCH₃ | CH₃ | N |
| N | O | CH₃ | CH₃ | H | OCH₃ | OCH₃ | CH |
| N | O | CH₃ | CH₃ | H | OCH₃ | CH₃ | CH |
| N | O | CH₃ | CH₃ | H | Cl | OCH₃ | CH |
| N | O | CH₃ | CH₃ | H | CH₃ | CH₃ | CH |
| N | O | CH₃ | CH₃ | H | OCH₃ | OCH₃ | N |
| N | O | CH₃ | CH₃ | H | OCH₃ | CH₃ | N |
| N | O | CH₃ | CH₃ | H | OC₂H₅ | NHCH₃ | N |
| N | O | CH₃ | CH₃ | CH₃ | OCH₃ | CH₃ | N |
| CH | S | CH₃ | CH₃ | H | OCH₃ | OCH₃ | CH |
| CH | S | CH₃ | CH₃ | H | OCH₃ | CH₃ | CH |
| CH | S | CH₃ | CH₃ | H | Cl | OCH₃ | CH |
| CH | S | CH₃ | CH₃ | H | CH₃ | CH₃ | CH |
| CH | S | CH₃ | CH₃ | H | OCH₃ | OCH₃ | N |
| CH | S | CH₃ | CH₃ | H | OCH₃ | CH₃ | N |
| CH | S | CH₃ | CH₃ | H | OC₂H₅ | NHCH₃ | N |
| CH | S | CH₃ | CH₃ | CH₃ | OCH₃ | CH₃ | N |
| CH | O | CH₃ | H | H | OCH₃ | OCH₃ | CH |
| CH | O | CH₃ | H | H | OCH₃ | CH₃ | CH |
| CH | O | CH₃ | H | H | Cl | OCH₃ | CH |
| CH | O | CH₃ | H | H | CH₃ | CH₃ | CH |
| CH | O | CH₃ | H | H | OCH₃ | OCH₃ | N |
| CH | O | CH₃ | H | H | OCH₃ | CH₃ | N |
| CH | O | CH₃ | H | H | OC₂H₅ | NHCH₃ | N |
| CH | O | CH₃ | H | CH₃ | OCH₃ | CH₃ | N |
| N | O | CH₃ | H | H | OCH₃ | OCH₃ | CH |
| N | O | CH₃ | H | H | OCH₃ | CH₃ | CH |
| N | O | CH₃ | H | H | Cl | OCH₃ | CH |
| N | O | CH₃ | H | H | CH₃ | CH₃ | CH |
| N | O | CH₃ | H | H | OCH₃ | OCH₃ | N |
| N | O | CH₃ | H | H | OCH₃ | CH₃ | N |
| N | O | CH₃ | H | H | OC₂H₅ | NHCH₃ | N |
| N | O | CH₃ | H | CH₃ | OCH₃ | CH₃ | N |
| CH | S | CH₃ | H | H | OCH₃ | OCH₃ | CH |
| CH | S | CH₃ | H | H | OCH₃ | CH₃ | CH |
| CH | S | CH₃ | H | H | Cl | OCH₃ | CH |
| CH | S | CH₃ | H | H | CH₃ | CH₃ | CH |
| CH | S | CH₃ | H | H | OCH₃ | OCH₃ | N |
| CH | S | CH₃ | H | H | OCH₃ | CH₃ | N |
| CH | S | CH₃ | H | H | OC₂H₅ | NHCH₃ | N |
| CH | S | CH₃ | H | CH₃ | OCH₃ | CH₃ | N |
| CH | O | H | CH₃ | H | OCH₃ | OCH₃ | CH |
| CH | O | H | CH₃ | H | OCH₃ | CH₃ | CH |
| CH | O | H | CH₃ | H | Cl | OCH₃ | CH |
| CH | O | H | CH₃ | H | CH₃ | CH₃ | CH |
| CH | O | H | CH₃ | H | OCH₃ | OCH₃ | N |
| CH | O | H | CH₃ | H | OCH₃ | CH₃ | N |
| CH | O | H | CH₃ | H | OC₂H₅ | NHCH₃ | N |
| CH | O | H | CH₃ | CH₃ | OCH₃ | CH₃ | N |
| N | O | H | CH₃ | H | OCH₃ | OCH₃ | CH |
| N | O | H | CH₃ | H | OCH₃ | CH₃ | CH |
| N | O | H | CH₃ | H | Cl | OCH₃ | CH |
| N | O | H | CH₃ | H | CH₃ | CH₃ | CH |
| N | O | H | CH₃ | H | OCH₃ | OCH₃ | N |
| N | O | H | CH₃ | H | OCH₃ | CH₃ | N |
| N | O | H | CH₃ | H | OC₂H₅ | NHCH₃ | N |
| N | O | H | CH₃ | CH₃ | OCH₃ | CH₃ | N |
| CH | S | H | CH₃ | H | OCH₃ | OCH₃ | CH |
| CH | S | H | CH₃ | H | OCH₃ | CH₃ | CH |
| CH | S | H | CH₃ | H | Cl | OCH₃ | CH |
| CH | S | H | CH₃ | H | CH₃ | CH₃ | CH |
| CH | S | H | CH₃ | H | OCH₃ | OCH₃ | N |
| CH | S | H | CH₃ | H | OCH₃ | CH₃ | N |
| CH | S | H | CH₃ | H | OC₂H₅ | NHCH₃ | N |
| CH | S | H | CH₃ | CH₃ | OCH₃ | CH₃ | N |
| CH | O | H | H | H | OCH₃ | OCH₃ | CH |
| CH | O | H | H | H | OCH₃ | CH₃ | CH |
| CH | O | H | H | H | Cl | OCH₃ | CH |
| CH | O | H | H | H | CH₃ | CH₃ | CH |
| CH | O | H | H | H | OCH₃ | OCH₃ | N |
| CH | O | H | H | H | OCH₃ | CH₃ | N |
| CH | O | H | H | H | OC₂H₅ | NHCH₃ | N |
| CH | O | H | H | CH₃ | OCH₃ | CH₃ | N |
| N | O | H | H | H | OCH₃ | OCH₃ | CH |
| N | O | H | H | H | OCH₃ | CH₃ | CH |
| N | O | H | H | H | Cl | OCH₃ | CH |
| N | O | H | H | H | CH₃ | CH₃ | CH |
| N | O | H | H | H | OCH₃ | OCH₃ | N |
| N | O | H | H | H | OCH₃ | CH₃ | N |
| N | O | H | H | H | OC₂H₅ | NHCH₃ | N |
| N | O | H | H | CH₃ | OCH₃ | CH₃ | N |
| CH | S | H | H | H | OCH₃ | OCH₃ | CH |
| CH | S | H | H | H | OCH₃ | CH₃ | CH |
| CH | S | H | H | H | Cl | OCH₃ | CH |
| CH | S | H | H | H | CH₃ | CH₃ | CH |
| CH | S | H | H | H | OCH₃ | OCH₃ | N |
| CH | S | H | H | H | OCH₃ | CH₃ | N |
| CH | S | H | H | H | OC₂H₅ | NHCH₃ | N |
| CH | S | H | H | CH₃ | OCH₃ | CH₃ | N |
| N | S | CH₃ | CH₃ | H | OCH₃ | OCH₃ | CH |
| N | S | CH₃ | CH₃ | H | OCH₃ | CH₃ | CH |
| N | S | CH₃ | CH₃ | H | Cl | OCH₃ | CH |
| N | S | CH₃ | CH₃ | H | CH₃ | CH₃ | CH |
| N | S | CH₃ | CH₃ | H | OCH₃ | OCH₃ | N |
| N | S | CH₃ | CH₃ | H | OCH₃ | CH₃ | N |
| N | S | CH₃ | CH₃ | H | OC₂H₅ | NHCH₃ | N |
| N | S | CH₃ | CH₃ | CH₃ | OCH₃ | CH₃ | N |
| CH | NCH₃ | CH₃ | CH₃ | H | OCH₃ | OCH₃ | CH |
| CH | NCH₃ | CH₃ | CH₃ | H | OCH₃ | CH₃ | CH |
| CH | NCH₃ | CH₃ | CH₃ | H | Cl | OCH₃ | CH |
| CH | NCH₃ | CH₃ | CH₃ | H | CH₃ | CH₃ | CH |
| CH | NCH₃ | CH₃ | CH₃ | H | OCH₃ | OCH₃ | N |
| CH | NCH₃ | CH₃ | CH₃ | H | OCH₃ | CH₃ | N |
| CH | NCH₃ | CH₃ | CH₃ | H | OC₂H₅ | NHCH₃ | N |
| CH | NCH₃ | CH₃ | CH₃ | CH₃ | OCH₃ | CH₃ | N |
| N | NCH₃ | CH₃ | CH₃ | H | OCH₃ | OCH₃ | CH |
| N | NCH₃ | CH₃ | CH₃ | H | OCH₃ | CH₃ | CH |
| N | NCH₃ | CH₃ | CH₃ | H | Cl | OCH₃ | CH |
| N | NCH₃ | CH₃ | CH₃ | H | CH₃ | CH₃ | CH |
| N | NCH₃ | CH₃ | CH₃ | H | OCH₃ | OCH₃ | N |
| N | NCH₃ | CH₃ | CH₃ | H | OCH₃ | CH₃ | N |
| N | NCH₃ | CH₃ | CH₃ | H | OC₂H₅ | NHCH₃ | N |
| N | NCH₃ | CH₃ | CH₃ | CH₃ | OCH₃ | CH₃ | N |
| N | S | CH₃ | H | H | OCH₃ | OCH₃ | CH |
| N | S | CH₃ | H | H | OCH₃ | CH₃ | CH |
| N | S | CH₃ | H | H | Cl | OCH₃ | CH |
| N | S | CH₃ | H | H | CH₃ | CH₃ | CH |
| N | S | CH₃ | H | H | OCH₃ | OCH₃ | N |
| N | S | CH₃ | H | H | OCH₃ | CH₃ | N |
| N | S | CH₃ | H | H | OC₂H₅ | NHCH₃ | N |
| N | S | CH₃ | H | CH₃ | OCH₃ | CH₃ | N |
| CH | NCH₃ | CH₃ | H | H | OCH₃ | OCH₃ | CH |
| CH | NCH₃ | CH₃ | H | H | OCH₃ | CH₃ | CH |
| CH | NCH₃ | CH₃ | H | H | Cl | OCH₃ | CH |
| CH | NCH₃ | CH₃ | H | H | CH₃ | CH₃ | CH |
| CH | NCH₃ | CH₃ | H | H | OCH₃ | OCH₃ | N |
| CH | NCH₃ | CH₃ | H | H | OCH₃ | CH₃ | N |
| CH | NCH₃ | CH₃ | H | H | OC₂H₅ | NHCH₃ | N |
| CH | NCH₃ | CH₃ | H | CH₃ | OCH₃ | CH₃ | N |
| N | NCH₃ | CH₃ | H | H | OCH₃ | OCH₃ | CH |
| N | NCH₃ | CH₃ | H | H | OCH₃ | CH₃ | CH |
| N | NCH₃ | CH₃ | H | H | Cl | OCH₃ | CH |
| N | NCH₃ | CH₃ | H | H | CH₃ | CH₃ | CH |
| N | NCH₃ | CH₃ | H | H | OCH₃ | OCH₃ | N |
| N | NCH₃ | CH₃ | H | H | OCH₃ | CH₃ | N |
| N | NCH₃ | CH₃ | H | H | OC₂H₅ | NHCH₃ | N |
| N | NCH₃ | CH₃ | H | CH₃ | OCH₃ | CH₃ | N |
| N | S | H | CH₃ | H | OCH₃ | OCH₃ | CH |

TABLE 17-continued

General Formula 17

| Z | Z² | R² | R³ | R | X | Y | Z⁴ |
|---|---|---|---|---|---|---|---|
| N | S | H | CH₃ | H | OCH₃ | CH₃ | CH |
| N | S | H | CH₃ | H | Cl | OCH₃ | CH |
| N | S | H | CH₃ | H | CH₃ | CH₃ | CH |
| N | S | H | CH₃ | H | OCH₃ | OCH₃ | N |
| N | S | H | CH₃ | H | OCH₃ | CH₃ | N |
| N | S | H | CH₃ | H | OC₂H₅ | NHCH₃ | N |
| N | S | H | CH₃ | CH₃ | OCH₃ | CH₃ | N |
| CH | NCH₃ | H | CH₃ | H | OCH₃ | OCH₃ | CH |
| CH | NCH₃ | H | CH₃ | H | OCH₃ | CH₃ | CH |
| CH | NCH₃ | H | CH₃ | H | Cl | OCH₃ | CH |
| CH | NCH₃ | H | CH₃ | H | CH₃ | CH₃ | CH |
| CH | NCH₃ | H | CH₃ | H | OCH₃ | OCH₃ | N |
| CH | NCH₃ | H | CH₃ | H | OCH₃ | CH₃ | N |
| CH | NCH₃ | H | CH₃ | H | OC₂H₅ | NHCH₃ | N |
| CH | NCH₃ | H | CH₃ | CH₃ | OCH₃ | CH₃ | N |
| N | NCH₃ | H | CH₃ | H | OCH₃ | OCH₃ | CH |
| N | NCH₃ | H | CH₃ | H | OCH₃ | CH₃ | CH |
| N | NCH₃ | H | CH₃ | H | Cl | OCH₃ | CH |
| N | NCH₃ | H | CH₃ | H | CH₃ | CH₃ | CH |
| N | NCH₃ | H | CH₃ | H | OCH₃ | OCH₃ | N |
| N | NCH₃ | H | CH₃ | H | OCH₃ | CH₃ | N |
| N | NCH₃ | H | CH₃ | H | OC₂H₅ | NHCH₃ | N |
| N | NCH₃ | H | CH₃ | CH₃ | OCH₃ | CH₃ | N |
| N | S | H | H | H | OCH₃ | OCH₃ | CH |
| N | S | H | H | H | OCH₃ | CH₃ | CH |
| N | S | H | H | H | Cl | OCH₃ | CH |
| N | S | H | H | H | CH₃ | CH₃ | CH |
| N | S | H | H | H | OCH₃ | OCH₃ | N |
| N | S | H | H | H | OCH₃ | CH₃ | N |
| N | S | H | H | H | OC₂H₅ | NHCH₃ | N |
| N | S | H | H | CH₃ | OCH₃ | CH₃ | N |
| CH | NCH₃ | H | H | H | OCH₃ | OCH₃ | CH |
| CH | NCH₃ | H | H | H | OCH₃ | CH₃ | CH |
| CH | NCH₃ | H | H | H | Cl | OCH₃ | CH |
| CH | NCH₃ | H | H | H | CH₃ | CH₃ | CH |
| CH | NCH₃ | H | H | H | OCH₃ | OCH₃ | N |
| CH | NCH₃ | H | H | H | OCH₃ | CH₃ | N |
| CH | NCH₃ | H | H | H | OC₂H₅ | NHCH₃ | N |
| CH | NCH₃ | H | H | CH₃ | OCH₃ | CH₃ | N |
| N | NCH₃ | H | H | H | OCH₃ | OCH₃ | CH |
| N | NCH₃ | H | H | H | OCH₃ | CH₃ | CH |
| N | NCH₃ | H | H | H | Cl | OCH₃ | CH |
| N | NCH₃ | H | H | H | CH₃ | CH₃ | CH |
| N | NCH₃ | H | H | H | OCH₃ | OCH₃ | N |
| N | NCH₃ | H | H | H | OCH₃ | CH₃ | N |
| N | NCH₃ | H | H | H | OC₂H₅ | NHCH₃ | N |
| N | NCH₃ | H | H | CH₃ | OCH₃ | CH₃ | N |

TABLE 18

General Formula 18

| Z | Z³ | R² | R³ | R | X | Y | Z⁴ |
|---|---|---|---|---|---|---|---|
| CH | O | CH₃ | CH₃ | H | OCH₃ | OCH₃ | CH |
| CH | O | CH₃ | CH₃ | H | OCH₃ | CH₃ | CH |
| CH | O | CH₃ | CH₃ | H | Cl | OCH₃ | CH |
| CH | O | CH₃ | CH₃ | H | CH₃ | CH₃ | CH |
| CH | O | CH₃ | CH₃ | H | OCH₃ | OCH₃ | N |
| CH | O | CH₃ | CH₃ | H | OCH₃ | CH₃ | N |
| CH | O | CH₃ | CH₃ | H | OC₂H₅ | NHCH₃ | N |
| CH | O | CH₃ | CH₃ | CH₃ | OCH₃ | CH₃ | N |
| N | O | CH₃ | CH₃ | H | OCH₃ | OCH₃ | CH |
| N | O | CH₃ | CH₃ | H | OCH₃ | CH₃ | CH |
| N | O | CH₃ | CH₃ | H | Cl | OCH₃ | CH |
| N | O | CH₃ | CH₃ | H | CH₃ | CH₃ | CH |
| N | O | CH₃ | CH₃ | H | OCH₃ | OCH₃ | N |
| N | O | CH₃ | CH₃ | H | OCH₃ | CH₃ | N |
| N | O | CH₃ | CH₃ | H | OC₂H₅ | NHCH₃ | N |
| N | O | CH₃ | CH₃ | CH₃ | OCH₃ | CH₃ | N |
| CH | S | CH₃ | CH₃ | H | OCH₃ | OCH₃ | CH |
| CH | S | CH₃ | CH₃ | H | OCH₃ | CH₃ | CH |
| CH | S | CH₃ | CH₃ | H | Cl | OCH₃ | CH |
| CH | S | CH₃ | CH₃ | H | CH₃ | CH₃ | CH |
| CH | S | CH₃ | CH₃ | H | OCH₃ | OCH₃ | N |
| CH | S | CH₃ | CH₃ | H | OCH₃ | CH₃ | N |
| CH | S | CH₃ | CH₃ | H | OC₂H₅ | NHCH₃ | N |
| CH | S | CH₃ | CH₃ | CH₃ | OCH₃ | CH₃ | N |
| CH | O | CH₃ | H | H | OCH₃ | OCH₃ | CH |
| CH | O | CH₃ | H | H | OCH₃ | CH₃ | CH |
| CH | O | CH₃ | H | H | Cl | OCH₃ | CH |
| CH | O | CH₃ | H | H | CH₃ | CH₃ | CH |
| CH | O | CH₃ | H | H | OCH₃ | OCH₃ | N |
| CH | O | CH₃ | H | H | OCH₃ | CH₃ | N |
| CH | O | CH₃ | H | H | OC₂H₅ | NHCH₃ | N |
| CH | O | CH₃ | H | CH₃ | OCH₃ | CH₃ | N |
| N | O | CH₃ | H | H | OCH₃ | OCH₃ | CH |
| N | O | CH₃ | H | H | OCH₃ | CH₃ | CH |
| N | O | CH₃ | H | H | Cl | OCH₃ | CH |
| N | O | CH₃ | H | H | CH₃ | CH₃ | CH |
| N | O | CH₃ | H | H | OCH₃ | OCH₃ | N |
| N | O | CH₃ | H | H | OCH₃ | CH₃ | N |
| N | O | CH₃ | H | H | OC₂H₅ | NHCH₃ | N |
| N | O | CH₃ | H | CH₃ | OCH₃ | CH₃ | N |
| CH | S | CH₃ | H | H | OCH₃ | OCH₃ | CH |
| CH | S | CH₃ | H | H | OCH₃ | CH₃ | CH |
| CH | S | CH₃ | H | H | Cl | OCH₃ | CH |
| CH | S | CH₃ | H | H | CH₃ | CH₃ | CH |
| CH | S | CH₃ | H | H | OCH₃ | OCH₃ | N |
| CH | S | CH₃ | H | H | OCH₃ | CH₃ | N |
| CH | S | CH₃ | H | H | OC₂H₅ | NHCH₃ | N |
| CH | S | CH₃ | H | CH₃ | OCH₃ | CH₃ | N |
| CH | O | H | CH₃ | H | OCH₃ | OCH₃ | CH |
| CH | O | H | CH₃ | H | OCH₃ | CH₃ | CH |
| CH | O | H | CH₃ | H | Cl | OCH₃ | CH |
| CH | O | H | CH₃ | H | CH₃ | CH₃ | CH |
| CH | O | H | CH₃ | H | OCH₃ | OCH₃ | N |
| CH | O | H | CH₃ | H | OCH₃ | CH₃ | N |
| CH | O | H | CH₃ | H | OC₂H₅ | NHCH₃ | N |
| CH | O | H | CH₃ | CH₃ | OCH₃ | CH₃ | N |
| N | O | H | CH₃ | H | OCH₃ | OCH₃ | CH |
| N | O | H | CH₃ | H | OCH₃ | CH₃ | CH |
| N | O | H | CH₃ | H | Cl | OCH₃ | CH |
| N | O | H | CH₃ | H | CH₃ | CH₃ | CH |
| N | O | H | CH₃ | H | OCH₃ | OCH₃ | N |
| N | O | H | CH₃ | H | OCH₃ | CH₃ | N |
| N | O | H | CH₃ | H | OC₂H₅ | NHCH₃ | N |
| N | O | H | CH₃ | CH₃ | OCH₃ | CH₃ | N |
| CH | S | H | CH₃ | H | OCH₃ | OCH₃ | CH |
| CH | S | H | CH₃ | H | OCH₃ | CH₃ | CH |
| CH | S | H | CH₃ | H | Cl | OCH₃ | CH |
| CH | S | H | CH₃ | H | CH₃ | CH₃ | CH |
| CH | S | H | CH₃ | H | OCH₃ | OCH₃ | N |
| CH | S | H | CH₃ | H | OCH₃ | CH₃ | N |
| CH | S | H | CH₃ | H | OC₂H₅ | NHCH₃ | N |
| CH | S | H | CH₃ | CH₃ | OCH₃ | CH₃ | N |
| CH | O | H | H | H | OCH₃ | OCH₃ | CH |
| CH | O | H | H | H | OCH₃ | CH₃ | CH |
| CH | O | H | H | H | Cl | OCH₃ | CH |
| CH | O | H | H | H | CH₃ | CH₃ | CH |
| CH | O | H | H | H | OCH₃ | OCH₃ | N |
| CH | O | H | H | H | OCH₃ | CH₃ | N |
| CH | O | H | H | H | OC₂H₅ | NHCH₃ | N |
| CH | O | H | H | CH₃ | OCH₃ | CH₃ | N |
| N | O | H | H | H | OCH₃ | OCH₃ | CH |
| N | O | H | H | H | OCH₃ | CH₃ | CH |
| N | O | H | H | H | Cl | OCH₃ | CH |
| N | O | H | H | H | CH₃ | CH₃ | CH |
| N | O | H | H | H | OCH₃ | OCH₃ | N |
| N | O | H | H | H | OCH₃ | CH₃ | N |
| N | O | H | H | H | OC₂H₅ | NHCH₃ | N |
| N | O | H | H | CH₃ | OCH₃ | CH₃ | N |
| CH | S | H | H | H | OCH₃ | OCH₃ | CH |
| CH | S | H | H | H | OCH₃ | CH₃ | CH |
| CH | S | H | H | H | Cl | OCH₃ | CH |
| CH | S | H | H | H | CH₃ | CH₃ | CH |
| CH | S | H | H | H | OCH₃ | OCH₃ | N |
| CH | S | H | H | H | OCH₃ | CH₃ | N |
| CH | S | H | H | H | OC₂H₅ | NHCH₃ | N |
| CH | S | H | H | CH₃ | OCH₃ | CH₃ | N |
| N | S | CH₃ | CH₃ | H | OCH₃ | OCH₃ | CH |
| N | S | CH₃ | CH₃ | H | OCH₃ | CH₃ | CH |
| N | S | CH₃ | CH₃ | H | Cl | OCH₃ | CH |
| N | S | CH₃ | CH₃ | H | CH₃ | CH₃ | CH |
| N | S | CH₃ | CH₃ | H | OCH₃ | OCH₃ | N |
| N | S | CH₃ | CH₃ | H | OCH₃ | CH₃ | N |
| N | S | CH₃ | CH₃ | H | OC₂H₅ | NHCH₃ | N |
| N | S | CH₃ | CH₃ | CH₃ | OCH₃ | CH₃ | N |
| CH | NCH₃ | CH₃ | CH₃ | H | OCH₃ | OCH₃ | CH |

TABLE 18-continued

General Formula 18

| Z | Z³ | R² | R³ | R | X | Y | Z⁴ |
|---|---|---|---|---|---|---|---|
| CH | NCH₃ | CH₃ | CH₃ | H | OCH₃ | CH₃ | CH |
| CH | NCH₃ | CH₃ | CH₃ | H | Cl | OCH₃ | CH |
| CH | NCH₃ | CH₃ | CH₃ | H | CH₃ | CH₃ | CH |
| CH | NCH₃ | CH₃ | CH₃ | H | OCH₃ | OCH₃ | N |
| CH | NCH₃ | CH₃ | CH₃ | H | OCH₃ | CH₃ | N |
| CH | NCH₃ | CH₃ | CH₃ | H | OC₂H₅ | NHCH₃ | N |
| CH | NCH₃ | CH₃ | CH₃ | CH₃ | OCH₃ | CH₃ | N |
| N | NCH₃ | CH₃ | CH₃ | H | OCH₃ | OCH₃ | CH |
| N | NCH₃ | CH₃ | CH₃ | H | OCH₃ | CH₃ | CH |
| N | NCH₃ | CH₃ | CH₃ | H | Cl | OCH₃ | CH |
| N | NCH₃ | CH₃ | CH₃ | H | CH₃ | CH₃ | CH |
| N | NCH₃ | CH₃ | CH₃ | H | OCH₃ | OCH₃ | N |
| N | NCH₃ | CH₃ | CH₃ | H | OCH₃ | CH₃ | N |
| N | NCH₃ | CH₃ | CH₃ | H | OC₂H₅ | NHCH₃ | N |
| N | NCH₃ | CH₃ | CH₃ | CH₃ | OCH₃ | CH₃ | N |
| N | S | H | CH₃ | H | OCH₃ | OCH₃ | CH |
| N | S | H | CH₃ | H | OCH₃ | CH₃ | CH |
| N | S | H | CH₃ | H | Cl | OCH₃ | CH |
| N | S | H | CH₃ | H | CH₃ | CH₃ | CH |
| N | S | H | CH₃ | H | OCH₃ | OCH₃ | N |
| N | S | H | CH₃ | H | OCH₃ | CH₃ | N |
| N | S | H | CH₃ | H | OC₂H₅ | NHCH₃ | N |
| N | S | H | CH₃ | CH₃ | OCH₃ | CH₃ | N |
| CH | NCH₃ | H | CH₃ | H | OCH₃ | OCH₃ | CH |
| CH | NCH₃ | H | CH₃ | H | OCH₃ | CH₃ | CH |
| CH | NCH₃ | H | CH₃ | H | Cl | OCH₃ | CH |
| CH | NCH₃ | H | CH₃ | H | CH₃ | CH₃ | CH |
| CH | NCH₃ | H | CH₃ | H | OCH₃ | OCH₃ | N |
| CH | NCH₃ | H | CH₃ | H | OCH₃ | CH₃ | N |
| CH | NCH₃ | H | CH₃ | H | OC₂H₅ | NHCH₃ | N |
| CH | NCH₃ | H | CH₃ | CH₃ | OCH₃ | CH₃ | N |
| N | NCH₃ | H | CH₃ | H | OCH₃ | OCH₃ | CH |
| N | NCH₃ | H | CH₃ | H | OCH₃ | CH₃ | CH |
| N | NCH₃ | H | CH₃ | H | Cl | OCH₃ | CH |
| N | NCH₃ | H | CH₃ | H | CH₃ | CH₃ | CH |
| N | NCH₃ | H | CH₃ | H | OCH₃ | OCH₃ | N |
| N | NCH₃ | H | CH₃ | H | OCH₃ | CH₃ | N |
| N | NCH₃ | H | CH₃ | H | OC₂H₅ | NHCH₃ | N |
| N | NCH₃ | H | CH₃ | CH₃ | OCH₃ | CH₃ | N |
| N | S | H | H | H | OCH₃ | OCH₃ | CH |
| N | S | H | H | H | OCH₃ | CH₃ | CH |
| N | S | H | H | H | Cl | OCH₃ | CH |
| N | S | H | H | H | CH₃ | CH₃ | CH |
| N | S | H | H | H | OCH₃ | OCH₃ | N |
| N | S | H | H | H | OCH₃ | CH₃ | N |
| N | S | H | H | H | OC₂H₅ | NHCH₃ | N |
| N | S | H | H | CH₃ | OCH₃ | CH₃ | N |
| CH | NCH₃ | H | H | H | OCH₃ | OCH₃ | CH |
| CH | NCH₃ | H | H | H | OCH₃ | CH₃ | CH |
| CH | NCH₃ | H | H | H | Cl | OCH₃ | CH |
| CH | NCH₃ | H | H | H | CH₃ | CH₃ | CH |
| CH | NCH₃ | H | H | H | OCH₃ | OCH₃ | N |
| CH | NCH₃ | H | H | H | OCH₃ | CH₃ | N |
| CH | NCH₃ | H | H | H | OC₂H₅ | NHCH₃ | N |
| CH | NCH₃ | H | H | CH₃ | OCH₃ | CH₃ | N |
| N | NCH₃ | H | H | H | OCH₃ | OCH₃ | CH |
| N | NCH₃ | H | H | H | OCH₃ | CH₃ | CH |
| N | NCH₃ | H | H | H | Cl | OCH₃ | CH |
| N | NCH₃ | H | H | H | CH₃ | CH₃ | CH |
| N | NCH₃ | H | H | H | OCH₃ | OCH₃ | N |
| N | NCH₃ | H | H | H | OCH₃ | CH₃ | N |
| N | NCH₃ | H | H | H | OC₂H₅ | NHCH₃ | N |
| N | NCH₃ | H | H | CH₃ | OCH₃ | CH₃ | N |
| N | S | CH₃ | H | H | OCH₃ | OCH₃ | CH |
| N | S | CH₃ | H | H | OCH₃ | CH₃ | CH |
| N | S | CH₃ | H | H | Cl | OCH₃ | CH |
| N | S | CH₃ | H | H | CH₃ | CH₃ | CH |
| N | S | CH₃ | H | H | OCH₃ | OCH₃ | N |
| N | S | CH₃ | H | H | OCH₃ | CH₃ | N |
| N | S | CH₃ | H | H | OC₂H₅ | NHCH₃ | N |
| N | S | CH₃ | H | CH₃ | OCH₃ | CH₃ | N |
| CH | NCH₃ | CH₃ | H | H | OCH₃ | OCH₃ | CH |
| CH | NCH₃ | CH₃ | H | H | OCH₃ | CH₃ | CH |
| CH | NCH₃ | CH₃ | H | H | Cl | OCH₃ | CH |
| CH | NCH₃ | CH₃ | H | H | CH₃ | CH₃ | CH |
| CH | NCH₃ | CH₃ | H | H | OCH₃ | OCH₃ | N |
| CH | NCH₃ | CH₃ | H | H | OCH₃ | CH₃ | N |
| CH | NCH₃ | CH₃ | H | H | OC₂H₅ | NHCH₃ | N |
| CH | NCH₃ | CH₃ | H | CH₃ | OCH₃ | CH₃ | N |
| N | NCH₃ | CH₃ | H | H | OCH₃ | OCH₃ | CH |
| N | NCH₃ | CH₃ | H | H | OCH₃ | CH₃ | CH |
| N | NCH₃ | CH₃ | H | H | Cl | OCH₃ | CH |
| N | NCH₃ | CH₃ | H | H | CH₃ | CH₃ | CH |
| N | NCH₃ | CH₃ | H | H | OCH₃ | OCH₃ | N |
| N | NCH₃ | CH₃ | H | H | OCH₃ | CH₃ | N |
| N | NCH₃ | CH₃ | H | H | OC₂H₅ | NHCH₃ | N |
| N | NCH₃ | CH₃ | H | CH₃ | OCH₃ | CH₃ | N |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s). More specifically, they will contain these ingredients in the following approximate proportions:

| | Weight Percent* | | |
|---|---|---|---|
| | Active Ingredients | Diluent (s) | Surfactant (s) |
| Wettable powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant of a Diluent equals 100 weight percent.

Lower or higher levels of active ingredient can, of course, be present depending on the intended use of the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactered, may be used. The more absorptive diluents are preferred for wettable powders and the denser ones for dusts. Typical liquid diluents and solvents are described in Marsden, "Solvents Guide," 2nd Ed., Interscience, New York, 1985. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luchenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th ed., Blackwell Scientific Publications, Oxford, 1968, pp. 101–103.

In the following examples, all parts are by weight unless otherwise indicated.

EXAMPLE 1

Wettable Powder

| | |
|---|---|
| N-[[(4,6-dimethoxy-2-pyrimidinyl)amino]carbonyl]-2,4-dimethylpyrazolo[1,5-a]-1,3,5-triazine-8-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 2

Wettable Powder

| | |
|---|---|
| N-[[(4-methoxy-6-methyl-2-pyrimidinyl)amino]carbonyl]-isoxazolo[4,5-b]pyridine-3-sulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 3

Granule

| | |
|---|---|
| Wettable Powder of Example 2 | 5% |
| attapulgite granules | 95% |
| (U.S.S. 20–40 mesh; 0.84–0.42 mm) | |

A slurry of wettable powder containing 25% solids is sprayed on the surface of attapulgite granules in a double-cone blender. The granules are dried and packaged.

EXAMPLE 4

Extruded Pellet

| | |
|---|---|
| N-[[(4,6-dimethoxy-2-pyrimidinyl)amino]carbonyl]-2,4-dimethylpyrazolo[1,5-a]-1,3,5-triazine-8-sulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S. Ser. No. 20 sieve (0.84 MM openings). The granules held on a U.S. Ser. No. 40 sieve (0.42 mm openings) may be packaged for use and the fines recycled.

EXAMPLE 5

Oil Suspension

| | |
|---|---|
| N-[[(4-methoxy-6-methyl-2-pyrimidinyl)amino]carbonyl]-isoxazolo[4,5-b]pyridine-3-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 6

Wettable Powder

| | |
|---|---|
| N-[[(4,6-dimethoxy-2-pyrimidinyl)amino]carbonyl]-2,4-dimethylpyrazolo[1,5-a]-1,3,5-triazine-8-sulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S. Ser. No. 50 sieve (0.3 mm opening) and packaged.

EXAMPLE 7

Low Strength Granule

| | |
|---|---|
| N-[[(4-methoxy-6-methyl-2-pyrimidinyl)amino]carbonyl]-isoxazolo[4,5-b]pyridine-3-sulfonamide | 1% |
| N,N-dimethylformamide | 9% |
| attapulgite granules | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 8

Aqueous Suspension

| | |
|---|---|
| N-[[(4,6-dimethoxy-2-pyrimidinyl)amino]carbonyl]-2,4-dimethylpyrazolo[1,5-a]-1,3,5-triazine-8-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 9

Solution

| | |
|---|---|
| N-[[(4-methoxy-6-methyl-2-pyrimidinyl)amino]carbonyl]-isoxazolo[4,5-b]pyridine-3-sulfonamide | 5% |
| water | 95% |

The salt is added directly to the water with stirring to produce the solution, which may then be package for use.

EXAMPLE 10

Low Strength Granule

| | |
|---|---|
| N-[[(4,6-dimethoxy-2-pyrimidinyl)amino]carbonyl]-2,4-dimethylpyrazolo[1,5-a]-1,3,5-triazine-8-sulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 11

Granule

| | |
|---|---|
| N-[[(4-methoxy-6-methyl-2-pyrimidinyl)amino]carbonyl]-isoxazolo[4,5-b]pyridine-3-sulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 12

High Strength Concentrate

| | |
|---|---|
| N-[[(4,6-dimethoxy-2-pyrimidinyl)amino]carbonyl]-2,4-dimethylpyrazolo[1,5-a]-1,3,5-triazine-8-sulfonamide | 99% |
| silica aerogel | 0.5% |
| synthetic amorphous silica | 0.5% |

The ingredients are blended and ground in a hammer-mill to produce a material essentially all passing a U.S. Ser. No. 50 screen (0.3 mm opening). The concentrate may be formulated further if necessary.

EXAMPLE 13

Wettable Powder

| | |
|---|---|
| N-[[(4-methoxy-6-methyl-2-pyrimidinyl)amino]carbonyl]-isoxazolo[4,5-b]pyridine-3-sulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 14

Wettable Powder

| | |
|---|---|
| N-[[(4,6-dimethoxy-2-pyrimidinyl)amino]carbonyl]-2,4-dimethylpyrazolo[1,5-a]-1,3,5-triazine-8-sulfonamide | 40% |
| sodium ligninsulfonate | 20% |
| montmorillonite clay | 40% |

The ingredients are thoroughly blended, coarsely hammer-milled and then air-milled to produce particles essentially all blow 10 microns in size. The material is reblended and then packaged.

EXAMPLE 15

Oil Suspension

| | |
|---|---|
| N-[[(4-methoxy-6-methyl-2-pyrimidinyl)amino]carbonyl]-isoxazolo[4,5-b]pyridine-3-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 16

Dust

| | |
|---|---|
| N-[[(4,6-dimethoxy-2-pyrimidinyl)amino]carbonyl]-2,4-dimethylpyrazolo[1,5-a]-1,3,5-triazine-8-sulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 17

Emulsifiable Concentrate

| | |
|---|---|
| N-[[(4-methoxy-6-methyl-2-pyrimidinyl)amino]carbonyl]-isoxazolo[4,5-b]pyridine-3-sulfonamide | 10% |
| chlorobenzene | 84% |
| sorbitan monostearate and polyoxyethylene condensates thereof | 6% |

The ingredients are combined and stirred to produce a solution which can be emulsified in water for application.

Utility

The compounds of the present invention are expected to be active preemergent or postemergent herbicides or plant growth regulators. The rates of application for the compounds of the invention are determined by a number of factors, including their use as plant growth modifiers or as herbicides, the crop species involved, the types of weeds to be controlled, weather and climate, formulations selected, mode of application, amount of foliage-present, etc. In general terms, the subject compounds should be applied at levels of around 0.001 to 20 kg/ha, the lower rates being suggested for use on lighter soils and/or those having a low organic matter content, for plant growth modification or for situations where only short-term persistence is required, such as a herbicide for fallow land.

The compounds of the invention may be used in combination with any other commercial herbicide, nonlimiting examples of which are listed below:

| Common Name | Chemical Name |
|---|---|
| acetochlor | 2-chloro-N-(ethoxymethyl)-N-(2-ethyl-6-methylphenyl)acetamide |
| acifluorfen | 5-[2-chloro-4-(trifluoromethyl)phenoxy]-2-nitrobenzoic acid |
| acrolein | 2-propenal |
| alachlor | 2-chloro-N-(2,6-diethylphenyl-N-methoxymethyl)acetamide |
| ametryn | N-ethyl-N'-(1-methylethyl-6-(methylthio-1,3,5-triazine-2,4-diamine |
| amitrole | 1H-1,2,4-triazol-3-amine |
| AMS | ammonium sulfamate |
| asulam | methyl[(4-aminophenyl)sulfonyl]carbamate |
| atrazine | 6-chloro-N-ethyl-N'-(1-methylethyl)-1,3,5-triazine-2,4-diamine |
| barban | 4-chloro-2-butynyl 3-chlorocarbamate |
| benefin | N-butyl-N-ethyl-2,6-dinitro-4-(trifluoromethyl)benzenamine |
| bensulfuron | 2-[[[[(4,6-dimethoxy-2-pyrimidinyl)amino]carbonyl]amino]sulfonyl]methyl]benzoic acid |

-continued

| Common Name | Chemical Name |
|---|---|
| bensulide | O,O-bis(1-methylethyl)S-[2-[(phenylsulfonyl)amino]ethyl]phosphorodithioate |
| bentazon | 3-(1-methylethyl)-(1H)-2,2,3-benzothiadiazin-4(3H)-one 2,2-dioxide |
| benzofluor | N-[4-(ethylthio)-2-(trifluoromethyl)-phenyl]methanesulfonamide |
| benzoylprop | N-benzoyl-N-(3,4-dichlorophenyl)-DL-alanine |
| bifenox | methyl 5-(2,4-dichlorophenoxy)-2-nitrobenzoate |
| bromacil | 5-bromo-6-methyl-3-(1-methylpropyl)-2,4(1H,3H)pyrimidinedione |
| bromoxynil | 3,5-dibromo-4-hydroxybenzonitrile |
| butachlor | N-(butoxymethyl)-2-chloro-N-(2,6-diethylphenyl)acetamide |
| buthidazole | 3-[5-(1,1-dimethylethyl)-1,3,4-thiadiazol-2-yl]-4-hyrdroxy-1-methyl-2-imidazolidinone |
| butralin | 4-(1,1-dimethylethyl)-N-(1-methylpropyl)-2,6-dinitrobenzenamine |
| butylate | S-ethyl bis(2-methylpropyl)carbamothioate |
| cacodylic acid | dimethyl arsinic oxide |
| CDAA | 2-chloro-N,N-di-2-propenylacetamide |
| CDEC | 2-chloroallyl diethyldithiocarbamate |
| chloramben | 3-amino-2,5-dichlorobenzoic acid |
| chlorbromuron | 3-(4-bromo-3-chlorophenyl)-1-methoxy-1-methylurea |
| chlorimuron ethyl | 2-[[[[4-chloro-6-methoxy-2-pyrimidinyl)-amino]carbonyl]amino]sulfonyl]benzoic acid, ethyl ester |
| chloroxuron | N'-[4-(4-chlorophenoxy)phenyl]-N,N-dimethylurea |
| chlorpropham | 1-methyethyl 3-chlorophenylcarbamate |
| chlorsulfuron | 2-chloro-N-[[(4-methoxy-6-methyl-1,3,5-triazin-2-yl)amino]carbonyl]benxenesulfonamide |
| chlortoluron | N'-(3-chloro-4-methylphenyl-N',N'-dimethylurea |
| cinmethylin | exo-1-methyl-4-(1-methylethyl)-2-[(2-methylphenyl)methoxy]-7-oxabicyclo-[2.2.1]heptane |
| clethodim | (E,E)-(±)-2-[1-[[(3-chloro-2-propenyl)-oxy]imino]propyl]-5-[2-(ethylthio)-propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy)-imino]butyl]-5-[2-(ethylthio)propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-3-yl]amino]-2-methylpropanenitrile |
| cycloate | S-ethyl cyclohexanecarbamothioate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl] cyclopropanecarboxamide |
| cypromid | 3',4'-dichlorocyclopropanecarboxanilide |
| dalapon | 2,2-dichloropropionic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmediphan | ethyl [3-[[(phenylamino)carbonyl]oxy]-phenyl]carbamate |
| desmetryn | 2-(isopropylamino)-4-(methylamino)-6-methylthio)-s-triazine |
| diallate | S-(2,3-dichlor-2-propenyl)bis(1-methylethyl)carbamothioate |
| dicamba | 3,6-dichloro-2-methoxybenzoic acid |
| dichlobenil | 2,6-dichlorobenzonitrile |
| dichlorprop | (±)-2-(2,4-dichlorphenoxy)propanoic acid |
| dichlofop | (±)-2-[4-(2,4-dichlorophenoxy)phenoxy]-propanoic acid |
| diethatyl | N-(chloroacetyl)-N-(2,6-diethylphenyl)- |

-continued

| Common Name | Chemical Name |
|---|---|
| difenzoquat | glycine 1,2-dimethyl-3,5-diphenyl-1H-pyrazolium |
| dinitramine | N³,N³-diethyl-2,4-dinitro-6-(trifluoromethyl)-1,3-benzenediamine |
| dinoseb | 2-(1-methylpropyl)-4,6-dinitrophenol |
| diphenamid | N,N-dimethyl-α-phenylbenzeneacetamide |
| dipropetryn | 6-(ethylthio)-N,N'-bis(1-methylethyl)-1,3,5-triazine-2,4-diamine |
| diquat | 6,7-dihydrodipyrido[1,2-α-2',1'-c]-pyrazinediium ion |
| diuron | N'-(3,4-dichlorophenyl)-N,N-dimethylurea |
| DNOC | 2-methyl-4,6-dinitrophenol |
| DPX-M6316 | 3-[[[[(4-methoxy-6-methyl-1,3,5-triazin-2-yl)amino]carbonyl]amino]sulfonyl]-2-thiophenecarboxylic acid, methyl ester |
| DSMA | disodium salt of MAA |
| endothall | 7-oxabicyclo[2.2.1]heptane-2,3-dicarboxylic acid |
| EPTC | S-ethyl dipropylcarbamothioate |
| ethalfluralin | N-ethyl-N-(2-methyl-2-propenyl)-2,6-dinitro-4-(trifluoromethyl)-benzenamine |
| ethofumesate | (±)-2-ethoxy-2,3-dihydro-3,3-dimethyl-5-benzofuranyl methanesulfonate |
| Express ® | 2-[[N-(4-methoxy-6-methyl-1,3,5-triazine-2-yl)-N-methylaminocarbonyl]aminosulfonyl]benzoic acid, methyl ester |
| fenac | 2,3,6-trichlorobenzeneacetic acid |
| fenoxaprop | (±)-2-[4-[(6-chloro-2-benzoxazolyl)oxy]-phenoxy]propanoic acid |
| fenuron | N,N-dimethyl-N'-phenylurea |
| fenuron TCA | Salt of fenuron and TCA |
| flamprop | N-benzoyl-N-(3-chloro-4-fluorophenyl)-DL-alanine |
| fluazifop | (±)2-[4-[[5-(trifluoromethyl)-2-pyridinyl]oxy]phenoxy]propanoic acid |
| fluazifop-P | (R)-2-[4-[[5-trifluoromethyl)-2-pyridinyl]oxy]phenoxy]propanoic acid |
| fluchloralin | N-(2-chloroethyl)-2,6-dinitro-N-propyl-4-(trifluoromethyl)benzenamine |
| fluometuron | N,N-dimethyl-N'-(3-(trifluoromethyl)-phenyl]urea |
| fluorochloridone | 3-chloro-4-(chloromethyl)-1-[3-trifluoromethyl)phenyl]-2-pyrrolidinone |
| fluorodifen | p-nitrophenyl α,α,α-trifluoro-2-nitro-p-tolyl ether |
| fluoroglycofen | carboxymethyl 5-[2-chloro-4-(trifluoromethyl)phenoxy]-2-nitrobenzoate |
| fluridone | 1-methyl-3-phenyl-5-[3-(trifluoromethyl)phenyl]-4(1H)-pyridinone |
| fomesafen | 5-(2-chloro-4-trifluoromethylphenoxy)-N-methylsulfonyl-2-nitrobenzamide |
| fosamine | ethyl hydrogen (aminocarbonyl)-phosphate |
| glyphosate | N-(phosphonomethyl)glycine |
| haloxyfop | 2-[4-[[3-chloro-5-(trifluoromethyl)-2-pyridinyl]oxy]phenoxy]propanoic acid |
| hexaflurate | potassium hexafluoroarsenate |
| hexazinone | 3-cyclohexyl-6-(dimethylamino)-1-methyl-1,3,5-triazine-2,4(1H,3H)-dione |
| imazamethabenz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl-p-toluic acid, methyl ester |
| imazapyr | (±)2-[4,5-dihydro-4-methyl-4-(1-methylethyl)-5-oxo-1H-imidazol-2-yl]-3-pyridinecarboxylic acid |
| imazaquin | 2-(4,5-dihydro-4-methyl-4-(1-methylethyl)-5-oxo-1H-imidazol-2-yl)-3-quinolinecarboxylic acid |
| imazethapyr | (±)-2-[4,5-dihydro-4-methyl-4-(1-methylethyl)-5-oxo-1H-imidazol-2-yl]-5-ethyl-3-pyridinecarboxylic acid |
| ioxynil | 4-hydroxy-3,5-diiodobenzonitrile |
| isopropalin | 4-(1-methylethyl)-2,6-dinitro-N,N-dipropylbenzenamine |
| isoproturon | N-(4-isopropylphenyl)-N',N'-dimethylurea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]phenyl-(1,1-dimethylethyl)carbamate |
| lactofen | (±)-2-ethoxy-1-methyl-2-oxoethyl-5-[2-chloro-4-(trifluoromethyl)phenoxy]-2-nitrobenzoate |
| lenacil | 3-cyclohexyl-6,7-dihydro-1H-cyclopenta-pyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPB | 4-(4-chloro-2-methylphenoxy)butanoic acid |
| mecoprop | (±)-2-(4-chloro-2-methylphenoxy)-propanoic acid |
| mefluidide | N-[(2,4-dimethyl-5-[[(trifluormethyl)-sulfonyl]amino]phenyl]acetamide |
| methalpropalin | N-(2-methyl-2-propenyl)-2,6-dinitro-N-propyl-4-(trifluoromethyl)benzenamide |
| methabenzthiazuron | 1,3-dimethyl-3-(2-benzothiazolyl)urea |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)N,N-dimethylurea |
| metolachlor | 2-chloro-N-(2-ethyl-6-methylphenyl)-N-(2-methoxy-1-methylethyl)acetamide |
| metribuzin | 4-amino-6-(1,1-dimethylethyl)-3-(methylthio)-1,2,4-triazin-5(4H)-one |
| metsulfuron methyl | 2- [[[[(4-methoxy-6-methyl-1,3,5-triazine-methyl-2-yl)amino]carbonyl]amion]sulfonyl]benzoic acid, methyl ester |
| MH | 1,2-dihydro-3,6-pyridazinedione |
| molinate | S-ethyl hexahydro-1H-azepine-1-carbothioate |
| monolinuron | 3-(p-chlorophenyl)-1-methoxy-1-methyl-urea |
| monuron | N'(4-chlorophenyl)-N,N-dimethylurea |
| monuron TCA | Salt of monuron and TCA |
| MSMA | monosodium salt of MAA |
| napropamide | N,N-diethyl-2-(1-naphthalenyloxy)-propanamide |
| naptalam | 2-[(1-naphthalenylamino)carbonyl]-benzoic acid |
| neburon | 1-butyl-3-(3,4-dichlorophenyl)-1-methyl-urea |
| nitralin | 4-(methylsulfonyl)-2,6-dinitro-N,N-dipropylaniline |
| nitrofen | 2,4-dichloro-1-(4-nitrophenoxy)benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea 3aα,4α,5α,7α,7aα-isomer |
| norflurazon | 4-chloro-5-(methylamino)-2-(3-trifluoromethyl)phenyl-3(2H)-pyridazinone |
| oryzalin | 4-(dipropylamino)-3,5-dinitro-benzenesulfonamide |
| oxadiazon | 3-[2,4-dichloro-5-(1-methylethoxy)-phenyl]-5-(1,1-dimethylethyl)-1,3,4-oxadiazol-2-(3H)-one |
| oxyflurofen | 2-chloro-1-(3-ethoxy-4-nitrophenoxy)-4-(trifluoromethyl)benzene |
| paraquat | 1,1'-dimethyl-4,4'-bipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |
| phenmedipham | 3-[(methoxycarbonyl)amino]phenyl(3-methylphenyl)carbamate |
| picloram | 4-amino-3,5,6-trichloro-2-pyridine-carboxylic acid |
| PPG-1013 | 5-(2-chloro-4-(trifluoromethyl)-phenoxy)-2-nitroacetophenone oxime-O-acetic acid, methyl ester |
| procyazine | 2-[[4-chloro-6-(cyclopropylamino)-1,3,5- |

-continued

| Common Name | Chemical Name |
|---|---|
| | triazine-2-yl]amino]-2-methylpropane-nitrile |
| profluralin | N-(cyclopropylmethyl)-2,6-dinitro-N-propyl-4-(trifluoromethyl)benzenamine |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propynyl)benzamide |
| propachlor | 2-chloro-N-(1-methylethyl)-N-phenylacetamide |
| propanil | N-(3',4'-dichlorophenyl)propanamide |
| propazine | 6-chloro-N,N'-bis(1-methylethyl)-1,3,5-triazine-2,4-diamine |
| propham | 1-methylethyl phenylcarbamate |
| prosulfalin | N-[[4-(dipropylamino)-3,5-dinitrophenyl]sulfonyl]-S,S-dimethylsulfilimine |
| prynachlor | 2-chloro-N-(1-methyl-2-propynyl)acetanilide |
| pyrazon | 5-amino-4-chloro-2-phenyl-3(2H)-pyridazinone |
| quizalofop ethyl | 2-[4-(6-chlorquinoxalin-2-yloxy)phenoxypropanoic acid, ethyl ester |
| quizalofop | (±)-2-[4-[(6-chloro-2-quinoxalinyl)oxy]phenoxy]propanoic acid |
| secbumeton | N-ethyl-6-methoxy-N'(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexene-1-one |
| siduron | N-(2-methylcyclohexyl)-N''-phenylurea |
| simazine | 6-chloro-N,N'-diethyl-1,3,5-triazine-2,4-diamine |
| sulfometuron methyl | 2-[[[[(4,6-dimethyl-2-pyrimidinyl)amino]carbonyl]amino]sulfonyl]-benzoic acid, methyl ester |
| TCA | trichloroacetic acid |
| tebuthiuron | N-[5-(1,1-dimethylethyl)-1,3,4-thiadiazol-2-yl]-N,N'-dimethylurea |
| terbacil | 5-chloro-3-(1,1-dimethylethyl)-6-methyl-2,4(1H,3H)-pyrimidinedione |
| terbuchlor | N-(butoxymethyl)-2-chloro-N-[2-(1,1-dimethylethyl)-6-methylphenyl]-acetamide |
| terbuthylazine | 2-(tert-butylamino)-4-chloro-6-(ethylamino)-s-triazine |
| terbutol | 2,6-di-tert-butyl-p-tolyl methylcarbamate |
| terbutryn | N-(1,1-dimethylethyl)-N'-ethyl-6-(methylthio)-1,3,5-triazine-2,4-diamine |
| thiameturon methyl | 3- [[[[(4-methoxy-6-methyl-1,3,5-triazin-2-yl)amino]carbonyl]-amino]sulfonyl]-2-thiophenecarboxylic acid, methyl ester |
| thiobencarb | S-[(4-chlorophenyl)methyl]diethylcarbamothioate |
| triallate | S-(2,3,3-trichloro-2-propenyl)bis(1-methylethyl)carbamothioate |
| triclopyr | [(3,5,6-trichloro-2-pyridinyl)-oxy]acetic acid |
| tridiphane | 1-(3,5-dichlorophenyl)-2-(2,2,2-trichloroethyl)oxirane |
| trifluralin | 2,6-dinitro-N,N-dipropyl-4-(trifluoromethyl)benzenamine |
| trimeturon | 1-(p-chlorophenyl)-2,3,3-trimethylpseudourea |
| 2,4-D | (2,4-dichlorophenoxy)acetic acid |
| 2,4-DB | 4-(2,4-dichlorphenoxy)butanoic acid |
| vernolate | S-propyl dipropylthiocarbamothioate |
| xylachlor | 2-chloro-N-(2,3-dimethylphenyl)-N-(1-methylethyl)acetamide |

What is claimed is:
1. A compound of the formula

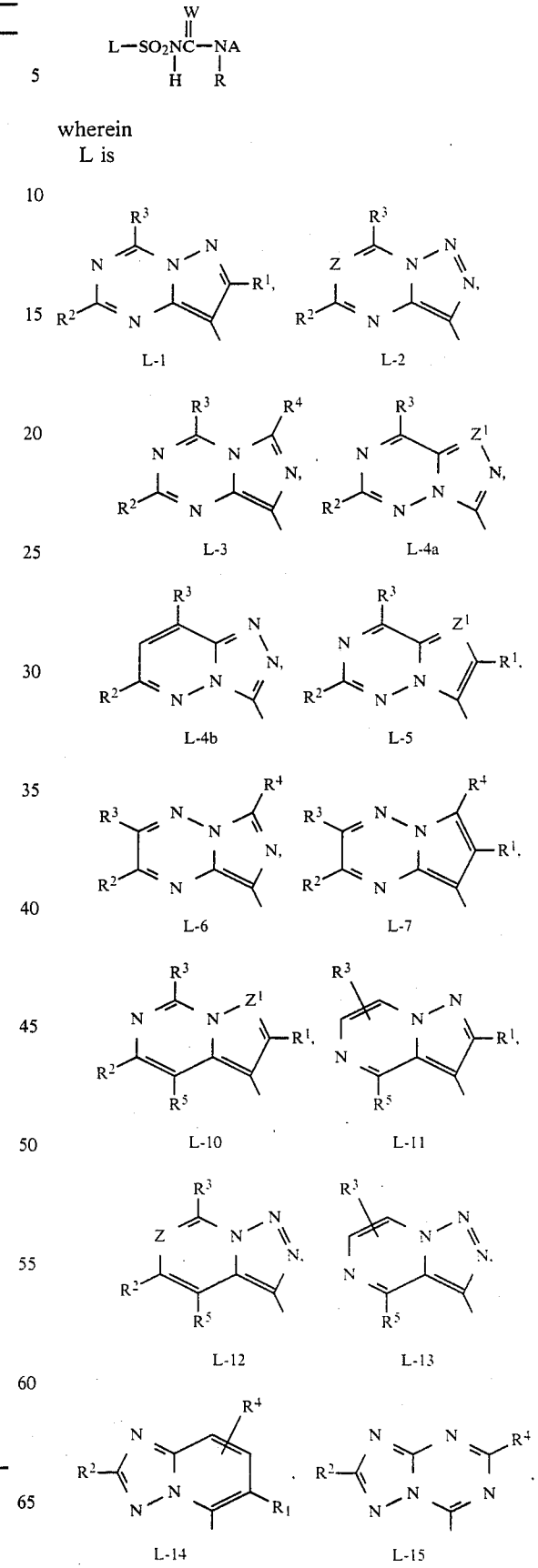

wherein
L is

L-1, L-2, L-3, L-4a, L-4b, L-5, L-6, L-7, L-10, L-11, L-12, L-13, L-14, L-15

-continued

L-16, L-17, L-18, L-19, L-20 (structures shown)

$R^1$ is H, halogen, $C_1$-$C_3$ alkyl, $C_1$-$C_3$ haloalkyl, $OR^6$, $SR^6$, $S(O)R^6$, $S(O)_2R^6$, $CO_2R^7$, $C(O)NR^8R^9$, $S(O)_2NR^{10}R^{11}$, $C_2$-$C_3$ alkenyl, $C_2$-$C_3$ haloalkenyl, $C_2$-$C_3$ alkynyl, $NO_2$, CN, $C(O)R^{12}$, $C(R^{13})$=$NOR^{14}$ or $C_1$-$C_2$ alkyl substituted by $C_1$-$C_2$ alkoxy, $C_1$-$C_2$ alkylthio or CN;

$R^2$ is H, $C_1$-$C_3$ alkyl, $C_1$-$C_3$ alkoxy, $C_1$-$C_2$ haloalkoxy or $C_1$-$C_2$ alkyl substituted with $OCH_3$, $SCH_3$ or CN;

$R^3$ is H, $CH_3$ or $OCH_3$;
$R^4$ is H or $CH_3$;
$R^5$ is H, halogen, $C_1$-$C_3$ alkyl, $C_1$-$C_3$ haloalkyl, $OR^6$, $SR^6$, $S(O)R^6$, $S(O)_2R^6$, $CO_2R^7$, $C(O)NR^8R^9$, $S(O)_2NR^{10}R^{11}$, $C_2$-$C_3$ alkenyl, $C_2$-$C_3$ haloalkenyl, $C_2$-$C_3$ alkynyl, $NO_2$, CN, $C(O)R^{12}$, or $C_1$-$C_2$ alkyl substituted by $C_1$-$C_2$ alkoxy, $C_1$-$C_2$ alkylthio or CN;

$R^6$ is $C_1$-$C_3$ alkyl, $C_1$-$C_3$ haloalkyl, $C_3$ alkenyl, $C_2$-$C_3$ haloalkenyl, propargyl, cyclopropyl, cyclopropylmethyl or —$CH_2CH_2$— substituted by OH, $C_1$-$C_2$ alkoxy, SH, $C_1$-$C_2$ thioalkyl or CN;

$R^7$ is $C_1$-$C_4$ alkyl, $C_2$-$C_3$ haloalkyl, allyl, propargyl, cyclopropyl, cyclopropylmethyl, or —$CH_2CH_2$— substituted by OH, $OCH_3$, $SCH_3$ or CN;

$R^8$ is H or $C_1$-$C_2$ alkyl;
$R^9$ is $C_1$-$C_3$ alkyl, $C_1$-$C_3$ alkoxy, allyl, propargyl, cyclopropyl, $CH_2CN$, $CH_2CH_2CN$ or $CH_2CH_2OCH_3$;

$R^{10}$ is H or $C_1$-$C_3$ alkyl;
$R^{11}$ is $C_1$-$C_3$ alkyl, $C_1$-$C_3$ alkoxy, allyl, propargyl, cyclopropyl, cyclopropylmethyl, $CH_2CN$, $CH_2CH_2CN$ or $CH_2CH_2OCH_3$;

$R^{10}$ and $R^{11}$ can be taken together to form a ring consisting of (—$CH_2$—)$_4$, (—$CH_2$—)$_5$ or (—$CH_2CH_2$—)$_2$O;

$R^{12}$ is H, $C_1$-$C_3$ alkyl or cyclopropyl;
$R^{13}$ is H, $C_1$-$C_3$ alkyl, cyclopropyl, Cl, CN, $OCH_3$, $SCH_3$ or $N(CH_3)_2$;
$R^{14}$ is H or $C_1$-$C_3$ alkyl;
Z is N or CH;
$Z^1$ is N, CH or $CCH_3$;
$Z^2$ is O, S or $NCH_3$;
$Z^3$ is O, S or N—$R^{15}$;

$R^{15}$ is H, $C_1$-$C_2$ alkyl, $C_1$-$C_2$ haloalkyl, $CH_2CH_2OCH_3$, $CH_2CH_2SCH_3$, $CH_2CN$ or $CO_2CH_3$;

W is O or S;
R is H or $CH_3$;
A is

A-1 (structure shown)

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl)amino;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkyl thioalkyl, $C_2$-$C_5$ alkylsulfinylalkyl, $C_2$-$C_5$ alkylsulfonylalkyl, $C_1$-$C_4$ haloalkyl, $C_2$-$C_4$ alkynyl, $C_3$-$C_5$ cycloalkyl, azido, cyano, (structures shown)

or $N(OCH_3)CH_3$;
m is 2 or 3;
$Q_1$ and $Q_2$ are independently O or S;
$R_a$ is H or $C_1$-$C_3$ alkyl;
$R_b$ and $R_c$ are independently $C_1$-$C_3$ alkyl; and
$Z^4$ is CH, $CCH_3$, $CC_2H_5$, CCl or CBr;

and their agriculturally suitable salts; provided that (1) when X is halogen, then $Z^4$ is CH and Y is $OCH_3$, $OC_2H_5$, $NH_2$, $NHCH_3$, $N(CH_3)_2$, $OCF_2H$, $OCF_2Br$ or $N(OCH_3)CH_3$;

(2) when X or Y is $C_1$ haloalkoxy, then $Z^4$ is CH;

(3) when W is S, then R is H, $Z^4$ is CH, and Y is $CH_3$, $OCH_3$, $OC_2H_5$, $CH_2OCH_3$, $C_2H_5$, $CF_3$, $SCH_3$, $OCH_2CH$=$CH_2$, $OCH_2C$≡$CH$, $OCH_2CH_2OCH_3$, $CH(OCH_3)_2$ or (structure shown)

(4) when the total number of carbon atoms of X and Y is greater than four, then the greatest combined number of carbons of any two substituents on an L, selected from $R^1$, $R^2$, $R^3$, $R^4$, $R^5$ and $R^{15}$ is less than or equal to six;

(5) the total of carbon atoms of $R^{10}$ and $R^{11}$ is less than or equal to five.

2. Compounds of claim 1 wherein L is L-1, L-3, L-4a, L-4b, L-5, L-6, L-7, L-10, L-11, L-14, L-16, L-19 or L-20.

3. Compounds of claim 2 wherein W is O and $Z^4$ is CH.

4. Compounds of claim 3 wherein
X is $C_1$–$C_2$ alkyl, $C_1$–$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$;
Y is H, $C_1$–$C_2$ alkyl, $C_1$–$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$,

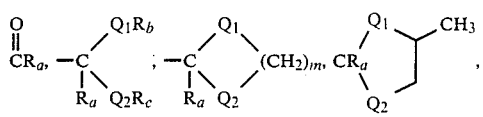

$OCF_2H$, $OCH_2Br$, $SCF_2H$, cyclopropyl, $C\equiv CH$ or $C\equiv CCH_3$; and $R_b$ and $R_c$ are independently $CH_3$ or $CH_2CH_3$.

5. Compounds of claim 4 where
$R^1$ is H, halogen, $C_1$–$C_2$ alkyl, $C_1$–$C_2$ haloalkyl, $OR^6$, $SR^6$, $S(O)R^6$, $S(O)_2R^6$, $CO_2R^7$, $C(O)NR^8R^9$, $S(O)_2NR^{10}R^{11}$, $C_2$–$C_3$ alkenyl, $C_2$–$C_3$ haloalkenyl, $NO_2$, CN, $C(O)R^{12}$, $C(R^{13})=NOR^{14}$ or $C_1$–$C_2$ alkyl substituted by $C_1$–$C_2$ alkoxy, $C_1$–$C_2$ alkylthio or CN;
$R^2$ is H, $CH_3$ or $OCH_3$;
$R^5$ is H, halogen, $C_1$–$C_2$ alkyl, $C_1$–$C_2$ haloalkyl, $OR^6$, $SR^6$, $S(O)R^6$, $S(O)_2R^6$, $CO_2R^7$, $C(O)NR^8R^9$, $S(O)_2NR^{10}R^{11}$, $C_2$–$C_3$ alkenyl, $C_2$–$C_3$ haloalkenyl, $NO_2$, CN, $C(O)R^{12}$, or $C_1$–$C_2$ alkyl substituted by $C_1$–$C_2$ alkoxy, $C_1$–$C_2$ alkylthio or CN;
$R^6$ is $C_1$–$C_3$ alkyl, $C_1$–$C_3$ haloalkyl, $C_3$ alkenyl, $C_2$–$C_3$ haloalkenyl, propargyl, cyclopropyl or cyclopropylmethyl.

6. Compounds of claim 5 where
X is $CH_3$, $OCH_3OCH_2CH_3$, Cl or $OCF_2H$;
Y is $CH_3$, $OCH_3$, $C_2H_5$, $CH_2OCH_3$, $NHCH_3$, $CH(OCH_3)_3$ or cyclopropyl; and
R is H.

7. Compounds of claim 6 where L is L-1.
8. Compounds of claim 6 where L is L-3.
9. Compounds of claim 6 where L is L-4a.
10. Compounds of claim 6 where L is L-4b.
11. Compounds of claim 6 where L is L-5.
12. Compounds of claim 6 where L is L-6.
13. Compounds of claim 6 where L is L-7.
14. Compounds of claim 6 where L is L-10.
15. Compounds of claim 6 where L is L-11.
16. Compounds of claim 6 where L is L-14.
17. Compounds of claim 6 where L is L-19.
18. Compounds of claim 6 where L is L-20.

19. An agriculturally suitable composition for controlling the growth of undesired vegetation comprising an effective amount of a compound of claim 1 and at least one of the following: surfactant, solid diluent or liquid diluent.

20. An agriculturally suitable composition for controlling the growth of undesired vegetation comprising an effective amount of a compound of claim 2 and at least one of the following: surfactant, solid diluent or liquid diluent.

21. An agriculturally suitable composition for controlling the growth of undesired vegetation comprising an effective amount of a compound of claim 3 and at least one of the following: surfactant, solid diluent or liquid diluent.

22. An agriculturally suitable composition for controlling the growth of undesired vegetation comprising an effective amount of a compound of claim 4 and at least one of the following: surfactant, solid diluent or liquid diluent.

23. An agriculturally suitable composition for controlling the growth of undesired vegetation comprising an effective amount of a compound of claim 5 and at least one of the following: surfactant, solid diluent or liquid diluent.

24. An agriculturally suitable composition for controlling the growth of undesired vegetation comprising an effective amount of a compound of claim 6 and at least one of the following: surfactant, solid diluent or liquid diluent.

25. An agriculturally suitable composition for controlling the growth of undesired vegetation comprising an effective amount of a compound of claim 7 and at least one of the following: surfactant, solid diluent or liquid diluent.

26. An agriculturally suitable composition for controlling the growth of undesired vegetation comprising an effective amount of a compound of claim 8 and at least one of the following: surfactant, solid diluent or liquid diluent.

27. An agriculturally suitable composition for controlling the growth of undesired vegetation comprising an effective amount of a compound of claim 9 and at least one of the following: surfactant, solid diluent or liquid diluent.

28. An agriculturally suitable composition for controlling the growth of undesired vegetation comprising an effective amount of a compound of claim 10 and at least one of the following: surfactant, solid diluent or liquid diluent.

29. A method for controlling the growth of undesired vegetation which comprises applying to the locus to be protected an effective amount of a compound of claim 1.

30. A method for controlling the growth of undesired vegetation which comprises applying to the locus to be protected an effective amount of a compound of claim 2.

31. A method for controlling the growth of undesired vegetation which comprises applying to the locus to be protected an effective amount of a compound of claim 3.

32. A method for controlling the growth of undesired vegetation which comprises applying to the locus to be protected an effective amount of a compound of claim 4.

33. A method for controlling the growth of undesired vegetation which comprises applying to the locus to be protected an effective amount of a compound of claim 5.

34. A method for controlling the growth of undesired vegetation which comprises applying to the locus to be protected an effective amount of a compound of claim 6.

35. A method for controlling the growth of undesired vegetation which comprises applying to the locus to be protected an effective amount of a compound of claim 7.

36. A method for controlling the growth of undesired vegetation which comprises applying to the locus to be protected an effective amount of a compound of claim 8.

37. A method for controlling the growth of undesired vegetation which comprises applying to the locus to be protected an effective amount of a compound of claim 9.

38. A method for controlling the growth of undesired vegetation which comprises applying to the locus to be protected an effective amount of a compound of claim 10.

* * * * *

UNITED STATES PATENT AND TRADEMARK OFFICE
CERTIFICATE OF CORRECTION

PATENT NO. : 4,921,527
DATED : May 1, 1990
INVENTOR(S) : Chi-Ping Tseng

It is certified that error appears in the above-identified patent and that said Letters Patent is hereby corrected as shown below:

Claim 6, in the definition of X, there should be a comma between $OCH_3$ and $OCH_2CH_3$ Claim 6, in the definition of Y delete " $CH(OCH_3)_3$ " and substitute therefore -- $CH(OCH_3)_2$ --.

Signed and Sealed this

Twenty-second Day of October, 1991

Attest:

HARRY F. MANBECK, JR.

Attesting Officer     Commissioner of Patents and Trademarks